US 11,987,621 B2

(12) United States Patent
Haas et al.

(10) Patent No.: US 11,987,621 B2
(45) Date of Patent: *May 21, 2024

(54) ANTIBODIES FOR IL-17C

(71) Applicants: MORPHOSYS AG, Planegg (DE);
GALAPAGOS NV, Mechelen (BE)

(72) Inventors: Jan Dominik Haas, Munich (DE);
Jürgen Klattig, Peißenberg (DE); Nick Ernest René Vandeghinste, Mechelen (BE)

(73) Assignees: MORPHOSYS AG, Planegg (DE);
GALAPAGOS NV, Mechelen (BE)

( * ) Notice: Subject to any disclaimer, the term of this patent is extended or adjusted under 35 U.S.C. 154(b) by 510 days.

This patent is subject to a terminal disclaimer.

(21) Appl. No.: 16/822,844

(22) Filed: Mar. 18, 2020

(65) Prior Publication Data

US 2020/0216529 A1    Jul. 9, 2020

Related U.S. Application Data

(60) Division of application No. 16/286,231, filed on Feb. 26, 2019, now Pat. No. 10,633,439, which is a continuation of application No. 16/058,143, filed on Aug. 8, 2018, now Pat. No. 10,259,869, which is a continuation of application No. PCT/EP2017/053592, filed on Feb. 17, 2017.

(30) Foreign Application Priority Data

Feb. 19, 2016 (EP) .................................. 16156582
Feb. 22, 2016 (EP) .................................. 16156651

(51) Int. Cl.
*C07K 16/24* (2006.01)
*A61K 39/00* (2006.01)
*C12N 15/62* (2006.01)
*C12N 15/63* (2006.01)
*A61K 39/395* (2006.01)

(52) U.S. Cl.
CPC .......... *C07K 16/244* (2013.01); *C12N 15/62* (2013.01); *C12N 15/63* (2013.01); *A61K 39/395* (2013.01); *A61K 2039/505* (2013.01); *A61K 2039/54* (2013.01); *A61K 2039/545* (2013.01); *C07K 2317/21* (2013.01); *C07K 2317/24* (2013.01); *C07K 2317/33* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 10,259,869 B2 | 4/2019 | Haas et al. ............ C07K 16/244 |
| 10,633,439 B2 | 4/2020 | Haas et al. ............ C07K 16/244 |

FOREIGN PATENT DOCUMENTS

| WO | 99/60127 | 11/1999 | |
| WO | 2006/044840 | 4/2006 | |
| WO | 2007/047738 | 4/2007 | |
| WO | 2008/049070 | 4/2008 | |
| WO | 2013/016220 | 1/2013 | |
| WO | 2013/057241 | 4/2013 | |
| WO | WO-2013057241 A1 * | 4/2013 | .............. A61P 11/00 |
| WO | 2013/186236 | 12/2013 | |

OTHER PUBLICATIONS

Lloyd et al, Protein Engineering, Design & Selection, 2009, vol. 22, No. 3, pp. 159-168.*
Goel et al. The Journal of Immunology, 2004, 173(12):7358-7367.*
Edwards et al, (Journal of Molecular Biology, 2003, vol. 334, pp. 103-118.*
Brummell et al. (Biochemistry 32:1180-1187 (1993)).*
Burks et al. PNAS; 1997; vol. 94, pp. 412-417.*
Kobayashi et al. (Protein Engineering 12:879-844 (1999)).*
Vella et al, PLoS One; (https://doi.org/10.1371/journal.pone. 0243484 J.*
Qian et al, (Cytokine 89 (2017) 34-44); available online Feb. 14, 2016.*
Jungnickel, Oncogene 2017; 36, 4182-4190.*
Chang et al. "Interleukin-17C promotes Th17 cell responses and autoimmune disease via interleukin-17 receptor E" Immunity 2011 35:611-621.
Li et al. "Cloning and characterization of IL-17B and IL-17C, two new members of the IL-17 cytokine family" Proc. Natl. Acad. Sci. U. S. A. 2000 97:773-8.
Pappu et al. "The IL-17 Family Cytokines in Immunity and Disease" J. Clin. Immunol. 2010 30:185-195.
Ramirez-Carrozzi et al. "IL-17C regulates the innate immune function of epithelial cells in an autocrine manner" Nature Immunology 2011 12:12.
Song et al. "IL-17RE is the functional receptor for IL-17C and mediates mucosal immunity to infection with intestinal pathogens" Nature Immunology 2011 12:12.
Song "Alterations in the microbiota drive interleukin-17C production from intestinal epithelial cells to promote tumorigenesis" Immunity 2014 40:140-152.
Yamaguchi et al. "IL-17B and IL-17C are associated with TNF-alpha production and contribute to the exacerbation of inflammatory arthritis" J. Immunol 2007 179:7128-36.
Extended European Search Report dated Aug. 1, 2016 from EP 16156582.5 filed Feb. 19, 2016.

(Continued)

Primary Examiner — Daniel E Kolker
Assistant Examiner — Katherine Ann Holtzman
(74) Attorney, Agent, or Firm — Licata & Tyrrell P.C.; Kathleen A. Tyrrell

(57) ABSTRACT

The present invention provides antibodies or antibody fragments binding to human IL-17C. In particular, it relates to antibodies or antibody fragments that have combined beneficial properties and are therefore useful for the treatment of humans having, for example, atopic dermatitis or psoriasis.

17 Claims, 11 Drawing Sheets

Specification includes a Sequence Listing.

(56) References Cited

OTHER PUBLICATIONS

International Search Report dated Apr. 25, 2017 from PCT/EP2017/053592 filed Feb. 17, 2017.
Johnston et al. "Keratinocyte overexpression of IL-17C promotes psoriasiform skin inflammation" J. Immun. 2013 190 (5) :2252-2262.
Office Communication dated Mar. 6, 2019 in U.S. Appl. No. 16/058,143 filed Aug. 8, 2018.
Office Communication dated Nov. 29, 2018 in U.S. Appl. No. 16/058,143, filed Aug. 8, 2018.
Office Communication dated Aug. 22, 2019 in U.S. Appl. No. 16/286,231, filed Feb. 26, 2019.
Office Communication dated Dec. 23, 2019 in U.S. Appl. No. 16/286,231, filed Feb. 26, 2019.

\* cited by examiner

ANTIBODIES FOR IL-17C

This patent application is a divisional of U.S. application Ser. No. 16/286,231 filed Feb. 26, 2019, which is a continuation of U.S. application Ser. No. 16/058,143, filed Aug. 8, 2018, now issued as U.S. Pat. No. 10,259,869, which is a continuation of PCT/EP2017/053592 filed Feb. 17, 2017 which claims priority to EP 16156582.5 filed Feb. 19, 2016 and EP 16156651.8 filed Feb. 22, 2016, the contents of each of which are herein incorporated by reference in their entireties.

FIELD OF THE INVENTION

The present application relates to antibodies or antibody fragments which interact with human IL-17C. The invention also relates to nucleic acids, vectors and host cells capable of expressing said antibodies or fragments thereof, pharmaceutical compositions comprising said antibodies or fragments thereof and uses of said antibodies or fragments thereof for the treatment of specific diseases.

BACKGROUND

IL-17C is a secreted homodimer of the IL-17 protein family. In vitro it has been shown that IL-17C stimulates the release of TNF-α and IL-1β from the monocytic cell line THP-1 (Li et al. (2000) Proc. Natl. Acad. Sci. U. S. A. 97, 773-8). IL-17C can induce the mRNA expression of inflammatory cytokines such as IL-1β, IL-6 and IL-23 in peritoneal exudates cells (PECS) and the 3T3 cell line (Yamaguchi et al. (2007) J. Immunol 179, 7128-36).

The role of IL-17C as a proinflammatory cytokine relevant for host defense was postulated in several studies (Chang et al. (2011) Immunity 35, 611-621, Song et al. (2011) Nature Immunology 12, 12, Ramirez-Carrozzi et al. (2011) Nature Immunology 12, 12). Also a potential role in the progression of specific tumours and cancerous tissues was recently shown (Xinyang Song (2014) Immunity 40, 140-152).

Recently in WO 2013/057241 it was experimentally evaluated that inhibition of IL-17C is a promising approach to treat inflammatory disorders. However, respective antibodies used in WO 2013/057241 were surrogate antibodies specific for mouse IL-17C, but were shown not to be reactive to human IL-17C at all. In addition, further antibodies that antagonize IL-17C were already suggested (e.g. in WO 1999/060127), but are either polyclonal sera or surrogate antibodies which specifically bind to mouse IL-17C only.

Accordingly, a need exists to study and identify antibodies that bind to human IL-17C to ameliorate IL-17C related diseases or disorders in human.

SUMMARY OF THE INVENTION

The present disclosure provides novel antibodies and antibody fragments. The antibodies and antibody fragments disclosed herein bind to human IL-17C and also cross-react with IL-17C from the cynomolgus monkey and the mouse. In addition the disclosed antibodies inhibit binding of IL-17C to its receptor throughout the relevant species— human, mouse and cynomolgus monkey—with an $IC_{50}$ concentration of 80 pM or less. As disclosed and exemplified herein, said antibodies proved to be effective in various in vivo mouse models for atopic dermatitis and psoriasis.

Thus, the disclosed antibodies or antibody fragments are superior in terms of effectiveness and provide well suited and promising compounds for the treatment of humans having, for example, atopic dermatitis or psoriasis.

The present disclosure provides antibodies or antibody fragments that bind to human IL-17C having CDR regions according to Table 1 of the present specification. The present disclosure also provides specific antibodies or antibody fragments having a variable heavy chain region and a variable light chain CDR regions comprising the amino acid sequences according to Table 1 of the present specification.

The present disclosure also provides specific antibodies or antibody fragments which compete with the specific antibodies or antibody fragments disclosed herein. The present disclosure also provides specific antibodies or antibody fragments which bind to the same epitope as the specific antibodies or antibody fragments disclosed herein.

The present disclosure also provides the isolated antibodies or antibody fragments of the present disclosure for use in medicine.

The present disclosure also provides also provides methods for treating a subject suffering from a disorder, such as an inflammatory disorder, by administering to said subject an effective amount of the antibodies or antibody fragments of the present disclosure. Preferably said subject is a human.

The present disclosure also provides pharmaceutical compositions comprising the isolated antibodies or antibody fragments of the present disclosure, and a pharmaceutically acceptable carrier.

The present disclosure also provides nucleic acids encoding the antibodies or antibody fragments of the present disclosure.

The present disclosure also provides vectors comprising nucleic acids encoding the antibodies or antibody fragment antibodies of the present disclosure.

The present disclosure also provides host cell comprising vector or nucleic acids encoding the antibodies or antibody fragments of the present disclosure.

There is utility in the claimed antibodies or antibody fragments. Furthermore, there is utility in the claimed method to identify such antibodies or fragments.

Utilization of the claimed antibodies or antibody fragments is to alter the biological activity of human IL-17C. In particular the claimed antibodies or antibody fragments are for therapeutic use, such as the treatment of inflammatory disorders like e.g. rheumatoid arthritis, psoriasis, pulmonary inflammation, COPD and/or the treatment of atopic dermatitis (AD), including moderate-to-severe AD.

*** p<0.001. Right panel: representative images of mouse ears from animals from different treatment groups were acquired on the Bruker In-vivo Xtreme Imager 24h after injection of the Prosense 680 probe. (DEX: dexamethasone; EtOH: ethanol)

Figure 3:
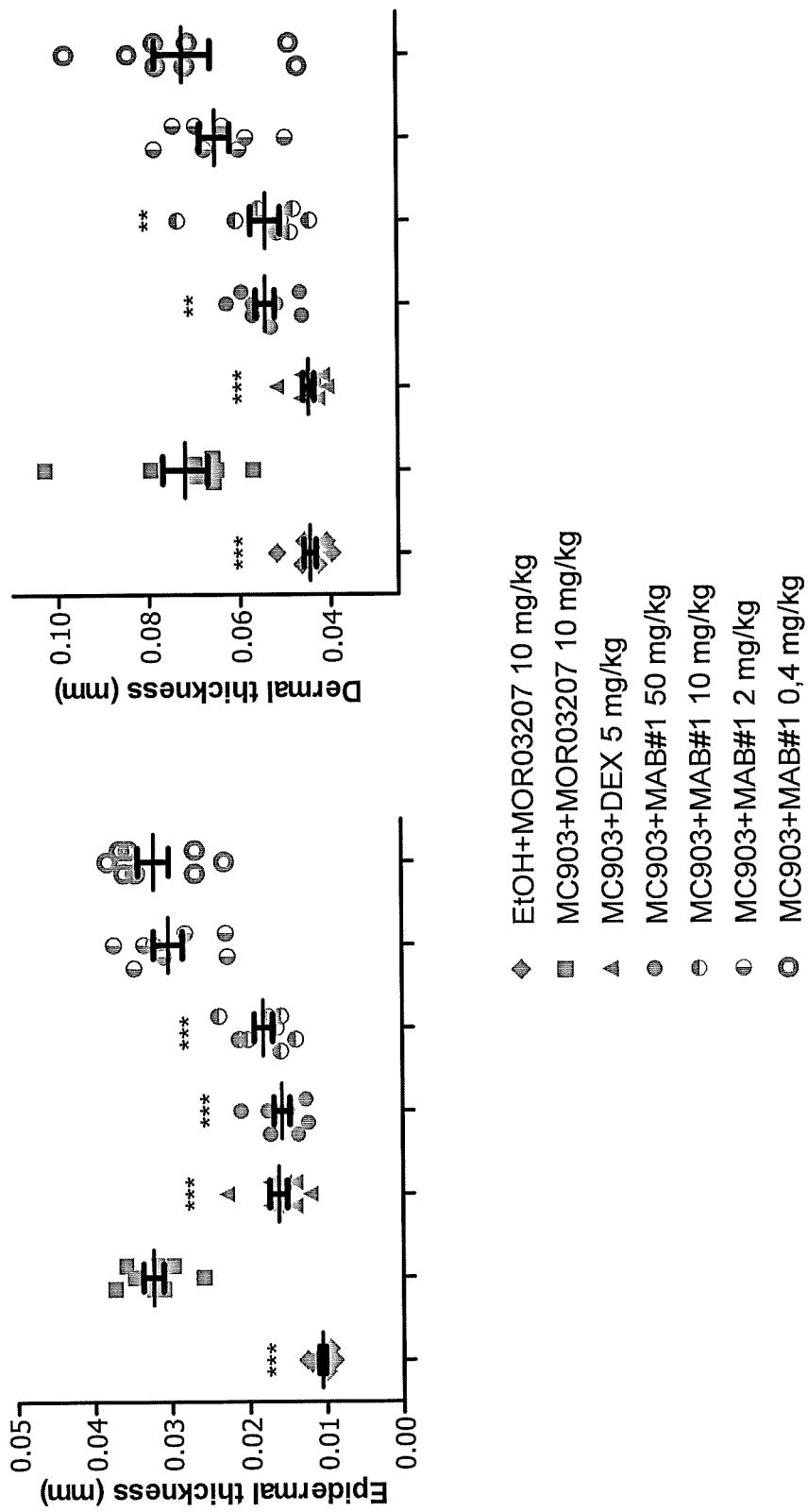

FIG. 3: MAB#1 dose-dependently reduces the thickening of epidermal and dermal skin layer induced by topical application of MC903 on ear skin.
Data are presented as individual data points (n=8 per group) and mean values (horizontal lines)±SEM. Statistical significance versus MC903+MOR03207 was calculated using ANOVA and Dunnett's multiple comparison test: * p<0.05;  p<0.01; * p<0.001. Left panel: data for epidermal thickness; Right panel: data for dermal thickness.

Figure 4:
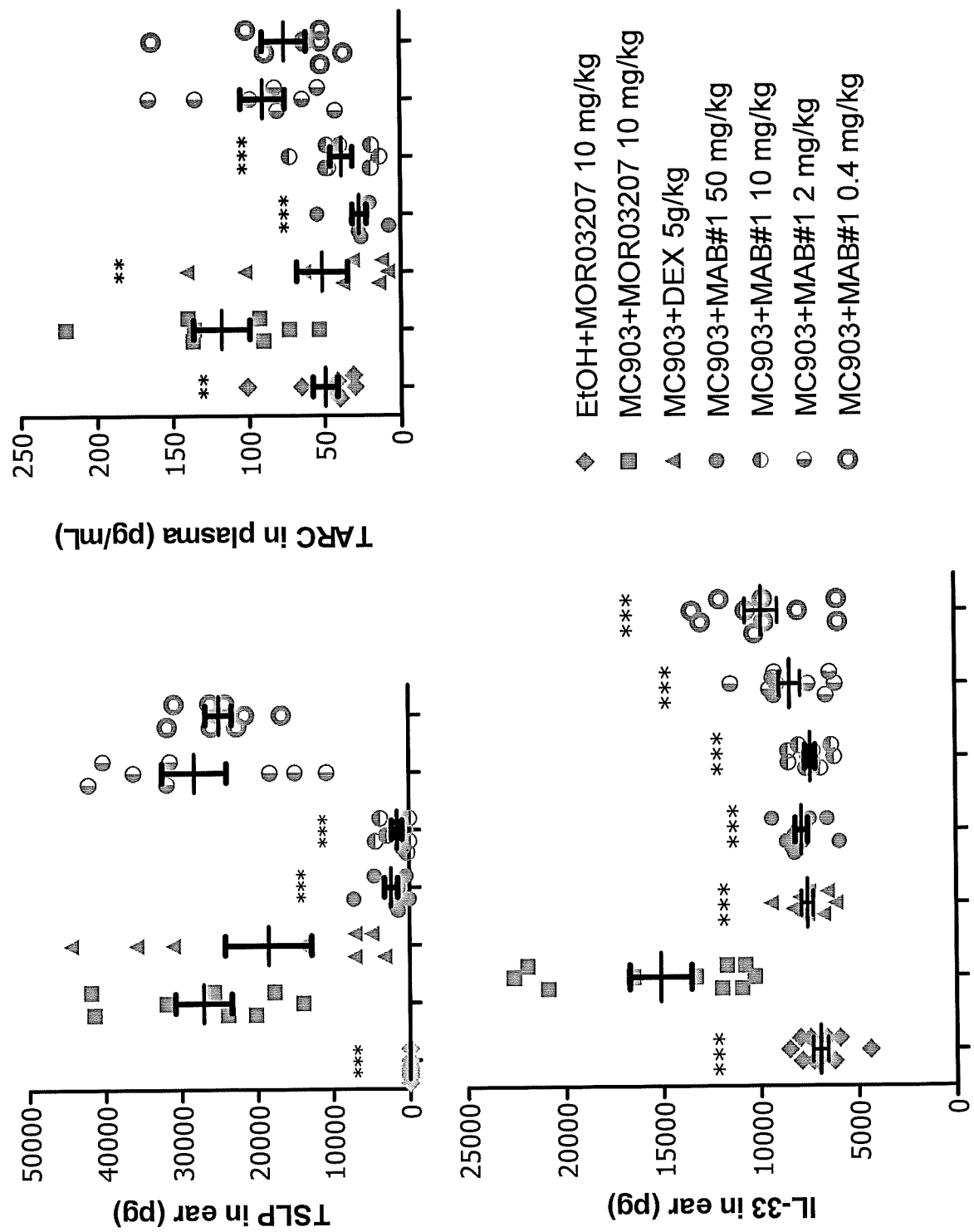

FIG. 4: MAB#1 dose-dependently inhibits the MC903-mediated increase in TSLP and IL-33 expresssion in ear and TARC levels in plasma.
Data are presented as individual data points (n=8 per group) and mean values (horizontal lines)±SEM. Statistical significance versus MC903+MOR03207 group was calculated using ANOVA and Dunnett's multiple comparison test: * p<0.05; p<0.01; *p<0.001. Top left panel: data for TSLP protein expression in ear; Bottom left panel: data for IL-33 protein expression in ear; Top right panel: data for TARC protein levels in plasma.

Figure 5:
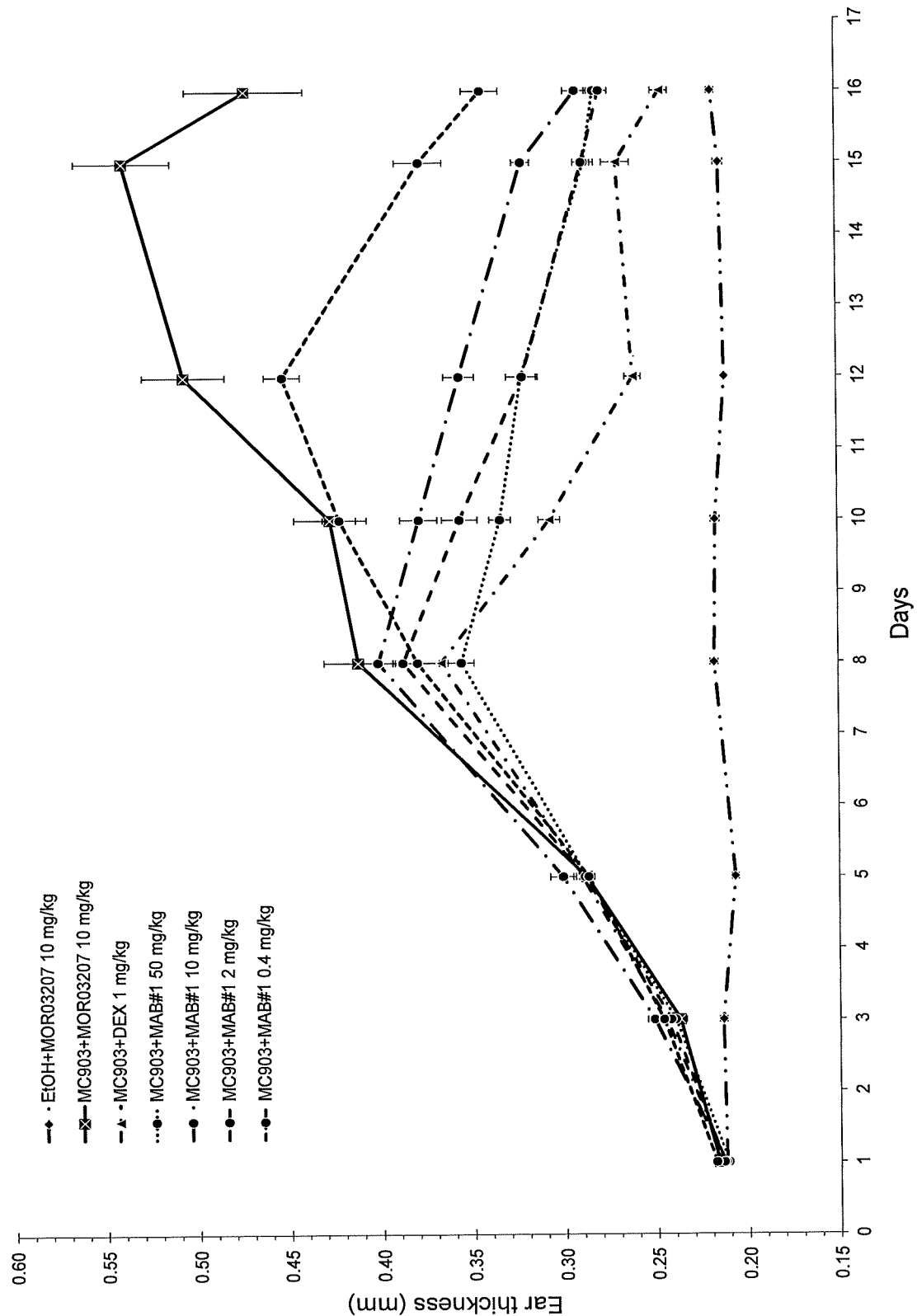

FIG. 5: Therapeutic administration of MAB#1 dose-dependently reduces the ear thickening induced by topical application of MC903 on ear skin.
Data are expressed as mean values±SEM (n=10 per group). Statistical significance versus MC903+MOR03207 was calculated using ANOVA and Dunnett's multiple comparison test: * p<0.05; p<0.01; *p<0.001. DEX: dexamethasone; EtOH: ethanol.

Figure 6:
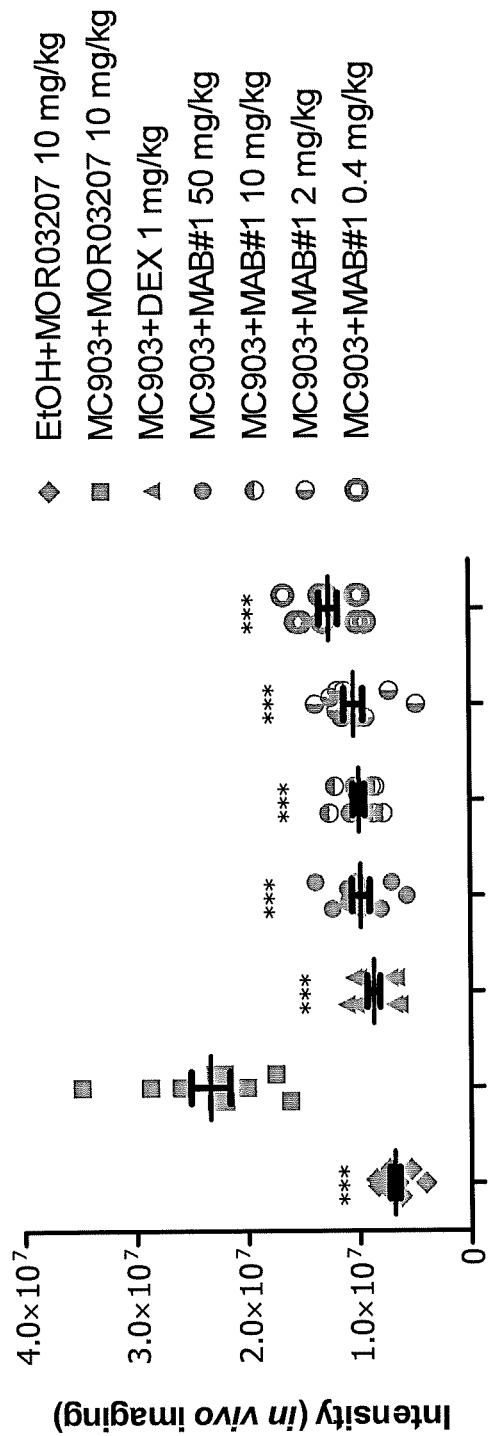

FIG. 6: Therapeutic administration of MAB#1 dose-dependently reduces the ear inflammation induced by topical application of MC903 on ear skin.
Ear inflammation was assessed at Day 12 using in vivo imaging and the signal intensity in ears is graphically represented. Individual data points (n=10 per group) represent the average intensity of both ears; data are also shown as mean values (horizontal lines)±SEM. Statistical significance versus MC903+MOR03207 was calculated using ANOVA and Dunnett's multiple comparison test: * p<0.05; p<0.01; *p<0.001. DEX: dexamethasone; EtOH: ethanol.

Figure 7:
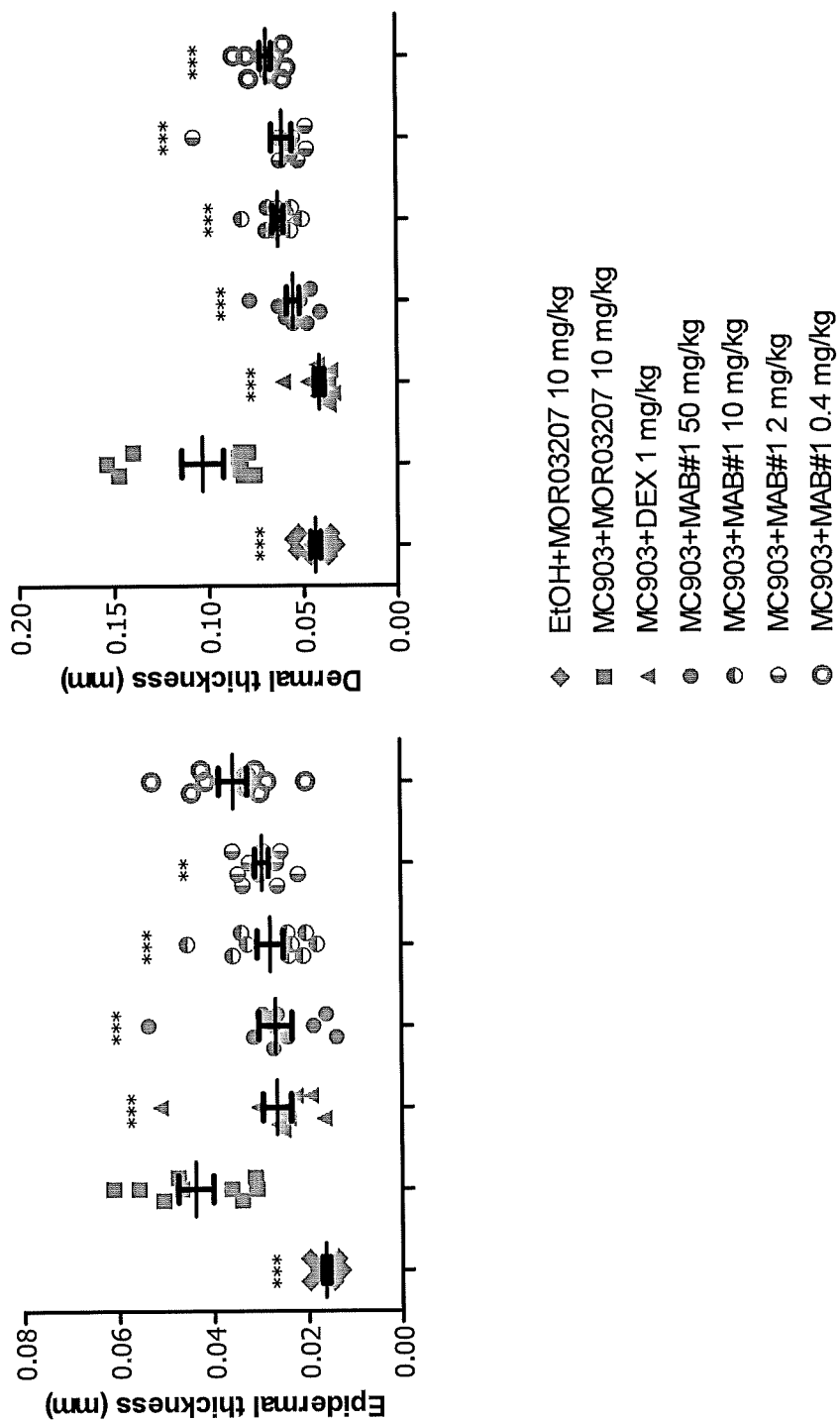

FIG. 7: Therapeutic administration of MAB#1 dose-dependently reduces the thickening of epidermal and dermal skin layer induced by topical administration of MC903 on ear skin.
Data are presented as individual data points (n=10 per group) and mean values (horizontal lines)±SEM. Statistical significance versus MC903+MOR03207 was calculated using ANOVA and Dunnett's multiple comparison test: * p<0.05; p<0.01; *p<0.001. Left panel: data for epidermal thickness; Right panel: data for dermal thickness. DEX: dexamethasone; EtOH: ethanol.

Figure 8:
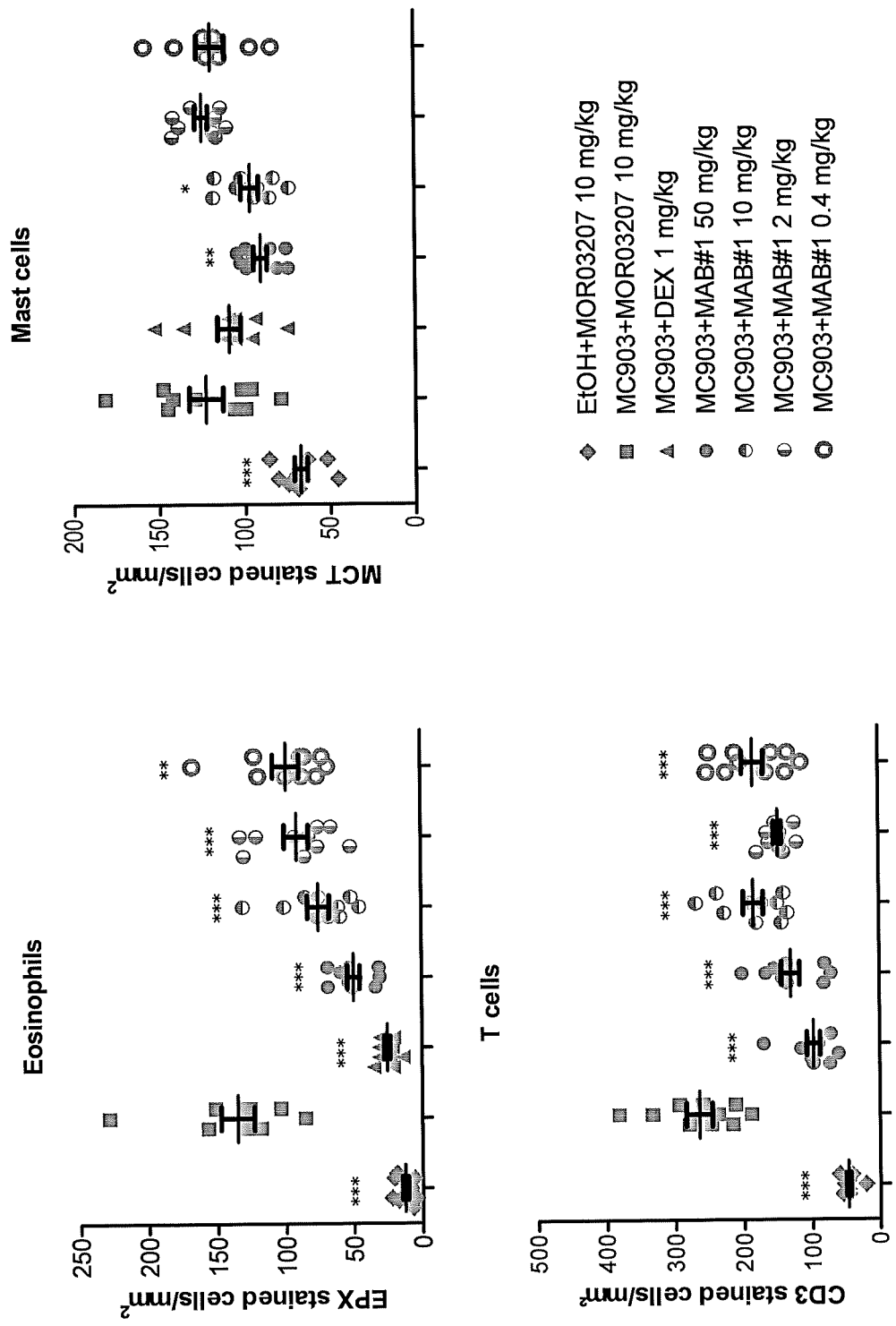

FIG. 8: Therapeutic administration of MAB#1 dose-dependently reduces the dermal infiltration of eosinophils, T cells and mast cells.
Data are presented as individual data points (n=10 per group) and mean values (horizontal lines)±SEM. Statistical significance versus MC903+MOR03207 was calculated using ANOVA and Dunnett's multiple comparison test: * p<0.05; p<0.01; *p<0.001. Top left panel: data for eosinophils; Top right panel: data for mast cells; Bottom left panel: data for T cells. DEX: dexamethasone; EtOH: ethanol.

Figure 9:
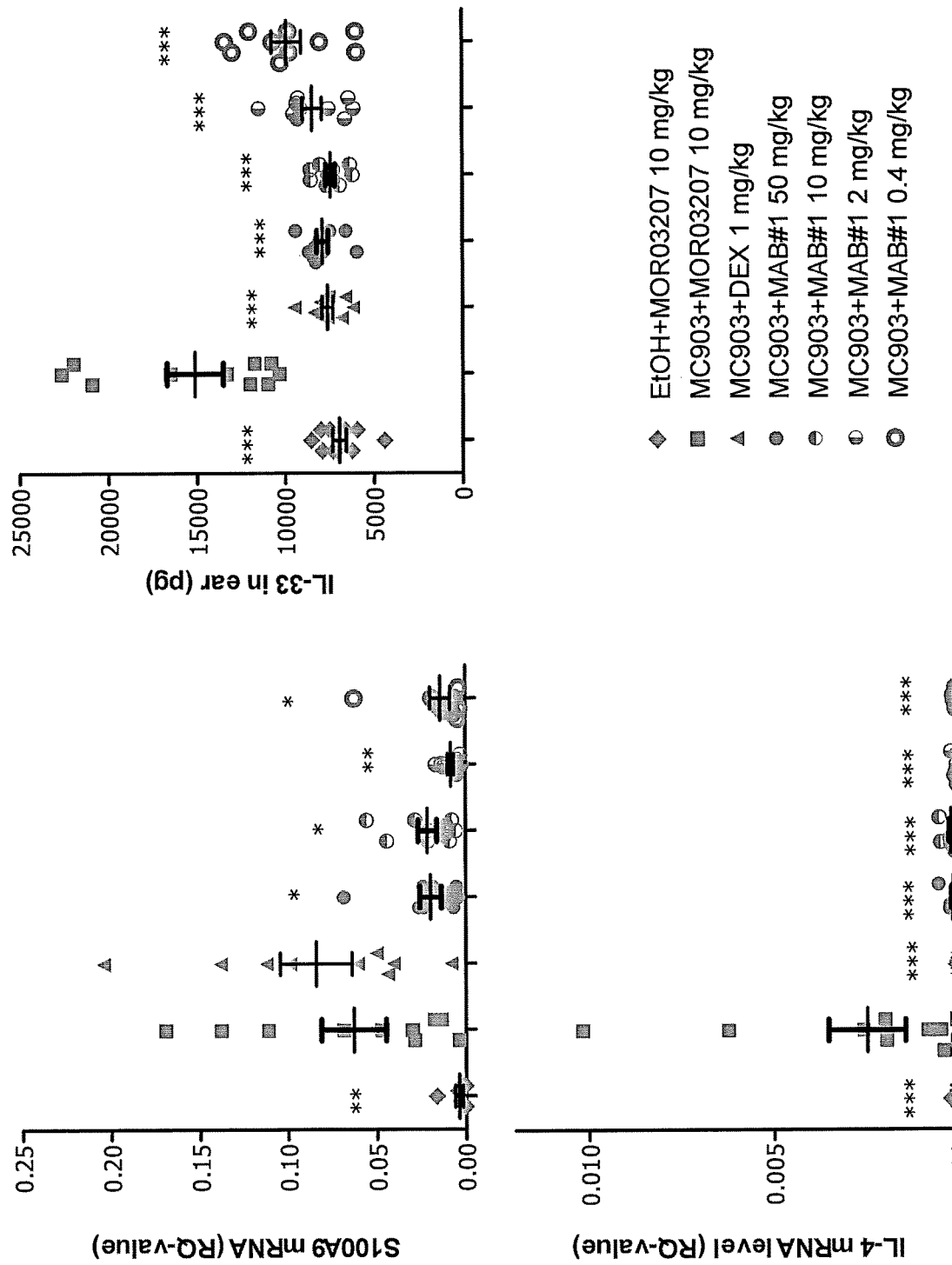

FIG. 9: Therapeutic administration of MAB#1 reduces expression of IL-33, IL-4 and S100A9, which were still increased at Day 16 (11 days after stopping MC903 application).
Data are presented as individual data points (n=10 per group) and mean values (horizontal lines)±SEM. Statistical significance versus MC903+MOR03207 group was calculated using ANOVA and Dunnett's multiple comparison test: * p<0.05; p<0.01; *p<0.001. Top left panel: data for S100A9 mRNA expression in ear; Bottom left panel: data for IL-4 mRNA expression in ear; Top right panel: data for IL-33 protein levels in ear.

Figure 10:
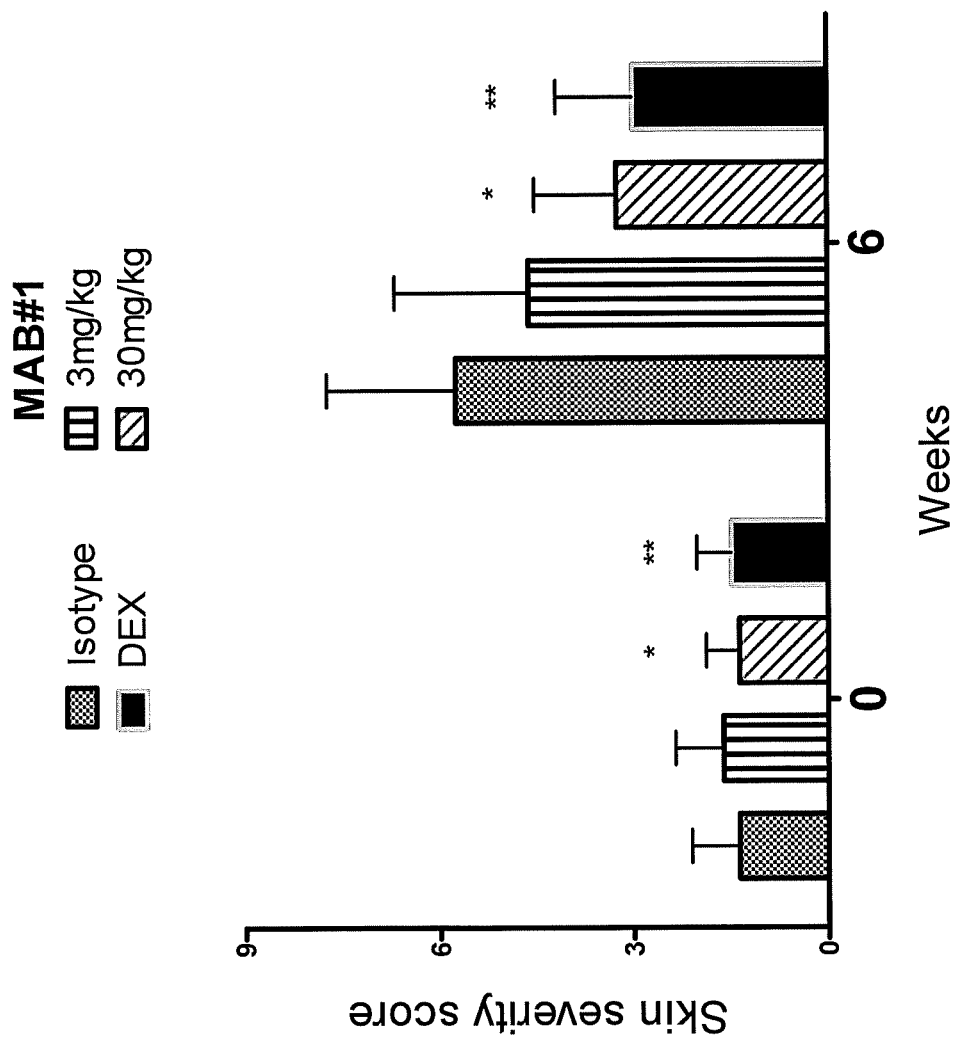

FIG. 10: MAB#1 reduces macroscopic clinical signs of AD-like inflammation in the spontaneous & chronic Flaky Tail model
Clinical scoring of cutaneous inflammation for each mouse was done at start (week 0) and at end (week 6) of treatment. Data are the mean±SD for each treatment group (n=8 per group). Statistical significance versus the isotype antibody treated group was calculated using ANOVA and Dunnett's multiple comparison test (* p<0.05; p<0.01; *p<0.001).

Figure 11:
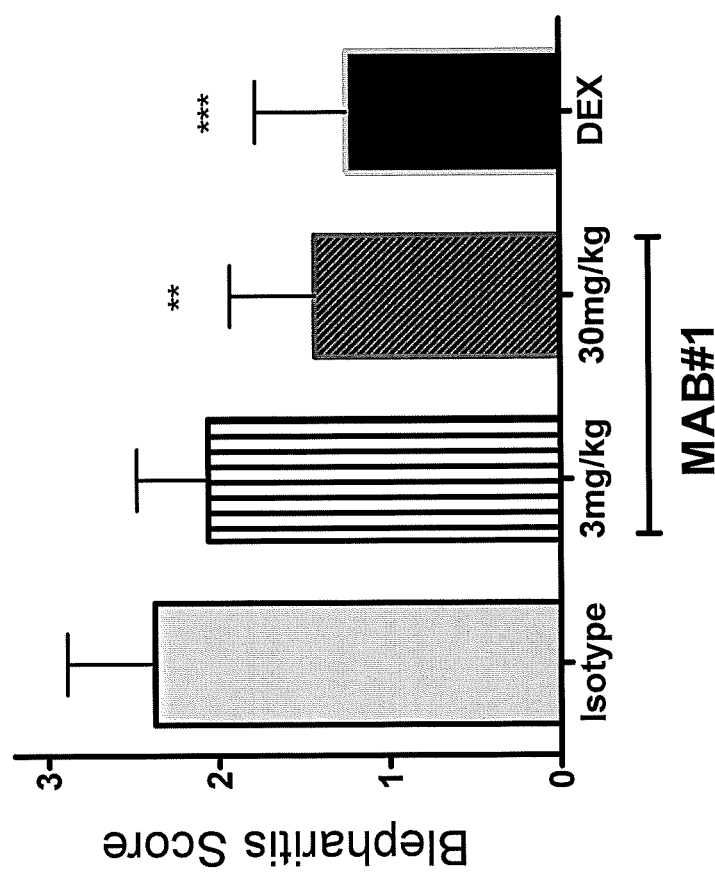

FIG. 11: MAB#1 reduces eczematous-like eyelid inflammation in the spontaneous & chronic Flaky Tail model.
Skin eyelid inflammation was scored at end of the treatment (week 6). Data are the mean±SD for each treatment group (n=8 per group). Statistical significance versus the isotype antibody treated group was calculated using ANOVA and Dunnett's multiple comparison test (* p<0.05; p<0.01 ; *p<0.001).

DETAILED DESCRIPTION OF THE INVENTION

The disclosure pertains to a number of antibodies or antibody fragments that recognize human IL-17C.
Definitions:
The term "IL-17C" refers to a protein known as interleukin 17C.
Human IL-17C has the amino acid sequence of (UniProt Q9P0M4):

(SEQ ID NO: 1)
MTLLPGLLFLTWLHTCLAHHDPSLRGHPHSHGTPHCYSAEEELPLGQA

PPHLLARGAKWGQALPVALVSSLEAASHRGRHERPSATTQCPVLRPE

EVLEADTHQRSISPWRYRVDTDEDRYPQKLAFAECLCRGCIDARTGR

ETAALNSVRLLQSLLVLRRRPCSRDGSGLPTPGAFAFHTEFIHVPVG

CTCVLPRSV

Mouse IL-17C has the amino acid sequence of (UniProt Q8K4C5):

(SEQ ID NO: 2)
MSLLLLGWLPTGMTHQDPPSWGKPRSHRTLRCYSAEELSHGQAPPHL

LTRSARWEQALPVALVASLEATGHRRQHEGPLAGTQCPVLRPEEVLE

ADTHERSISPWRYRIDTDENRYPQKLAVAECLCRGCINAKTGRETAA

LNSVQLLQSLLVLRRQPCSRDGTADPTPGSFAFHTEFIRVPVGCTCV

LPRSTQ

Cynomolgus monkey IL-17C has the amino acid sequence of (XP_005592825.1):

(SEQ ID NO: 3)
MTLLPGLLFLTWLHACLAHQDPFLRGHPHTHGTPRCYSAEELPLGQA

PPHLLARGAKWGQALPVALVSSLEAAGHRRRHDRPSAATQCPVLRPE

EVLEADTHQRSISPWRYRVDTDEDRYPQKLAFAECLCRGCIDPRTGR

ETAALNSVRLLQSLLVLRRRPCSRDGSGLPTPGAFAFHTEFIRVPVG

CTCVLPRSV

The term "IL17RA" refers to a protein known as interleukin 17 receptor A. Human IL17RA has the amino acid sequence of (UniProt Q96F46):

(SEQ ID NO: 4)
MGAARSPPSAVPGPLLGLLLLLLGVLAPGGASLRLLDHRALVCSQPG

LNCTVKNSTCLDDSWIHPRNLTPSSPKDLQIQLHFAHTQQGDLFPVA

HIEWTLQTDASILYLEGAELSVLQLNTNERLCVRFEFLSKLRHHHRR

WRFTFSHFVVDPDQEYEVTVHHLPKPIPDGDPNHQSKNFLVPDCEHA

RMKVTTPCMSSGSLWDPNITVETLEAHQLRVSFTLWNESTHYQILLT

SFPHMENHSCFEHMHHIPAPRPEEFHQRSNVTLTLRNLKGCCRHQVQ

IQPFFSSCLNDCLRHSATVSCPEMPDTPEPIPDYMPLWVYWFITGIS

ILLVGSVILLIVCMTWRLAGPGSEKYSDDTKYTDGLPAADLIPPPLK

PRKVWIIYSADHPLYVDVVLKFAQFLLTACGTEVALDLLEEQAISEA

GVMTWVGRQKQEMVESNSKIIVLCSRGTRAKWQALLGRGAPVRLRCD

HGKPVGDLFTAAMNMILPDFKRPACFGTYVVCYFSEVSCDGDVPDLF

GAAPRYPLMDRFEEVYFRIQDLEMFQPGRMHRVGELSGDNYLRSPGG

RQLRAALDRFRDWQVRCPDWFECENLYSADDQDAPSLDEEVFEEPLL

PPGTGIVKRAPLVREPGSQACLAIDPLVGEEGGAAVAKLEPHLQPRG

QPAPQPLHTLVLAAEEGALVAAVEPGPLADGAAVRLALAGEGEACPL

LGSPGAGRNSVLFLPVDPEDSPLGSSTPMASPDLLPEDVREHLEGLM

LSLFEQSLSCQAQGGCSRPAMVLTDPHTPYEEEQRQSVQSDQGYISR

SSPQPPEGLTEMEEEEEEEQDPGKPALPLSPEDLESLRSLQRQLLFR

QLQKNSGWDTMGSESEGPSA

The term "IL17RE" refers to a protein known as interleukin 17 receptor E. Human IL17RE has the amino acid sequence of (UniProt Q8NFR9):

(SEQ ID NO: 5)
MGSSRLAALLLPLLLIVIDLSDSAGIGFRHLPHWNTRCPLASHTDDS

FTGSSAYIPCRTWWALFSTKPWCVRVWHCSRCLCQHLLSGGSGLQRG

LFHLLVQKSKKSSTFKFYRRHKMPAPAQRKLLPRRHLSEKSHHISIP

SPDISHKGLRSKRTQPSDPETWESLPRLDSQRHGGPEFSFDLLPEAR

AIRVTISSGPEVSVRLCHQWALECEELSSPYDVQKIVSGGHTVELPY

EFLLPCLCIEASYLQEDTVRRKKCPFQSWPEAYGSDFWKSVHFTDYS

QHTQMVMALTLRCPLKLEAALCQRHDWHTLCKDLPNATARESDGWYV

LEKVDLHPQLCFKFSFGNSSHVECPHQTGSLTSWNVSMDTQAQQLIL

HFSSRMHATFSAAWSLPGLGQDTLVPPVYTVSQARGSSPVSLDLIIP

FLRPGCCVLVWRSDVQFAWKHLLCPDVSYRHLGLLILALLALLTLLG

VVLALTCRRPQSGPGPARPVLLLHAADSEAQRRLVGALAELLRAALG

GGRDVIVDLWEGRHVARVGPLPWLWAARTRVAREQGTVLLLWSGADL

RPVSGPDPRAAPLLALLHAAPRPLLLLAYFSRLCAKGDIPPPLRALP

RYRLLRDLPRLLRALDARPFAEATSWGRLGARQRRQSRLELCSRLER

EAARLADLG

Murine IL17RE has the amino acid sequence of (UniProt Q8BH06):

(SEQ ID NO: 6)
MGSPRLAALLLSLPLLLIGLAVSARVACPCLRSWTSHCLLAYRVDKR

FAGLQWGWFPLLVRKSKSPPKFEDYWRHRTPASFQRKLLGSPSLSEE

SHRISIPSSAISHRGQRTKRAQPSAAEGREHLPEAGSQKCGGPEFSF

DLLPEVQAVRVTIPAGPKASVRLCYQWALECEDLSSPFDTQKIVSGG

HTVDLPYEFLLPCMCIEASYLQEDTVRRKKCPFQSWPEAYGSDFWQS

IRFTDYSQHNQMVMALTLRCPLKLEASLCWRQDPLTPCETLPNATAQ

ESEGWYILENVDLHPQLCFKFSFENSSHVECPHQSGSLPSWTVSMDT

QAQQLTLHFSSRTYATFSAAWSDPGLGPDTPMPPVYSISQTQGSVPV

TLDLIIPFLRQENCILVWRSDVHFAWKHVLCPDVSHRHLGLLILALL

ALTALVGVVLVLLGRRLLPGSGRTRPVLLLHAADSEAQRRLVGALAE

LLRTALGGGRDVIVDLWEGTHVARIGPLPWLWAARERVAREQGTVLL

LWNCAGPSTACSGDPQAASLRTLLCAAPRPLLLAYFSRLCAKGDIPR

PLRALPRYRLLRDLPRLLRALDAQPATLASSWSHLGAKRCLKNRLEQ

CHLLELEAAKDDYQGSTNSPCGFSCL

The terms "antagonist of IL-17C" and an "IL-17C antagonist", are used interchangeably herein and refer to any molecule which inhibits the activity or function of IL-17C. The term "IL-17C antagonist" includes, but is not limited to, antibodies or antibody fragments specifically binding to IL-17C. Preferably, an IL-17C antagonist in the present disclosure is an antibody specific for human IL-17C. Such an antibody may be of any type, such as a murine, a rat, a chimeric, a humanized or a human antibody.

The term "antibody" as used herein refers to a protein comprising at least two heavy (H) chains and two light (L) chains inter-connected by disulfide bonds which interacts with an antigen. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FR's arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. The term "antibody" includes for example, monoclonal antibodies, human antibodies, humanized antibodies, camelised antibodies and chimeric antibodies. The antibodies can be of any isotype (e.g., IgG, IgE, IgM, IgD, IgA and IgY), class (e.g., IgG1, IgG2, IgG3, IgG4, IgA1 and IgA2) or subclass. Both the light and heavy chains are divided into regions of structural and functional homology.

The phrase "antibody fragment", as used herein, refers to one or more portions of an antibody that retain the ability to specifically interact with (e.g., by binding, steric hindrance, stabilizing spatial distribution) an antigen. Examples of binding fragments include, but are not limited to, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883). Such single chain antibodies are also intended to be encompassed within the term "antibody fragment". These antibody fragments are obtained using conventional techniques known to those of skill in the art, and the fragments are screened for utility in the same manner as are intact antibodies. Antibody fragments can also be incorporated into single domain antibodies, maxibodies, minibodies, intrabodies, diabodies, triabodies, tetrabodies, v-NAR and bis-scFv (see, e.g., Hollinger and Hudson, (2005) Nature Biotechnology 23:1126-1136). Antibody fragments can be grafted into scaffolds based on polypeptides such as Fibronectin type III (Fn3) (see U.S. Pat. No. 6,703,199, which describes fibronectin polypeptide monobodies). Antibody fragments can be incorporated into single chain molecules comprising a pair of tandem Fv segments (VH-CH1-VH-CH1) which, together with complementary light chain polypeptides, form a pair of antigen-binding sites (Zapata et al., (1995) Protein Eng. 8:1057-1062; and U.S. Pat. No. 5,641,870).

A "human antibody" or "human antibody fragment", as used herein, includes antibodies and antibody fragments having variable regions in which both the framework and CDR regions are derived from sequences of human origin. Furthermore, if the antibody contains a constant region, the constant region also is derived from such sequences. Human origin includes, e.g., human germline sequences, or mutated versions of human germline sequences or antibody containing consensus framework sequences derived from human framework sequences analysis, for example, as described in Knappik et al., (2000) J Mol Biol 296:57-86).

The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S. Department of Health and Human Services (1991), eds. Kabat et al.; Lazikani et al., (1997) J. Mol. Bio. 273:927-948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mol. Biol. 273:927-948.

A "humanized antibody" or "humanized antibody fragment" is defined herein as an antibody molecule which has constant antibody regions derived from sequences of human origin and the variable antibody regions or parts thereof or only the CDRs are derived from another species. For example a humanized antibody can be CDR-grafted, wherein the CDRs of the variable domain are from a non-human origin, while one or more frameworks of the variable domain are of human origin and the constant domain (if any) is of human origin.

The term "chimeric antibody" or "chimeric antibody fragment" is defined herein as an antibody molecule which has constant antibody regions derived from, or corresponding to, sequences found in one species and variable antibody regions derived from another species. Preferably, the constant antibody regions are derived from, or corresponding to, sequences found in humans, and the variable antibody regions (e.g. VH, VL, CDR or FR regions) are derived from sequences found in a non-human animal, e.g. a mouse, rat, rabbit or hamster.

The term "isolated" refers to a compound, which can be e.g. an antibody or antibody fragment, that is substantially free of other antibodies or antibody fragments having different antigenic specificities. Moreover, an isolated antibody or antibody fragment may be substantially free of other cellular material and/or chemicals. Thus, in some aspects, antibodies provided are isolated antibodies which have been separated from antibodies with a different specificity. An isolated antibody may be a monoclonal antibody. An isolated antibody may be a recombinant monoclonal antibody. An isolated antibody that specifically binds to an epitope, isoform or variant of a target may, however, have cross-reactivity to other related antigens, e.g., from other species (e.g., species homologs).

The term "recombinant antibody", as used herein, includes all antibodies that are prepared, expressed, created or segregated by means not existing in nature. For example antibodies isolated from a host cell transformed to express the antibody, antibodies selected and isolated from a recombinant, combinatorial human antibody library, and antibodies prepared, expressed, created or isolated by any other means that involve splicing of all or a portion of a human immunoglobulin gene, sequences to other DNA sequences or antibodies isolated from an animal (e.g., a mouse) that is transgenic or transchromosomal for human immunoglobulin genes or a hybridoma prepared therefrom. Preferably, such recombinant antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. A recombinant antibody may be a monoclonal antibody. In an embodiment, the antibodies and antibody fragment disclosed herein are isolated from the Ylanthia® antibody library as disclosed in U.S. Ser. No. 13/321,564 or U.S. Ser. No. 13/299,367, which both herein are incorporated by reference.

The term "monoclonal antibody" as used herein refers to a preparation of antibody molecules of single molecular composition. A monoclonal antibody composition displays a unique binding site having a unique binding specificity and affinity for particular epitopes.

As used herein the term "binds specifically to", "specifically binds to", is "specific to/for" or "specifically recognizes", or the like, refers to measurable and reproducible interactions such as binding between a target and an antibody or antibody fragment, which is determinative of the presence of the target in the presence of a heterogeneous population of molecules including biological molecules. For example, an antibody or antibody fragment that specifically binds to a target (which can be an antigen or an epitope of an antigen) is an antibody or antibody fragment that binds this target with greater affinity, avidity, more readily, and/or with greater duration than it binds to other targets. In certain embodiments, an antibody or antibody fragment specifically binds to an epitope on a protein that is conserved among the protein from different species. In another embodiment, specific binding can include, but does not require exclusive binding. The antibodies or antibody fragments disclosed herein specifically bind to human IL-17C. Preferably, the disclosed antibodies or antibody fragments specific for human IL-17C specifically bind to IL-17C of another species, such as IL-17C from mouse, rat, rhesus monkey and/or cynomolgus monkey. Even more preferred the antibodies or antibody fragments disclosed herein are specific for human IL-17C, cynomolgus monkey IL-17C and mouse IL-17C. Methods for determining whether two molecules specifically bind are well known in the art and include, for example, a standard ELISA assay. The scoring may be carried out by standard color development (e.g. secondary antibody with horseradish peroxide and tetramethyl benzidine with hydrogen peroxide). The reaction in certain wells is scored by the optical density, for example, at 450 nm. Typical background (=negative reaction) may be 0.1 OD; typical positive reaction may be 1 OD. This means the difference positive/negative can be more than 5-fold. Typically, determination of binding specificity is performed by using not a single reference antigen, but a set of about three to five unrelated antigens, such as milk powder, BSA, transferrin or the like.

The term "avidity" is used to describe the combined strength of multiple bond interactions between proteins. Avidity is distinct from affinity which describes the strength of a single bond. As such, avidity is the combined synergistic strength of bond affinities (functional affinity) rather than the sum of bonds. With the antibodies of the present disclosure, both antigen-binding sites from the VH/VL pairs simultaneously interact with IL-17C . Whilst each single binding interaction may be readily broken (depending on the relative affinity), because many binding interactions are present at the same time, transient unbinding of a single site does not allow the molecule to diffuse away, and binding of that site is likely to be reinstated. The overall effect is synergistic, strong binding of antigen to antibody.

As used herein, the term "affinity" refers to the strength of interaction between the polypeptide and its target at a single site. Within each site, the binding region of the polypeptide interacts through weak non-covalent forces with its target at numerous sites; the more interactions, the stronger the affinity.

The term "$K_D$", as used herein, refers to the dissociation constant, which is obtained from the ratio of $K_d$ to $K_a$ (i.e. $K_d/K_a$) and is expressed as a molar concentration (M). $K_D$ values for antigen binding moieties like e.g. monoclonal antibodies can be determined using methods well established in the art. Methods for determining the $K_D$ of an antigen binding moiety like e.g. a monoclonal antibody are SET (soluble equilibrium titration) or surface plasmon resonance using a biosensor system such as a Biacore® system. In the present disclosure an antibody specific to IL-17C typically has a dissociation rate constant ($K_D$) ($k_{off}/k_{on}$) of less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-3}$M, less than $10^{-9}$M, less than $5\times10^{-10}$M, less than $10^{-10}$M, less than $5\times10^{-11}$M, less than $10^{-11}$M, less than $5\times10^{-12}$M, less than $10^{-12}$M, less than $5\times10^{-13}$M, less than $10^{-13}$M, less than $5\times10^{-14}$M, less than $10^{-14}$M, less than $5\times10^{-15}$M, or less than $10^{-15}$M or lower.

"Cross competes" means the ability of an antibody, antibody fragment or other antigen-binding moieties to interfere with the binding of other antibodies, antibody fragments or antigen-binding moieties to a specific antigen in a standard competitive binding assay. The ability or extent to which an antibody, antibody fragment or other antigen-binding moieties is able to interfere with the binding of another antibody, antibody fragment or antigen-binding moieties to a specific antigen, and, therefore whether it can be said to cross-compete according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competing uses an ELISA-based approach. A high throughput process for "epitope binning" antibodies based upon their cross-competition is described in International Patent Application No. WO 2003/48731. Cross-competition is present if the antibody or antibody fragment under investigation reduces the binding of one of the antibodies described in Table 1 to IL-17C by 60% or more, specifically by 70% or more and more specifically by 80% or more and if one of the antibodies described in Table 1 reduces the binding of said antibody or antibody fragment to IL-17C by 60% or more, specifically by 70% or more and more specifically by 80% or more.

The term "epitope" includes any proteinacious region which is specifically recognized by an antibody or fragment thereof or a T-cell receptor or otherwise interacts with a molecule. Generally epitopes are of chemically active surface groupings of molecules such as amino acids or carbohydrate or sugar side chains and generally may have specific three-dimensional structural characteristics, as well as specific charge characteristics. As will be appreciated by one of skill in the art, practically anything to which an antibody can specifically bind could be an epitope.

"Binds the same epitope as" means the ability of an antibody, antibody fragment or other antigen-binding moiety to bind to a specific antigen and binding to the same epitope as the exemplified antibody when using the same epitope mapping technique for comparing the antibodies. The epitopes of the exemplified antibody and other antibodies can be determined using epitope mapping techniques. Epitope mapping techniques are well known in the art. For example, conformational epitopes are readily identified by determining spatial conformation of amino acids such as by, e.g., hydrogen/deuterium exchange, x-ray crystallography and two-dimensional nuclear magnetic resonance.

Compositions of the present disclosure may be used for therapeutic or prophylactic applications. The present disclosure, therefore, includes a pharmaceutical composition containing an antibody (or functional antibody fragment) as disclosed herein and a pharmaceutically acceptable carrier or excipient therefor. In a related aspect, the present disclosure provides a method for treating an inflammatory disorder. Such method contains the steps of administering to a subject in need thereof an effective amount of the pharmaceutical composition that contains an antibody (or functional antibody fragment) as described or contemplated herein.

The present disclosure provides therapeutic methods comprising the administration of a therapeutically effective amount of an IL-17C antibody as disclosed to a subject in need of such treatment. A "therapeutically effective amount" or "effective amount", as used herein, refers to the amount of an IL-17C antibody necessary to elicit the desired biological response. In accordance with the subject invention, the therapeutic effective amount is the amount of an IL-17C antibody necessary to treat and/or prevent a disease.

"Subject" or "species", as used in this context refers to any mammal, including rodents, such as mouse or rat, and primates, such as cynomolgus monkey (*Macaca fascicularis*), rhesus monkey (*Macaca mulatta*) or humans (*Homo sapiens*). Preferably the subject is a primate, most preferably a human.

Embodiments:

In one embodiment, the present disclosure refers to an antibody or antibody fragment specific for IL-17C wherein said antibody or antibody fragment comprises (a) a HCDR1 region comprising the amino acid sequence of SEQ ID NO: 7, a HCDR2 region comprising the amino acid sequence of SEQ ID NO: 8, a HCDR3 region comprising the amino acid sequence of SEQ ID NO: 9, a LCDR1 region comprising the amino acid sequence of SEQ ID NO: 13, a LCDR2 region comprising the amino acid sequence of SEQ ID NO: 14 and a LCDR3 region comprising the amino acid sequence of SEQ ID NO: 15, or (b) a HCDR1 region comprising the amino acid sequence of SEQ ID NO: 20, a HCDR2 region comprising the amino acid sequence of SEQ ID NO: 21, a HCDR3 region comprising the amino acid sequence of SEQ ID NO: 22, a LCDR1 region comprising the amino acid sequence of SEQ ID NO: 26, a LCDR2 region comprising the amino acid sequence of SEQ ID NO: 27 and a LCDR3 region comprising the amino acid sequence of SEQ ID NO: 28.

In one embodiment, the present disclosure refers to an antibody or antibody fragment specific for IL-17C, wherein said antibody or antibody fragment comprises the HCDR1 region of SEQ ID NO: 7, the HCDR2 region of SEQ ID NO: 8, the HCDR3 region of SEQ ID NO: 9, the LCDR1 region of SEQ ID NO: 13, the LCDR2 region of SEQ ID NO: 14 and the LCDR3 region of SEQ ID NO: 15, or the HCDR1 region of SEQ ID NO: 20, the HCDR2 region of SEQ ID NO: 21, the HCDR3 region of SEQ ID NO: 22, the LCDR1 region of SEQ ID NO: 26, the LCDR2 region of SEQ ID NO: 27 and the LCDR3 region of SEQ ID NO: 28.

In another embodiment, the present disclosure refers to an antibody or antibody fragment specific for IL-17C wherein said antibody or antibody fragment comprises (a) a HCDR1 region comprising the amino acid sequence of SEQ ID NO: 10, a HCDR2 region comprising the amino acid sequence of SEQ ID NO: 11, a HCDR3 region comprising the amino acid sequence of SEQ ID NO: 12, a LCDR1 region comprising the amino acid sequence of SEQ ID NO: 13, a LCDR2 region comprising the amino acid sequence of SEQ ID NO: 14 and a LCDR3 region comprising the amino acid sequence of SEQ ID NO: 15, or (b) a HCDR1 region comprising the amino acid sequence of SEQ ID NO: 23, a HCDR2 region comprising the amino acid sequence of SEQ ID NO: 24, a HCDR3 region comprising the amino acid sequence of SEQ ID NO: 25, a LCDR1 region comprising the amino acid sequence of SEQ ID NO: 26, a LCDR2 region comprising the amino acid sequence of SEQ ID NO: 27 and a LCDR3 region comprising the amino acid sequence of SEQ ID NO: 28.

In a further embodiment, the present disclosure refers to an antibody or antibody fragment specific for IL-17C, wherein said antibody or antibody fragment comprises the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15, or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28.

In one embodiment, the present disclosure refers to an antibody or antibody fragment specific for IL-17C wherein said antibody or antibody fragment comprises (a) a HCDR1 region comprising the amino acid sequence of SEQ ID NO: 7, a HCDR2 region comprising the amino acid sequence of SEQ ID NO: 8, a HCDR3 region comprising the amino acid sequence of SEQ ID NO: 9, a LCDR1 region comprising the amino acid sequence of SEQ ID NO: 13, a LCDR2 region comprising the amino acid sequence of SEQ ID NO: 14 and a LCDR3 region comprising the amino acid sequence of SEQ ID NO: 15, or (b) a HCDR1 region comprising the amino acid sequence of SEQ ID NO: 10, a HCDR2 region comprising the amino acid sequence of SEQ ID NO: 11, a HCDR3 region comprising the amino acid sequence of SEQ ID NO: 12, a LCDR1 region comprising the amino acid sequence of SEQ ID NO: 13, a LCDR2 region comprising the amino acid sequence of SEQ ID NO: 14 and a LCDR3 region comprising the amino acid sequence of SEQ ID NO: 15, or (c) a HCDR1 region comprising the amino acid sequence of SEQ ID NO: 20, a HCDR2 region comprising the amino acid sequence of SEQ ID NO: 21, a HCDR3 region comprising the amino acid sequence of SEQ ID NO: 22, a LCDR1 region comprising the amino acid sequence of SEQ ID NO: 26, a LCDR2 region comprising the amino acid sequence of SEQ ID NO: 27 and a LCDR3 region comprising the amino acid sequence of SEQ ID NO: 28.

(d) a HCDR1 region comprising the amino acid sequence of SEQ ID NO: 23, a HCDR2 region comprising the amino acid sequence of SEQ ID NO: 24, a HCDR3 region comprising the amino acid sequence of SEQ ID NO: 25, a LCDR1 region comprising the amino acid sequence of SEQ ID NO: 26, a LCDR2 region comprising the amino acid sequence of SEQ ID NO: 27 and a LCDR3 region comprising the amino acid sequence of SEQ ID NO: 28.

In one embodiment, the present disclosure refers to an antibody or antibody fragment specific for IL-17C, wherein said antibody or antibody fragment comprises the HCDR1 region of SEQ ID NO: 7, the HCDR2 region of SEQ ID NO: 8, the HCDR3 region of SEQ ID NO: 9, the LCDR1 region of SEQ ID NO: 13, the LCDR2 region of SEQ ID NO: 14 and the LCDR3 region of SEQ ID NO: 15, or the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15, or the HCDR1 region of SEQ ID NO: 20, the HCDR2 region of SEQ ID NO: 21, the HCDR3 region of SEQ ID NO: 22, the LCDR1 region of SEQ ID NO: 26, the LCDR2 region of SEQ ID NO: 27 and the LCDR3 region of SEQ ID NO: 28, or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28.

In another embodiment of the present disclosure the antibody or antibody fragment specifically binds to human IL-17C.

In another embodiment of the present disclosure the antibody or antibody fragment is a monoclonal antibody or antibody fragment.

In another embodiment of the present disclosure the antibody or antibody fragment is a human, humanized or chimeric antibody or antibody fragment. In another embodiment of the present disclosure the antibody or antibody fragment is of the IgG isotype. In another embodiment the antibody or antibody fragment is IgG1.

In one embodiment, the present disclosure refers to an antibody or antibody fragment specific for IL-17C, wherein said antibody or antibody fragment comprises the HCDR1 region of SEQ ID NO: 7, the HCDR2 region of SEQ ID NO: 8, the HCDR3 region of SEQ ID NO: 9, the LCDR1 region of SEQ ID NO: 13, the LCDR2 region of SEQ ID NO: 14 and the LCDR3 region of SEQ ID NO: 15, and further comprises a heavy chain of SEQ ID NO: 17 or a light chain of SEQ ID NO: 16, or the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15 and further comprises a heavy chain of SEQ ID NO: 17 or a light chain of SEQ ID NO: 16, or the HCDR1 region of SEQ ID NO: 20, the HCDR2 region of SEQ ID NO: 21, the HCDR3 region of SEQ ID NO: 22, the LCDR1 region of SEQ ID NO: 26, the LCDR2 region of SEQ ID NO: 27 and the LCDR3 region of SEQ ID NO: 28 and further comprises a heavy chain of SEQ ID NO: 30 or a light chain of SEQ ID NO: 29, or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28, and further comprises a heavy chain of SEQ ID NO: 30 or a light chain of SEQ ID NO: 29.

In one embodiment, the present disclosure refers to an antibody or antibody fragment specific for IL-17C, wherein said antibody or antibody fragment comprises a heavy chain of SEQ ID NO: 17 and a light chain of SEQ ID NO: 16.

In one embodiment, the present disclosure refers to an antibody or antibody fragment specific for IL-17C, wherein said antibody or antibody fragment comprises a heavy chain of SEQ ID NO: 30 and a light chain of SEQ ID NO: 29.

In a further embodiment, the present disclosure refers to an antibody or antibody fragment specific for IL-17C, wherein said antibody or antibody fragment comprises a heavy chain of SEQ ID NO: 43 and a light chain of SEQ ID NO: 42.

In one embodiment, the present disclosure refers to an antibody or antibody fragment specific for IL-17C, wherein said antibody or antibody fragment comprises a heavy chain of SEQ ID NO: 56 and a light chain of SEQ ID NO: 55.

In another embodiment of the present disclosure the antibody or antibody fragment is an isolated antibody or antibody fragment.

In another embodiment of the present disclosure the antibody or antibody fragment is a recombinant antibody or antibody fragment.

In one embodiment, the present disclosure refers to an antibody or antibody fragment specific for IL-17C for use in the treatment of a disorder or condition associated with the undesired presence of IL-17C.

In one embodiment, the present disclosure refers to a nucleic acid composition comprising a nucleic acid sequence or a plurality of nucleic acid sequences encoding an antibody or antibody fragment specific for IL-17C, wherein said antibody or antibody fragment comprises the HCDR1 region of SEQ ID NO: 7, the HCDR2 region of SEQ ID NO: 8, the HCDR3 region of SEQ ID NO: 9, the LCDR1 region of SEQ ID NO: 13, the LCDR2 region of SEQ ID NO: 14 and the LCDR3 region of SEQ ID NO: 15, or the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15, or the HCDR1 region of SEQ ID NO: 20, the HCDR2 region of SEQ ID NO: 21, the HCDR3 region of SEQ ID NO: 22, the LCDR1 region of SEQ ID NO: 26, the LCDR2 region of SEQ ID NO: 27 and the LCDR3 region of SEQ ID NO: 28, or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28.

In another embodiment, the present disclosure refers to a vector composition comprising a vector or a plurality of vectors comprising the nucleic acid sequence or plurality of nucleic acid sequences encoding an antibody or antibody fragment as disclosed in Table 1.

In one embodiment, the present disclosure refers to a cell comprising a vector composition comprising a vector or a plurality of vectors comprising the nucleic acid sequence or plurality of nucleic acid sequences encoding an antibody or antibody fragment as disclosed in Table 1.

In another embodiment, the present disclosure refers to a pharmaceutical composition comprising an antibody or antibody fragment as disclosed in Table 1 and a pharmaceutically acceptable carrier or excipient.

In one embodiment, said antibody or antibody fragment specific for IL-17C blocks the binding of IL-17C to the receptor of IL-17C. In a further embodiment, said antibody or antibody fragment specific for IL-17C blocks the binding of IL-17C to the receptor of IL-17C, wherein said receptor is IL17RE. In another embodiment the present disclosure refers to an antibody or antibody fragment specific for IL-17C, wherein said antibody or antibody fragment blocks the binding of IL-17C to IL17RE. In another embodiment said antibody or antibody fragment comprises the HCDR1 region of SEQ ID NO: 7, the HCDR2 region of SEQ ID NO: 8, the HCDR3 region of SEQ ID NO: 9, the LCDR1 region of SEQ ID NO: 13, the LCDR2 region of SEQ ID NO: 14 and the LCDR3 region of SEQ ID NO: 15, or the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15, or the HCDR1 region of SEQ ID NO: 20, the HCDR2 region of SEQ ID NO: 21, the HCDR3 region of SEQ ID NO: 22, the LCDR1 region of SEQ ID NO: 26, the LCDR2 region of SEQ ID NO: 27 and the LCDR3 region of SEQ ID NO: 28, or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28.

In another embodiment said antibody or antibody fragment comprises a heavy chain of SEQ ID NO: 17 and a light chain of SEQ ID NO: 16 or a heavy chain of SEQ ID NO: 30 and a light chain of SEQ ID NO: 29 or a heavy chain and a light chain that has at least 60%, at least 70%, at least 80%, at least 90% or at least 95% identity to the a heavy chain of SEQ ID NO: 17 or 30 and to the light chain of SEQ ID NO: 16 or 29.

In another embodiment the present disclosure refers to an antibody or antibody fragment specific for IL-17C wherein said antibody or antibody fragment bivalently binds to an IL-17C homodimer and forms a complex consisting of said antibody or antibody fragment and one IL-17C homodimer and wherein said antibody or antibody fragment blocks the binding of IL-17C to IL17RE.

In certain embodiments, said antibody or antibody fragment specific for IL-17C blocks the binding of IL-17C to one or more receptors of IL-17C. In another embodiment said antibody or antibody fragment comprises the HCDR1 region of SEQ ID NO: 7, the HCDR2 region of SEQ ID NO: 8, the HCDR3 region of SEQ ID NO: 9, the LCDR1 region of SEQ ID NO: 13, the LCDR2 region of SEQ ID NO: 14 and the LCDR3 region of SEQ ID NO: 15, or the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15, or the HCDR1 region of SEQ ID NO: 20, the HCDR2 region of SEQ ID NO: 21, the HCDR3 region of SEQ ID NO: 22, the LCDR1 region of SEQ ID NO: 26, the LCDR2 region of SEQ ID NO: 27 and the LCDR3 region of SEQ ID NO: 28, or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28.

In another embodiment said antibody or antibody fragment comprises a heavy chain of SEQ ID NO: 17 and a light chain of SEQ ID NO: 16 or a heavy chain of SEQ ID NO: 30 and a light chain of SEQ ID NO: 29 or a heavy chain and a light chain that has at least 60%, at least 70%, at least 80%, at least 90% or at least 95% identity to the a heavy chain of SEQ ID NO: 17 or 30 and to the light chain of SEQ ID NO: 16 or 29.

In alternative embodiments, said antibody or antibody fragment specific for the receptor of IL-17C blocks the binding of IL-17C to receptors of IL-17C, wherein the receptors of IL-17C include IL17RE and IL17RA. In alternative embodiments, said antibody or antibody fragment specific for the receptor of IL-17C blocks the binding of IL-17C to IL17RE and IL17RA. In certain embodiments, said antibody or antibody fragment specific for IL-17C blocks the binding of IL-17C to IL17RE with an $IC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM or 1 pM. In certain aspects the $IC_{50}$ concentration can be determined by ELISA; SET, FACS or MSD (Meso Scale Discovery). In another aspect the $IC_{50}$ concentration can be determined by the method as described herein in Example 3. In another embodiment said antibody or antibody fragment comprises a heavy chain of SEQ ID NO: 17 and a light chain of SEQ ID NO: 16 or a heavy chain of SEQ ID NO: 30 and a light chain of SEQ ID NO: 29 or a heavy chain and a light chain that has at least 60%, at least 70%, at least 80%, at least 90% or at least 95% identity to the a heavy chain of SEQ ID NO: 17 or 30 and to the light chain of SEQ ID NO: 16 or 29.

In one embodiment the disclosed antibody or antibody fragment is specific for human IL-17C. In a further embodiment the disclosed antibody or antibody fragment specific for IL-17C is cross-reactive with IL-17C of another species, such as IL-17C from mouse, rat, rhesus monkey and/or cynomolgus monkey. In another embodiment the antibody or antibody fragment is specific for human IL-17C, cynomolgus monkey IL-17C and mouse IL-17C. In a further embodiment the antibody or antibody fragment is specific for human IL-17C, cynomolgus monkey IL-17C and mouse IL-17C. In another embodiment the antibody or antibody fragment is specific for human IL-17C, cynomolgus monkey IL-17C and mouse IL-17C, wherein said antibody or antibody fragment comprises the HCDR1 region of SEQ ID NO: 7, the HCDR2 region of SEQ ID NO: 8, the HCDR3 region of SEQ ID NO: 9, the LCDR1 region of SEQ ID NO: 13, the LCDR2 region of SEQ ID NO: 14 and the LCDR3 region of SEQ ID NO: 15, or the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15, or the HCDR1 region of SEQ ID NO: 20, the HCDR2 region of SEQ ID NO: 21, the HCDR3 region of SEQ ID NO: 22, the LCDR1 region of SEQ ID NO: 26, the LCDR2 region of SEQ ID NO: 27 and the LCDR3 region of SEQ ID NO: 28, or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28.

In another embodiment said antibody or antibody fragment comprises a heavy chain of SEQ ID NO: 17 and a light chain of SEQ ID NO: 16 or a heavy chain of SEQ ID NO: 30 and a light chain of SEQ ID NO: 29 or a heavy chain and a light chain that has at least 60%, at least 70%, at least 80%, at least 90% or at least 95% identity to the a heavy chain of SEQ ID NO: 17 or 30 and to the light chain of SEQ ID NO: 16 or 29.

In yet another embodiment the disclosed antibody or antibody fragment specifically binds to human IL-17C, cynomolgus monkey IL-17C and mouse IL-17C and blocks the binding of human IL-17C, cynomolgus monkey IL-17C and mouse IL-17C to its specific receptor IL17RE with an $IC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM or 1 pM. In another aspect said antibody is in IgG1 format. In another embodiment said $IC_{50}$ concentration is determined in a Receptor Inhibition Assay as described herein in Example 3.

In yet another embodiment the disclosed antibody or antibody fragment specifically binds to human IL-17C and blocks the binding of human IL-17C to human IL17RE with an $IC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM or 1 pM. In another aspect said antibody is in IgG1 format. In another embodiments said $IC_{50}$ concentration is determined in a Receptor Inhibition Assay as described herein in Example 3.

In yet another embodiment the disclosed antibody or antibody fragment specifically binds to cynomolgus monkey IL-17C and blocks the binding of cynomolgus monkey IL-17C to cynomolgus monkey IL17RE with an $IC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM or 1 pM. In another aspect said antibody is in IgG1 format. In another embodiments said $IC_{50}$ concentration is determined in a Receptor Inhibition Assay as described herein in Example 3.

In yet another embodiment the disclosed antibody or antibody fragment specifically binds to human IL-17C, cynomolgus monkey IL-17C and mouse IL-17C, and blocks the binding of human IL-17C, cynomolgus monkey IL-17C and mouse IL-17C, to human IL17RE, cynomolgus monkey IL17RE and mouse IL17RE, respectively, each with an $IC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 1 nM, 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM or 1 pM. In a preferred embodiment said antibody or antibody fragment comprises the HCDR1 region of SEQ ID NO: 7, the HCDR2 region of SEQ ID NO: 8, the HCDR3 region of SEQ ID NO: 9, the LCDR1 region of SEQ ID NO: 13, the LCDR2 region of SEQ ID NO: 14 and the LCDR3 region of SEQ ID NO: 15, or the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15, or the HCDR1 region of SEQ ID NO: 20, the HCDR2 region of SEQ ID NO: 21, the HCDR3 region of SEQ ID NO: 22, the LCDR1 region of SEQ ID NO: 26, the LCDR2 region of SEQ ID NO: 27 and the LCDR3 region of SEQ ID NO: 28, or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28. In another embodiment said antibody or antibody fragment comprises a heavy chain of SEQ ID NO: 17 and a light chain of SEQ ID NO: 16 or a heavy chain of SEQ ID NO: 30 and a light chain of SEQ ID NO: 29 or a heavy chain and a light chain that has at least 60%, at least 70%, at least 80%, at least 90% or at least 95% identity to the heavy chain of SEQ ID NO: 17 or 30 and to the light chain of SEQ ID NO: 16 or 29. In another aspect said antibody is in IgG1 format. In another embodiments said $IC_{50}$ concentration is determined in a Receptor Inhibition Assay as described herein in Example 3.

In yet another embodiment the disclosed antibody or antibody fragment inhibits human IL-17C, cynomolgus monkey IL-17C and mouse IL-17C driven activation of a NF-κB reporter gene in NIH3T3 cells with an $IC_{50}$ concentration of less than 100 pM, 90 pM, 80 pM, 70 pM, 60 pM, 50 pM, 40 pM, 30 pM, 20 pM, 10 pM, 9 pM, 8 pM, 7 pM, 6 pM, 5 pM, 4 pM, 3 pM, 2 pM or 1 pM. In a preferred embodiment said antibody or antibody fragment comprises the HCDR1 region of SEQ ID NO: 7, the HCDR2 region of SEQ ID NO: 8, the HCDR3 region of SEQ ID NO: 9, the LCDR1 region of SEQ ID NO: 13, the LCDR2 region of SEQ ID NO: 14 and the LCDR3 region of SEQ ID NO: 15, or the HCDR1 region of SEQ ID NO: 10, the HCDR2 region of SEQ ID NO: 11, the HCDR3 region of SEQ ID NO: 12, the LCDR1 region of SEQ ID NO: 13, the LCDR2 region of SEQ ID NO: 14 and the LCDR3 region of SEQ ID NO: 15, or the HCDR1 region of SEQ ID NO: 20, the HCDR2 region of SEQ ID NO: 21, the HCDR3 region of SEQ ID NO: 22, the LCDR1 region of SEQ ID NO: 26, the LCDR2 region of SEQ ID NO: 27 and the LCDR3 region of SEQ ID NO: 28, or the HCDR1 region of SEQ ID NO: 23, the HCDR2 region of SEQ ID NO: 24, the HCDR3 region of SEQ ID NO: 25, the LCDR1 region of SEQ ID NO: 26, the LCDR2 region of SEQ ID NO: 27 and the LCDR3 region of SEQ ID NO: 28. In another embodiment said antibody or antibody fragment comprises a heavy chain of SEQ ID NO: 17 and a light chain of SEQ ID NO: 16 or a heavy chain of SEQ ID NO: 30 and a light chain of SEQ ID NO: 29 or a heavy chain and a light chain that has at least 60%, at least 70%, at least 80%, at least 90% or at least 95% identity to the heavy chain of SEQ ID NO: 17 or 30 and to the light chain of SEQ ID NO: 16 or 29. In another aspect said antibody is in IgG1 format. In another embodiments said $IC_{50}$ concentration is determined in a IL-17C-driven NF-κB reporter assay as described herein in Example 4.

In one embodiment the disclosed antibody or antibody fragment is specific for human IL-17C encoded by the amino acid sequence of SEQ ID NO: 1. In one embodiment the disclosed antibody or antibody fragment is specific for a polypeptide comprising the amino acid sequence of SEQ ID NO: 1. In a further embodiment said monoclonal antibody or antibody fragment is a monoclonal antibody specific for a polypeptide consisting of the amino acid sequence of SEQ ID NO: 1. In another embodiment the disclosed antibody or antibody fragment is specific for human IL-17C encoded by the amino acid sequence of SEQ ID NO: 1 and is a monoclonal antibody or antibody fragment.

In one embodiment the disclosed antibody or antibody fragment specific for IL-17C is a monoclonal antibody or antibody fragment.

In one embodiment the disclosed antibody or antibody fragment specific for IL-17C is a human, humanized or chimeric antibody. In certain embodiments, said antibody or antibody fragment specific for IL-17C is an isolated antibody or antibody fragment. In another embodiment said antibody or antibody fragment is a recombinant antibody or antibody fragment. In a further embodiment said antibody or antibody fragment is a recombinant human antibody or antibody fragment. In a further embodiment said recombinant human antibody or antibody fragment is an isolated recombinant human antibody or antibody fragment. In a further embodiment said recombinant human antibody or antibody fragment or isolated recombinant human antibody or antibody fragment is monoclonal.

In another embodiment the disclosed antibody or antibody fragment comprises a heavy chain of SEQ ID NO: 17 and a light chain of SEQ ID NO: 16 or a heavy chain of SEQ ID NO: 30 and a light chain of SEQ ID NO: 29 or a heavy chain and a light chain that has at least 60%, at least 70%, at least 80%, at least 90% or at least 95% identity to the a heavy chain of SEQ ID NO: 17 or 30 and to the light chain of SEQ ID NO: 16 or 29.

In one embodiment the disclosed antibody or antibody fragment comprises a human heavy chain constant region and a human light chain constant region. In a further embodiment said human heavy chain constant region comprises the amino acid sequences of SEQ ID NO: 17 and the human light chain constant region comprises the amino acid sequences of SEQ ID NO: 16 or said human heavy chain constant region comprises the amino acid sequences of SEQ ID NO: 30 and the human light chain constant region comprises the amino acid sequences of SEQ ID NO: 29.

In one embodiment the disclosed antibody or antibody fragment is of the IgG isotype. In another embodiment said antibody is IgG1.

In one embodiment said antibody fragment is a bivalent antibody fragment.

In another embodiment, the present disclosure refers to an antibody or antibody fragment that cross-competes with an antibody described in Table 1. In one embodiment the present disclosure refers to an antibody or antibody fragment, wherein said antibody or antibody fragment cross-competes with an antibody or antibody fragment comprising 6 CDRs defined by Kabat of one of the antibodies in Table 1. In another embodiment the present disclosure refers to an antibody or antibody fragment specific for human IL-17C wherein said antibody or antibody fragment bivalently binds to an IL-17C homodimer and forms a complex consisting of said antibody or antibody fragment and one IL-17C homodimer and wherein said antibody or antibody fragment cross-competes with an antibody or antibody fragment comprising 6 CDRs defined by Kabat of one of the antibodies in Table 1.

In another embodiment the present disclosure refers to an antibody or antibody fragment, wherein said antibody or antibody fragment cross-competes with an antibody or antibody fragment comprising 6 CDRs, wherein the HCDR1 is the amino acid sequence of SEQ ID NO: 7, the HCDR2 is the amino acid sequence of SEQ ID NO: 8, the HCDR3 is the amino acid sequence of SEQ ID NO: 9, the LCDR1 is the amino acid sequence of SEQ ID NO: 13, the LCDR2 is the amino acid sequence of SEQ ID NO: 14 and the LCDR3 is the amino acid sequence of SEQ ID NO: 15. In another embodiment the present disclosure refers to an antibody or antibody fragment, wherein said antibody or antibody fragment cross-competes with an antibody or antibody fragment comprising the VH according to SEQ ID NO: 17 and the VL according to SEQ ID NO: 16.

In another embodiment the present disclosure refers to an antibody or antibody fragment, wherein said antibody or antibody fragment cross-competes with an antibody or antibody fragment comprising 6 CDRs, wherein the HCDR1 is the amino acid sequence of SEQ ID NO: 20, the HCDR2 is the amino acid sequence of SEQ ID NO: 21, the HCDR3 is the amino acid sequence of SEQ ID NO: 22, the LCDR1 is the amino acid sequence of SEQ ID NO: 26, the LCDR2 is the amino acid sequence of SEQ ID NO: 27 and the LCDR3 is the amino acid sequence of SEQ ID NO: 28. In another embodiment the present disclosure refers to an antibody or antibody fragment, wherein said antibody or antibody fragment cross-competes with an antibody or antibody fragment comprising the VH according to SEQ ID NO: 30 and the VL according to SEQ ID NO: 29.

In another embodiment, the present disclosure refers to an antibody or antibody fragment that cross-competes with an antibody described in Table 1. In one embodiment the present disclosure refers to an antibody or antibody fragment, wherein said antibody or antibody fragment cross-competes with an antibody or antibody fragment comprising 6 CDRs defined by Chothia of one of the antibodies in Table 1. In another embodiment the present disclosure refers to an antibody or antibody fragment specific for human IL-17C wherein said antibody or antibody fragment bivalently binds to an IL-17C homodimer and forms a complex consisting of said antibody or antibody fragment and one IL-17C homodimer and wherein said antibody or antibody fragment cross-competes with an antibody or antibody fragment comprising 6 CDRs defined by Chothia of one of the antibodies in Table 1.

In another embodiment the present disclosure refers to an antibody or antibody fragment, wherein said antibody or antibody fragment cross-competes with an antibody or antibody fragment comprising 6 CDRs, wherein the HCDR1 is the amino acid sequence of SEQ ID NO: 10, the HCDR2 is the amino acid sequence of SEQ ID NO: 11, the HCDR3 is the amino acid sequence of SEQ ID NO: 12, the LCDR1 is the amino acid sequence of SEQ ID NO: 13, the LCDR2 is the amino acid sequence of SEQ ID NO: 14 and the LCDR3 is the amino acid sequence of SEQ ID NO: 15. In another embodiment the present disclosure refers to an antibody or antibody fragment, wherein said antibody or antibody fragment cross-competes with an antibody or antibody fragment comprising the VH according to SEQ ID NO: 17 and the VL according to SEQ ID NO: 18.

In another embodiment the present disclosure refers to an antibody or antibody fragment, wherein said antibody or antibody fragment cross-competes with an antibody or antibody fragment comprising 6 CDRs, wherein the HCDR1 is the amino acid sequence of SEQ ID NO: 23, the HCDR2 is the amino acid sequence of SEQ ID NO: 24, the HCDR3 is the amino acid sequence of SEQ ID NO: 25, the LCDR1 is the amino acid sequence of SEQ ID NO: 26, the LCDR2 is the amino acid sequence of SEQ ID NO: 27 and the LCDR3 is the amino acid sequence of SEQ ID NO: 28. In another embodiment the present disclosure refers to an antibody or antibody fragment, wherein said antibody or antibody fragment cross-competes with an antibody or antibody fragment comprising the VH according to SEQ ID NO: 30 and the VL according to SEQ ID NO: 29.

In a certain embodiment, the disclosure refers to an antibody or antibody fragment that cross-competes with an antibody described in Table 1 and reduces the specific binding of one of the antibodies described in Table 1 by at least 70%, 80% or 90% in an ELISA-based cross-competition assay. In a certain embodiment, the present disclosure refers to an monoclonal antibody or antibody fragment that cross-competes with an antibody described in Table 1 and reduces the specific binding of one of the antibodies described in Table 1 to IL-17C by at least 70%, 80% or 90% in an ELISA-based cross-competition assay. A representative assay set-up is illustrated in Example 6 in the present disclosure.

In another embodiment, the present disclosure refers to an antibody or antibody fragment that binds to (e.g., by binding, stabilizing, spatial distribution) the same epitope as one of the antibodies in Table 1. In a further embodiment said antibody or antibody fragment binds to (e.g., by binding, stabilizing, spatial distribution) the same epitope as an antibody or antibody fragment comprising 6 CDRs defined by Kabat of one of the antibodies in Table 1. In yet another embodiment said antibody or antibody fragment binds to (e.g., by binding, stabilizing, spatial distribution) the same epitope of IL-17C as an antibody or antibody fragment comprising 6 CDRs defined by Kabat of one of the antibodies in Table 1. In yet another embodiment said antibody or antibody fragment binds to (e.g., by binding, stabilizing, spatial distribution) the same epitope of polypeptide comprising the amino acid sequence of SEQ ID NO: 1 as an antibody or antibody fragment comprising 6 CDRs defined by Kabat of one of the antibodies in Table 1.

In another embodiment the present disclosure refers to an antibody or antibody fragment, wherein said antibody or antibody fragment binds to the same epitope as an antibody or antibody fragment comprising 6 CDRs, wherein the HCDR1 is the amino acid sequence of SEQ ID NO: 10, the HCDR2 is the amino acid sequence of SEQ ID NO: 11, the HCDR3 is the amino acid sequence of SEQ ID NO: 12, the LCDR1 is the amino acid sequence of SEQ ID NO: 13, the LCDR2 is the amino acid sequence of SEQ ID NO: 14 and the LCDR3 is the amino acid sequence of SEQ ID NO: 15. In another embodiment the present disclosure refers to an antibody or antibody fragment, wherein said antibody or antibody fragment binds to the same epitope as an antibody or antibody fragment comprising the VH according to SEQ ID NO: 17 and the VL according to SEQ ID NO: 18.

In another embodiment the present disclosure refers to an antibody or antibody fragment, wherein said antibody or antibody fragment binds to the same epitope as an antibody or antibody fragment comprising 6 CDRs, wherein the HCDR1 is the amino acid sequence of SEQ ID NO: 23, the HCDR2 is the amino acid sequence of SEQ ID NO: 24, the HCDR3 is the amino acid sequence of SEQ ID NO: 25, the LCDR1 is the amino acid sequence of SEQ ID NO: 26, the LCDR2 is the amino acid sequence of SEQ ID NO: 27 and the LCDR3 is the amino acid sequence of SEQ ID NO: 28. In another embodiment the present disclosure refers to an antibody or antibody fragment, wherein said antibody or antibody fragment binds to the same epitope as an antibody or antibody fragment comprising the VH according to SEQ ID NO: 30 and the VL according to SEQ ID NO: 29.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, epitopes are readily identified by determining spatial conformation of amino acids such as by, e.g., hydrogen/deuterium exchange, x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157:105-132; for hydropathy plots.

In one embodiment, the present disclosure refers to an antibody or antibody fragment comprising 6 CDRs defined by Kabat of any of the antibodies in Table 1. In another aspect, the disclosure pertains to an isolated monoclonal antibody or fragment thereof comprising 6 CDRs defined by Kabat of each of the antibodies in Table 1.

In another embodiment, the present disclosure refers to an antibody or antibody fragment comprising 6 CDRs defined by Chotia of any of the antibodies in Table 1. In another aspect, the disclosure pertains to an isolated monoclonal antibody or fragment thereof comprising 6 CDRs defined by Chotia of each of the antibodies in Table 1.

In certain embodiments, the present disclosure refers to the antibodies or antibody fragments disclosed in in Table 1, wherein said antibodies or antibody fragments can bind to IL-17C with an affinity of about less than 100 nM, more preferably less than about 60 nM, and still more preferably less than about 30 nM. Further preferred are antibodies or antibody fragments that bind to IL-17C with an affinity of less than about 10 nM, and more preferably less than about 3 nM.

In certain embodiments, the present disclosure refers to the antibodies or antibody fragments disclosed in Table 1, wherein said antibodies or antibody fragments can bind to IL-17C with a monovalent affinity of about less than 100 nM, more preferably less than about 60 nM, and still more preferably less than about 30 nM. Further preferred are antibodies or antibody fragments that bind to IL-17C with a monovalent affinity of less than about 10 nM, and more preferably less than about 3 nM.

In another embodiment, the present disclosure refers to antibodies or antibody fragments specific for IL-17C, wherein said antibodies or antibody fragments have a monovalent affinity to IL-17C with a dissociation rate constant ($K_D$) of less than $5 \times 10^{-2}$M, less than $10^{-2}$M, less than $5 \times 10^{-3}$M, less than $10^{-3}$M, less than $5 \times 10^{-4}$M, less than $10^{-4}$M, less than $5 \times 10^{-5}$M, less than $10^{-5}$M, less than $5 \times 10^{-6}$M, less than $10^{-6}$M, less than $5 \times 10^{-7}$M, less than $10^{-7}$M, less than $5 \times 10^{-8}$M, less than $10^{-8}$M, less than $5 \times 10^{-9}$M, less than $10^{-9}$M, less than $5 \times 10^{-10}$M, less than $10^{-10}$M, less than $5 \times 10^{-11}$M, less than $10^{-11}$M, less than $5 \times 10^{-12}$M, less than $10^{-12}$M, less than $5 \times 10^{-13}$M, less than $10^{-13}$M, less than $5 \times 10^{-14}$M, less than $10^{-14}$M, less than $5 \times 10^{-15}$M, or less than $10^{-15}$M and wherein said antibodies or antibody fragments in a bivalent format have an affinity to IL-17C with a dissociation rate constant ($K_D$) which is at least 2-fold, 5-fold, 10-fold, 100-fold, 1000-fold, 10000-fold, 100000-fold lower than the dissociation rate constant (KD) in a monovalent format. In a further embodiment the bivalent affinity of said antibodies or antibody fragments is determined in IgG-format, wherein the monovalent affinity of said antibodies or antibody fragments is determined in Fab-format.

The compositions of the present disclosure are preferably pharmaceutical compositions comprising an antibody or antibody fragment specific for IL-17C as disclosed herein and a pharmaceutically acceptable carrier, diluent or excipient, for the treatment of an inflammatory disorder or cancer. Such carriers, diluents and excipients are well known in the art, and the skilled artisan will find a formulation and a route of administration best suited to treat a subject with the IL-17C antibodies or antibody fragments of the present disclosure.

In another embodiment the present disclosure refers to pharmaceutical compositions comprising an antibody or antibody fragment specific for IL-17C as disclosed herein for the use in the treatment of a disorder or condition associated with the undesired presence of IL-17C. In another embodiment said condition associated with the undesired presence of IL-17C is an inflammatory disorder or cancer. In another embodiment said inflammatory disorder is rheumatoid arthritis, psoriasis, pulmonary inflammation, COPD and/or atopic dermatitis (AD), including moderate-to-severe AD. In a preferred embodiment said inflammatory disorder is atopic dermatitis (AD) and/or moderate-to-severe AD.

In another embodiment the present disclosure refers to the use of said pharmaceutical compositions comprising an antibody or antibody fragment specific for IL-17C as disclosed herein in the preparation of a medicament for the treatment of a disorder or condition associated with the undesired presence of IL-17C. In another embodiment said condition associated with the undesired presence of IL-17C is an inflammatory disorder or cancer. In another embodiment said inflammatory disorder is rheumatoid arthritis, psoriasis, pulmonary inflammation, COPD and/or atopic dermatitis (AD), including moderate-to-severe AD. In a preferred embodiment said inflammatory disorder is atopic dermatitis (AD) and/or moderate-to-severe AD.

In another embodiment the present disclosure refers to the use of said pharmaceutical composition for the treatment of a disorder or condition associated with the undesired presence of IL-17C. In another embodiment said condition associated with the undesired presence of IL-17C is an inflammatory disorder or cancer. In another embodiment said inflammatory disorder is rheumatoid arthritis, psoriasis, pulmonary inflammation, COPD and/or atopic dermatitis (AD), including moderate-to-severe AD. In a preferred embodiment said inflammatory disorder is atopic dermatitis (AD) and/or moderate-to-severe AD.

In another aspect, provided herein is a method of treating atopic dermatitis (AD) and/or moderate-to-severe atopic dermatitis (AD) in a subject, the method comprising administering a pharmaceutical composition comprising a therapeutically effective amount of the IL-17C antibodies or antibody fragments of the present disclosure. In one embodiment said subject is resistant, non-responsive or inadequately responsive to treatment by either a topical corticosteroid (TCS) or a calcineurin inhibitor. In another embodiment the subject is a subject in need thereof. In a preferred embodiment said subject is a human. In alternative aspects said subject is a rodent, such as a rat or a mouse.

In another embodiment, the present disclosure refers to a method for the prophylaxis of an inflammatory disorder in a subject, said method comprising administering an IL-17C antagonist to said subject. "Prophylaxis" as used in this context refers to methods which aim to prevent the onset of a disease or which delay the onset of a disease. In some embodiments said subject is a human. In alternative aspects said subject is a rodent, such as a rat or a mouse.

In some embodiments, the antibodies or antibody fragments specific for IL-17C of the present disclosure are administered subcutaneously. In other aspects the antibodies or antibody fragments specific for IL-17C of the present disclosure are administered intra-venously, intra-articularly or intra-spinally.

In one embodiment, the disclosure pertains to an isolated monoclonal antibody or fragment thereof comprising a VH and a VL of any of the antibodies in Table 1.

In another embodiment, the disclosure pertains to an isolated monoclonal antibody or fragment thereof comprising a Heavy chain (IgG1) and a Light chain of any of the antibodies in Table 1.

In another embodiment, the disclosure refers to an isolated nucleic acid encoding a heavy chain sequence and/or light chain sequence of an antibody that binds to IL-17C the nucleic acid comprising a HCDR1 region of SEQ ID NO: 58, the HCDR2 region of SEQ ID NO: 59, the HCDR3 region of SEQ ID NO: 60, the LCDR1 region of SEQ ID NO: 64, the LCDR2 region of SEQ ID NO: 65 and the LCDR3 region of SEQ ID NO: 66, or a HCDR1 region of SEQ ID NO: 61, the HCDR2 region of SEQ ID NO: 62, the HCDR3 region of SEQ ID NO: 63, the LCDR1 region of SEQ ID NO: 64, the LCDR2 region of SEQ ID NO: 65 and the LCDR3 region of SEQ ID NO: 66, or a HCDR1 region of SEQ ID NO: 33, the HCDR2 region of SEQ ID NO: 34, the HCDR3 region of SEQ ID NO: 35, the LCDR1 region of SEQ ID NO: 39, the LCDR2 region of SEQ ID NO: 40 and the LCDR3 region of SEQ ID NO: 41, or a HCDR1 region of SEQ ID NO: 36, the HCDR2 region of SEQ ID NO: 37, the HCDR3 region of SEQ ID NO: 38, the LCDR1 region of SEQ ID NO: 39, the LCDR2 region of SEQ ID NO: 40 and the LCDR3 region of SEQ ID NO: 41, or a HCDR1 region of SEQ ID NO: 46, the HCDR2 region of SEQ ID NO: 47, the HCDR3 region of SEQ ID NO: 48, the LCDR1 region of SEQ ID NO: 52, the LCDR2 region of SEQ ID NO: 53 and the LCDR3 region of SEQ ID NO: 54, or a HCDR1 region of SEQ ID NO: 49, the HCDR2 region of SEQ ID NO: 50, the HCDR3 region of SEQ ID NO: 51, the LCDR1 region of SEQ ID NO: 52, the LCDR2 region of SEQ ID NO: 53 and the LCDR3 region of SEQ ID NO: 54.

In another embodiment, the disclosure refers to a nucleic acid encoding an isolated monoclonal antibody or fragment thereof wherein the nucleic acid comprises a VH region of SEQ ID NO: 19 and a VL region of SEQ ID NO: 18, or a VH region and a VL region that has at least 60%, at least 70%, at least 80%, at least 90% or at least 95% identity to the VH region of SEQ ID NO: 19 and/or the VL region of SEQ ID NO: 18.

In another embodiment, the disclosure refers to a nucleic acid encoding an isolated monoclonal antibody or fragment thereof wherein the nucleic acid comprises a VH region of SEQ ID NO: 68 and a VL region of SEQ ID NO: 67, or a VH region and a VL region that has at least 60%, at least 70%, at least 80%, at least 90% or at least 95% identity to the VH region of SEQ ID NO: 68 and/or the VL region of SEQ ID NO: 67.

In another embodiment, the disclosure refers to a nucleic acid encoding an isolated monoclonal antibody or fragment thereof wherein the nucleic acid comprises a VH region of SEQ ID NO: 32 and a VL region of SEQ ID NO: 31, or a VH region and a VL region that has at least 60%, at least 70%, at least 80%, at least 90% or at least 95% identity to the VH region of SEQ ID NO: 32 and/or the VL region of SEQ ID NO: 31

In another embodiment, the disclosure refers to a nucleic acid encoding an isolated monoclonal antibody or fragment thereof wherein the nucleic acid comprises a Heavy chain (IgG1) of SEQ ID NO: 45 and a Light chain of SEQ ID NO: 44.

In another embodiment, the disclosure refers to a nucleic acid encoding an isolated monoclonal antibody or fragment thereof wherein the nucleic acid comprises a Heavy chain (IgG1) of SEQ ID NO: 70 and a Light chain of SEQ ID NO: 69.

In another embodiment, the disclosure refers to a nucleic acid encoding an isolated monoclonal antibody or fragment thereof wherein the nucleic acid comprises a Heavy chain (IgG1) of SEQ ID NO: 71 and a Light chain of SEQ ID NO: 57.

In another embodiment, the disclosure refers to a nucleic acid encoding an isolated monoclonal antibody or fragment thereof wherein the nucleic acid comprises a VH and a VL of any of the antibodies in Table 1.

In another embodiment, the disclosure refers to a nucleic acid encoding an isolated monoclonal antibody or fragment thereof wherein the nucleic acid comprises a Heavy chain (IgG1) and a Light chain of any of the antibodies in Table 1.

In another embodiment, the disclosure refers to a method of producing an isolated monoclonal antibody or fragment thereof of any of the antibodies in Table 1.

TABLE 1

Antibody sequences

| Antibody # | | SEQ ID NO: | [aa]/DNA |
|---|---|---|---|
| MAB#1 | HCDR1(Kabat) | SEQ ID NO: 7 | DYAMH |
| | HCDR2(Kabat) | SEQ ID NO: 8 | YIGGVGEGTQYAESVKG |
| | HCDR3(Kabat) | SEQ ID NO: 9 | GFAIRYYGFDY |
| | HCDR1(Chothia) | SEQ ID NO: 10 | GFTVSDY |
| | HCDR2(Chothia) | SEQ ID NO: 11 | GGVGEG |
| | HCDR3(Chothia) | SEQ ID NO: 12 | GFAIRYYGFDY |
| | LCDR1(Kabat & Chothia) | SEQ ID NO: 13 | SGDKLGDKYAY |
| | LCDR2(Kabat & Chothia) | SEQ ID NO: 14 | QDSKRPS |
| | LCDR3(Kabat & Chothia) | SEQ ID NO: 15 | QVFTFPLVTT |
| | VL | SEQ ID NO: 16 | SYELTQPPSVSVSPGQTASITCSGDKLGDKYAYW YQQKPGQSPVLVIYQDSKRPSGIPERFSGSNSGN TATLTISGTQAEDEADYYCQVFTFPLVTTVFGGGT KLTVLGQ |
| | VH | SEQ ID NO: 17 | EVQLLESGGGLVQPGGSLRLSCAASGFTVSDYAM HWVRQAPGKGLEWVSYIGGVGEGTQYAESVKGR FTISRDNSKNTLYLQMNSLRAEDTAVYYCARGFAI RYYGFDYWGQGTLVTVSS |
| | VL(DNA) | SEQ ID NO: 18 | agctatgaactgacccagccgccgagcgttagcgttagcccaggcca gaccgccagcattacctgtagcggcgacaaactgggcgacaaatac gcctactggtatcagcagaaaccgggccagagcccggtgctggttatc tatcaggatagcaaacgcccgagcggcattccagaacgctttagcgg cagcaacagcggcaacaccgccaccctgaccattagcggcaccca ggccgaagacgaagccgattattactgccaggttttcactttcccgctgg ttactactgtgtttggcggcggtaccaagctgaccgtgctgggccag |
| | VH(DNA) | SEQ ID NO: 19 | gaagtgcagctgctggaaagcggtggcggtctggtgcagccaggtgg tagcctgcgcctgagctgtgccgcaagcggcttcacagtgtccgacta cgcaatgcattgggtgcgccaagcaccaggcaaaggcctggaatgg gtgagttacataggtggcgtgggtgaggggacacaatatgcagagag cgtgaaaggtcgctttaccattagtcgcgataacagcaaaaacaccct gtatctgcaaatgaacagcctgcgggcagaagataccgcagtttattat tgcgcgcgtggtttcgcaatccgttattatggatttgattattggggccagg gcaccctggttactgtctcgagc |
| | HCDR1(Kabat) | SEQ ID NO: 33 | gactacgcaatgcat |
| | HCDR2(Kabat) | SEQ ID NO: 34 | tacataggtggcgtgggtgaggggacacaatatgcagagagcgtga aaggt |
| | HCDR3(Kabat) | SEQ ID NO: 35 | ggtttcgcaatccgttattatggatttgattat |
| | HCDR1(Chothia) | SEQ ID NO: 36 | ggcttcacagtgtccgactac |

TABLE 1-continued

Antibody sequences

| Antibody # | | SEQ ID NO: | [aa]/DNA |
|---|---|---|---|
| | HCDR2 (Chothia) | SEQ ID NO: 37 | ggtggcgtgggtgagggg |
| | HCDR3 (Chothia) | SEQ ID NO: 38 | ggtttcgcaatccgttattatggatttgattat |
| | LCDR1 (Kabat & Chothia) | SEQ ID NO: 39 | agcggcgacaaactgggcgacaaatacgcctac |
| | LCDR2 (Kabat & Chothia) | SEQ ID NO: 40 | caggatagcaaacgcccgagc |
| | LCDR3 (Kabat & Chothia) | SEQ ID NO: 41 | caggttttcactttcccgctggttactact |
| | Light chain | SEQ ID NO: 42 | SYELTQPPSVSVSPGQTASITCSGDKLGDKYAYW YQQKPGQSPVLVIYQDSKRPSGIPERFSGSNSGN TATLTISGTQAEDEADYYCQVFTFPLVTTVFGGGT KLTVLGQPKAAPSVTLFPPSSEELQANKATLVCTTS DFYPGAVTVAWKADSSPVKAGVETTTPSKQSNNK YAASSYLSLTPEQWKSHRSYSCQVTHEGSTVEKT VAPTECS |
| | Heavy chain (IgG1) | SEQ ID NO: 43 | EVQLLESGGGLVQPGGSLRLSCAASGFTVSDYAM HWVRQAPGKGLEWVSYIGGVGEGTQYAESVKGR FTISRDNSKNTLYLQMNSLRAEDTAVYYCARGFAI RYYGFDYWGQGTLVTVSSASTKGPSVFPLAPSSK STSGGTAALGCLVKDYFPEPVTVSWNSGALTSGV HTFPAVLQSSGLYSLSSVVTVPSSSLGTQTYICNV NHKPSNTKVDKRVEPKSCDKTHTCPPCPAPELLG GPSVFLFPPKPKDTLMISRTPEVTCVVVDVSHEDP EVKFNWYVDGVEVHNAKTKPREEQYNSTYRVVSV LTVLHQDWLNGKEYKCKVSNKALPAPIEKTISKAK GQPREPQVYTLPPSREEMTKNQVSLTCLVKGFYP SDIAVEWESNGQPENNYKTTPPVLDSDGSFFLYS KLTVDKSRWQQGNVFSCSVMHEALHNHYTQKSL SLSPGK |
| | Light chain(DNA) | SEQ ID NO: 44 | agctatgaactgacccagccgccgagcgttagcgttagcccaggcca gaccgccagcattacctgtagcggcgacaaactgggcgacaaatac gcctactggtatcagcagaaaccgggccagagcccggtgctggttatc tatcaggatagcaaacgcccgagcggcattccagaacgctttagcgg cagcaacagcggcaacaccgccaccctgaccattagcggcaccca ggccgaagacgaagccgattattactgccaggttttcactttcccgctgg ttactactgtgtttggcggcggtaccaagctgaccgtgctgggccagcc caaaagccgccctagcgtgaccctgttcccccccaagcagcgaggaa ctccaggccaacaaggccaccctcgtgtgcctgatcagcgacttctac cctggcgccgtgaccgtggcctggaaggccgatagcagccctgtgaa ggccggcgtggaaaccaccacccccagcaagcagagcaacaaca atacgccgccagcagctacctgagcctgaccccgagcagtggaa gtcccacagatcctacagctgccaggtcacacacgagggcagcacc gtggaaaagaccgtggcccccaccgagtgcagc |
| | Heavy chain (IgG1, DNA) | SEQ ID NO: 45 | gaagtgcagctgctggaaagcggtggcggtctggtgcagccaggtgg tagcctgcgcctgagctgtgccgcaagcggcttcacagtgtccgacta cgcaatgcattgggtgcgccaagcaccaggcaaaggcctggaatgg gtgagttacataggtggcgtgggtgagggggacaatatgcagagag cgtgaaaggtcgctttaccattagtcgcgataacagcaaaaacaccct gtatctgcaaatgaacagcctgcgggcagaagataccgcagtttattat tgcgcgcgtggtttcgcaatccgttattatggatttgattattggggccagg gcaccctggttactgtctcgagcgcgtcgaccaaaggccccagcgtgt tccctctggccccagcagcaagagcacctctggcgcggaacagccgc cctgggctgcctggtcaaggactacttccccgagcccgtgaccgtgtc ctggaactctggcgccctgaccagcggcgtgcacaccttccagccgtg ctccagagcagcggcctgtacagcctgagcagcgtcgtgaccgtgcc cagcagcagcctgggcacccagacctacatctgcaacgtgaaccac aagcccagcaacacaaaggtggacaagcgggtggaacccaagag ctgcgacaagacccacacctgtcccccctgccctgccctgaactgct gggaggcccctccgtgttcctgttccccccaaagcctaaggacaccct gatgatcagccggaccccgaagtgacctgcgtggtggtggacgtgt cccacgaggaccctgaagtgaagtttaattggtacgtggacggcgtgg aagtgcacaacgccaagaccaagccagagaggaacagtacaac agcacctaccgggtggtgtccgtgctgaccgtgctgcaccaggactgg ctgaacggcaaagagtacaagtgcaaggtgtccaacaaggcctgc ctgcccccatcgagaaaaccatcagcaaggccaaaggccagcccc gcgagccccaggtgtacacactgcccctagcccgggaagagatgac |

TABLE 1-continued

Antibody sequences

| Antibody # | | SEQ ID NO: | [aa]/DNA |
|---|---|---|---|
| | | | caagaaccaggtgtccctgacctgcctcgtgaagggcttctaccccag cgacattgccgtggaatgggagagcaacggccagcccgagaacaa ctacaagaccacccccctgtgctggacagcgacggctcattcttcctg tacagcaagctgaccgtggacaagagccggtggcagcagggcaac gtgttcagctgctccgtgatgcacgaggccctgcacaaccactacacc cagaagtccctgagcctgagccccggcaag |
| DNA(optimized) HCDR1(Kabat) | | SEQ ID NO: 58 | gactacgctatgcac |
| HCDR2(Kabat) | | SEQ ID NO: 59 | tatatcggcggcgtgggcgagggcacccagtacgctgagtctgtgaa gggc |
| HCDR3(Kabat) | | SEQ ID NO: 60 | ggcttcgccatccggtactacggcttcgactac |
| HCDR1(Chothia) | | SEQ ID NO: 61 | ggcttcaccgtgtccgactac |
| HCDR2(Chothia) | | SEQ ID NO: 62 | ggcggcgtgggcgagggc |
| HCDR3(Chothia) | | SEQ ID NO: 63 | ggcttcgccatccggtactacggcttcgactac |
| LCDR1(Kabat & Chothia) | | SEQ ID NO: 64 | tccggcgacaagctgggcgataagtacgcctac |
| LCDR2(Kabat & Chothia) | | SEQ ID NO: 65 | caggactccaagcggccctcc |
| LCDR3(Kabat & Chothia) | | SEQ ID NO: 66 | caggtgttcaccttccccctggtcaccacc |
| VL(DNA) | | SEQ ID NO: 67 | tcctacgagctgacccagccccctcgtgtccgtgtctcctggccaga ccgcctccatcacctgttccggcgacaagctgggcgataagtacgcct actggtatcagcagaagcccggccagtcccccgtgctggtcatctacc aggactccaagcggccctccggcatccctgagcggttctccggctcca actccggcaacaccgccaccctgaccatctccggcacccaggccga ggacgaggccgactactactgccaggtgttcaccttccccctggtcacc accgtgttcggcggaggcaccaagctgaccgtgctgggccag |
| VH(DNA) | | SEQ ID NO: 68 | gaggtgcagctgctggaatccggcggaggactggtgcagcctggcg gctcccctgagactgtcttgcgccgcctccggcttcaccgtgtccgactac gctatgcactgggtccgacaggcccctggcaagggcctggaatgggt gtcctatatcggcggcgtgggcgagggcacccagtacgctgagtctgt gaagggccggttcaccatctcccgggacaactccaagaacaccctgt acctgcagatgaactccctgcgggccgaggacaccgccgtgtactac tgtgccagaggcttcgccatccggtactacggcttcgactactggggcc agggcaccctggtcaccgtgtctagc |
| Light chain(DNA) | | SEQ ID NO: 69 | tcctacgagctgacccagccccctcgtgtccgtgtctcctggccaga ccgcctccatcacctgttccggcgacaagctgggcgataagtacgcct actggtatcagcagaagcccggccagtcccccgtgctggtcatctacc aggactccaagcggccctccggcatccctgagcggttctccggctcca actccggcaacaccgccaccctgaccatctccggcacccaggccga ggacgaggccgactactactgccaggtgttcaccttccccctggtcacc accgtgttcggcggaggcaccaagctgaccgtgctgggccagcctaa ggccgctcccctcgtgaccctgttccccccatcctccgaggaactgca ggccaacaaggccaccctggtctgcctgatctccgacttctaccctggc gccgtgaccgtggcctggaaggccgacagctctcctgtgaaggccgg cgtggaaaccaccacccccctccaagcagtccaacaacaaatacgcc gcctcctcctacctgtccctgacccccgagcagtggaagtcccaccgg tcctacagctgccaggtcacacacgagggcctccaccgtgaaaaga ccgtggcccctaccgagtgctcc |
| Heavy chain (IgG1, DNA) | | SEQ ID NO: 70 | gaggtgcagctgctggaatccggcggaggactggtgcagcctggcg gctcccctgagactgtcttgcgccgcctccggcttcaccgtgtccgactac gctatgcactgggtccgacaggcccctggcaagggcctggaatgggt gtcctatatcggcggcgtgggcgagggcacccagtacgctgagtctgt gaagggccggttcaccatctcccgggacaactccaagaacaccctgt acctgcagatgaactccctgcgggccgaggacaccgccgtgtactac tgtgccagaggcttcgccatccggtactacggcttcgactactggggcc agggcaccctggtcaccgtgtctagcgcctccaccaagggcccctcc gtgttccctctggcccctcagcaagtccacctctggcggcacagcctg ccctgggctgcctggtcaaggactacttccccgagcccgtgaccgtgtc ctgaactctggcgccctgacctccggcgtgcacaccttccctgccgtg ctgcagtcctccggcctgtactccctgtcctccgtcgtgaccgtgccctcc agctctctgggcacccagacctacatctgcaacgtgaaccacaagcc ctccaacaccaaggtggacaagcgggtggaacccaagtcctgcgac |

TABLE 1-continued

Antibody sequences

| Antibody # | | SEQ ID NO: | [aa]/DNA |
|---|---|---|---|
| | | | aagacccacacctgtccccctgccctgccctgaactgctgggcgg
accttccgtgttcctgttccccccaaagcccaaggacaccctgatgatct
cccggaccccgaagtgacctgcgtggtggtggacgtgtcccacgag
gaccctgaagtgaagttcaattggtacgtggacggcgtggaagtgcac
aacgccaagaccaagcccagagaggaacagtacaactccacctac
cgggtggtgtccgtgctgaccgtgctgcaccaggactggctgaacggc
aaagagtacaagtgcaaggtgtccaacaaggccctgcctgccccat
cgaaaagaccatctccaaggccaagggccagccccgcgagccca
ggtgtacacactgccccctagccgggaagagatgaccaagaaccag
gtgtccctgacctgtctggtcaagggcttctacccctccgacattgccgt
ggaatgggagtccaacggccagcccgagaacaactacaagaccac
cccccctgtgctggactccgacggctcattcttcctgtactccaagctga
ccgtggacaagtcccggtggcagcagggcaacgtgttctcctgctccg
tgatgcacgaggccctgcacaaccactacacccagaagtccctgtcc
ctgagccccggcaag |
| MAB#2 | HCDR1(Kabat) | SEQ ID NO: 20 | SDHYIS |
| | HCDR2(Kabat) | SEQ ID NO: 21 | YISSSGSTTYYAESVKG |
| | HCDR3(Kabat) | SEQ ID NO: 22 | QSYYFLPYFDV |
| | HCDR1(Chothia) | SEQ ID NO: 23 | GFTFSDH |
| | HCDR2(Chothia) | SEQ ID NO: 24 | SSSGST |
| | HCDR3(Chothia) | SEQ ID NO: 25 | QSYYFLPYFDV |
| | LCDR1(Kabat & Chothia) | SEQ ID NO: 26 | TGTSSDVGSYNLVS |
| | LCDR2(Kabat & Chothia) | SEQ ID NO: 27 | EGSKRPS |
| | LCDR3(Kabat & Chothia) | SEQ ID NO: 28 | ASRGSRRVLYV |
| | VL | SEQ ID NO: 29 | QSALTQPASVSGSPGQSITISCTGTSSDVGSYNLV
SWYQQHPGKAPKLMIYEGSKRPSGVSNRFSGSK
SGNTASLTISGLQAEDEADYYCASRGSRRVLYVFG
GGTKLTVLGQ |
| | VH | SEQ ID NO: 30 | QVQLVESGGGLVKPGGSLRLSCAASGFTFSDHYI
SWIRQAPGKGLEWVSYISSSGSTTYYAESVKGRF
TISRDNAKNSLYLQMNSLRAEDTAVYYCARQSYYF
LPYFDVWGQGTLVTVSS |
| | VL(DNA) | SEQ ID NO: 31 | cagagcgcccctgacccagccagccagcgttagcggtagcccaggcc
agagcattaccattagctgcaccggcaccagcagcgacgtgggcag
ctataaccttggttagcagcatccgggcaaagcccgaa
actgatgatctatgaaggcagcaaacgcccgagcggcgttagcaac
cgctttagtggcagcaaaagcggcaacaccgccagcctgaccattag
cggcctgcaagccgaagacgaagccgattattactgcgcaagtcgg
ggaagccgtcgtgtgctgtatgtttttggcggcggtaccaagctgaccgt
gctgggccag |
| | VH(DNA) | SEQ ID NO: 32 | caggtgcagctggtggaaagcggcggtggcctggtgaaaccaggcg
gtagcctgcgcctgagctgcgccgccagcggctttacctttagcgatca
ttacattagctggattcgccaggcccaggcaaaggcctggaatgggt
tagctatattagcagcagtggcagcaccacctattacgccgagagcgt
gaaaggccgctttaccattagccgcgataacgccaaaaacagcctgt
atctgcaaatgaacagcctgcgggccgaagataccgccgtgtattatt
gcgcgcgacaatcctactatttcctgccttatttcgacgtttggggccagg
gcaccctggttactgtctcgagc |
| | HCDR1(Kabat) | SEQ ID NO: 46 | agcgatcattacattagc |
| | HCDR2(Kabat) | SEQ ID NO: 47 | tatattagcagcagtggcagcaccacctattacgccgagagcgtgaa
aggc |
| | HCDR3(Kabat) | SEQ ID NO: 48 | caatcctactatttcctgccttatttcgacgtt |
| | HCDR1(Chothia) | SEQ ID NO: 49 | ggctttacctttagcgatcat |
| | HCDR2(Chothia) | SEQ ID NO: 50 | agcagcagtggcagcacc |

TABLE 1-continued

Antibody sequences

| Antibody # | | SEQ ID NO: | [aa]/DNA |
|---|---|---|---|
| | HCDR3 (Chothia) | SEQ ID NO: 51 | caatcctactatttcctgccttatttcgacgtt |
| | LCDR1 (Kabat & Chothia) | SEQ ID NO: 52 | accggcaccagcagcgacgtgggcagctataacctggttagc |
| | LCDR2 (Kabat & Chothia) | SEQ ID NO: 53 | gaaggcagcaaacgcccgagc |
| | LCDR3 (Kabat & Chothia) | SEQ ID NO: 54 | gcaagtcggggaagccgtcgtgtgctgtatgtt |
| | Light chain | SEQ ID NO: 55 | QSALTQPASVSGSPGQSITISCTGTSSDVGSYNLV SWYQQHPGKAPKLMIYEGSKRPSGVSNRFSGSK SGNTASLTISGLQAEDEADYYCASRGSRRVLYVFG GGTKLTVLGQPKAAPSVTLFPPSSEELQANKATLV CTTSDFYPGAVTVAWKADSSPVKAGVETTTPSKQS NNKYAASSYLSLTPEQWKSHRSYSCQVTHEGSTV EKTVAPTECS |
| | Heavy chain (IgG1) | SEQ ID NO: 56 | QVQLVESGGGLVKPGGSLRLSCAASGFTFSDHYI SWIRQAPGKGLEWVSYISSSGSTTYYAESVKGRF TISRDNAKNSLYLQMNSLRAEDTAVYYCARQSYYF LPYFDWVGQGTLVTVSSASTKGPSVFPLAPSSKS TSGGTAALGCLVKDYFPEPVTVSWNSGALTSGVH TFPAVLQSSGLYSLSSVVTVPSSSLGTQTYICNVN HKPSNTKVDKRVEPKSCDKTHTCPPCPAPELLGG PSVFLFPPKPKDTLMISRTPEVTCVVVDVSHEDPE VKFNWYVDGVEVHNAKTKPREEQYNSTYRVVSVL TVLHQDWLNGKEYKCKVSNKALPAPIEKTISKAKG QPREPQVYTLPPSREEMTKNQVSLTCLVKGFYPS DIAVEWESNGQPENNYKTTPPVLDSDGSFFLYSKL TVDKSRWQQGNVFSCSVMHEALHNHYTQKSLSL SPGK |
| | Light chain (DNA) | SEQ ID NO: 57 | cagagcgccctgacccagccagccagcgttagcggtagcccaggcc agagcattaccattagctgcaccggcaccagcagcgacgtgggcag ctataacctggttagctggtatcagcagcatccgggcaaagccccgaa actgatgatctatgaaggcagcaaacgcccgagcggcgttagcaac cgctttagtggcagcaaaagcggcaacaccgccagcctgaccattag cggcctgcaagccgaagacgaagccgattattactgcgcaagtcgg ggaagccgtcgtgtgctgtatgtttttggcggcggtaccaagctgaccgt gctgggccagcccaaagccgcccctagcgtgaccctgttccccccaa gcagcgaggaactccaggccaacaaggccacccttcgtgtgcctgat cagcgacttctaccctggcgccgtgaccgtggcctggaaggccgata gcagccctgtgaaggccggcgtggaaaccaccaccccccagcaagc agagcaacaacaaatacgccgccagcagctacctgagcctgaccc ccgagcagtggaagtcccacagatcctacagctgccaggtcacaca cgagggcagcaccgtggaaaagaccgtggccccccaccgagtgcag c |
| | Heavy chain (DNA, IgG1) | SEQ ID NO: 71 | caggtgcagctggtggaaagcggcggtggcctggtgaaaccaggcg gtagcctgcgcctgagctgcgccgccagcggctttacctttagcgatca ttacattagctggattcgccaggcccaggcaaaggcctggaatgggt tagctatattagcagcagtggcagcaccacctattacgccgagagcgt gaaaggccgctttaccattagccgcgataacgccaaaaacagcctgt atctgcaaatgaacagcctgcgggccgaagataccgccgtgtattatt gcgcgcgacaatcctactatttcctgccttatttcgacgtttggggccagg gcaccctggttactgtctcgagcgcgtcgaccaaaggcccagcgtgt tccctctggccccagcagcaagagcacctctggcggaacagccgc cctgggctgcctggtcaaggactacttccccgagcccgtgaccgtgtcc tggaactctggcgcccctgaccagcggcgtgcacaccttccagccgtg ctccagagcagcggcctgtacagcctgagcagcgtcgtgaccgtgcc cagcagcagcctgggcacccagacctacatctgcaacgtgaaccac aagcccagcaacacaaaggtggacaagcgggtggaacccaagag ctgcgacaagacccacacctgtcccccctgccctgccccctgaactgct gggaggcccctcgtgttcctgttccccccaaagcctaaggacaccct gatgatcagccggaccccgaagtgacctgcgtggtggtggacgtgt cccacgaggaccctgaagtgaagtttaattggtacgtggacggcgtgg aagtgcacaacgccaagaccaagccccagagaggaacagtacaac agcacctaccgggtggtgtccgtgctgaccgtgctgcaccaggactgg ctgaacggcaaagagtacaagtgcaaggtgtccaacaaggccctgc ctgcccccatcgagaaaaccatcagcaaggccaaggccagccccc gcgagccccaggtgtacacactgcccccctagccgggaagagatgac caagaaccaggtgtccctgacctgcctcgtgaagggcttctaccccag |

TABLE 1-continued

Antibody sequences

| Antibody # | SEQ ID NO: | [aa]/DNA |
|---|---|---|
| | | cgacattgccgtggaatgggagagcaacggccagcccgagaacaa |
| | | ctacaagaccacccccctgtgctggacagcgacggctcattcttcctg |
| | | tacagcaagctgaccgtggacaagagccggtggcagcagggcaac |
| | | gtgttcagctgctccgtgatgcacgaggccctgcacaaccactacacc |
| | | cagaagtccctgagcctgagccccggcaag |

WORKING EXAMPLES

List of Abbreviations

ANOVA analysis of variance
BSA bovine serum albumin
BW body weight
CDR Complementarity determining region
DLS Dynamic Light Scattering
DMEM Dulbecco's Modified Eagle Medium
$EC_{50}$ 50% effective concentration
ECD extracellular domain
ECL electrochemiluminescence
ELISA enzyme-linked immunosorbent assay
EtOH Ethanol
Fab antigen-binding fragment
FBS Foetal Bovine Serum
Fc constant fragment
HPLC High Performance Liquid Chromatography
i.p. intraperitoneal(ly)
i.v. intravenous(ly)
$IC_{50}$ 50% inhibitory concentration
IFN-γ Interferon-gamma
Ig immunoglobulin
IHC immunohistochemistry
IL-17R interleukin 17 receptor
IL-xx interleukin xx
$K_D$ dissociation constant
MC903 calcipotriol
MPEK mouse primary keratinocytes
mRNA messenger ribonucleic acid
NF-κB nuclear factor kappa B
p.o. per os, oral(ly)
PBS phosphate buffered saline
qPCR quantitative polymerase chain reaction
qRT-PCR quantitative real-time polymerase chain reaction
SEM standard error of the mean
Th2 Type 2 helper T cells

Example 1

Generation of Antigen, Fab Fragments and Antibodies 1.1 Antigen Generation and Quality Control Amino acid sequences of IL-17C from human, cynomolgus monkey and mouse, were aligned.

Without leader sequence, homology of 79% is shared among all three species.

| | Human | Cynomolgus | Mouse |
|---|---|---|---|
| Human | 100% | 95% | 79% |
| Cynomolgus | | 100% | 79% |
| Mouse | | | 100% |

IL-17C form different species was purchased from different providers or produced in-house and solubilised, if necessary. Per 100 μg protein 4 μl biotinylation reagent of the ECL™ biotinylation module were added and incubated for 60 min at room temperature in the dark with gentle agitation. Subsequently biotinylated protein was purified using Zeba™ Desalt spin columns and OD280nm was determined.

Antigens were biotinylated by using the ECL™ biotinylation module (GE Healthcare; #1061918). After biotinlyation the product was purified using Zeba™ Desalt spin columns (Pierce; #89889).

Biotinylated and non-biotinylated mouse, cynomolgus and human IL-17C were subjected to a quality control comprising analyses under denaturing, reducing and denaturing, non-reducing conditions in SDS-PAGE and in native state by High Pressure-Size Exclusion Chromatography (HP-SEC) and Dynamic Light Scattering (DLS).

HP-SEC was performed on a Dionex UltiMate 3000 Titanium HPLC system (Dionex Corporation, Germering, Germany) in combination with Wyatt miniDAWN Treos and Wyatt Optilab rEX (Wyatt Technology Europe, Dernbach, Germany). For separation a Tosoh TSK-Gel G3000SWxl column was used (Tosoh Bioscience, Stuttgart, Germany). For each sample 15 μg of protein was loaded onto the column, separation was performed at a flow rate of 0.5 ml/min and recorded analyzing the UV absorption at 280 nm. The running buffer was composed of 49 mM $NaH_2PO_4$, 51 mM $Na_2HPO_4$, 100 mM $K_2SO_4$, 0.0005% Tween-80 at pH 6.8.

All DLS experiments were performed using a DynaPro Titan cuvette system (Wyatt Technology Europe, Dernbach, Germany) with protein concentrations between 0.2 and 1.0 mg/ml. In case of precipitation or particle formation, the sample was centrifuged at 10.000 g for 5 minutes prior to the experiment.

The extracellular domain (ECD) of mouse IL-17 receptor E (UniProt Q8BH06, isoform 1) and human IL-17 receptor E (UniProt Q8NFR9) were cloned in the expression vector pMAX_vk_Fc2_His using KpnI and EcoRV resulting in C-terminal Fc2_H fusion constructs. Beside the natural leader (AG00158) a second construct with a VK-Leader was generated (AG00159).

Both constructs were transiently expressed in HKB11 cells. The cell suspension was scaled up three days post transfection and the cell culture supernatant was harvested 6 days post transfection. After sterile filtration, the solution was subjected to protein A affinity chromatography. Buffer exchange was performed to PBS and samples were sterile filtered (0.2 pm pore size). Protein concentrations were determined by UV-spectrophotometry. Purity of the products was analysed under denaturing, reducing and denaturing, non-reducing conditions in SDS-PAGE and in native state by HP-SEC and DLS.

1.2. Pannings and Fab/Antibody Generation

For the antibody generation the MorphoSys Ylanthia® library was used to select Fab fragments against human IL-17C. The MorphoSys Ylanthia® library (Tiller et al. mAbs 5:3, 1-26; May/June (2013) and U.S. Pat. No. 8,728, 981) is a commercially available phagemid library and employs the CysDisplay® technology for displaying the Fab on the phage surface (Lohning et al., WO2001/05950).

To identify IL-17C—specific antibodies different panning strategies were used. Each panning strategy comprised at least 3 individual rounds of panning against the respective antigens including human IL-17C (SEQ ID NO: 1) and mouse IL-17C.

The isolated clones identified were maturated, engineered and/or germlined in order to increase affinity and/or functionality. Thereafter several hundred clones were screened and functionality was rigorously tested in in vitro assays comprising e.g. the evaluation of binding to human, cynomolgus monkey and mouse IL-17C via SET, inhibition of binding of human, cynomolgus monkey and mouse IL-17C to its respective IL-17RE and functional inhibition of IL-17C (IL-17RE-driven NF-κB reporter assay in mouse NIH3T3 cells and IL-17C mediated CSF3 expression in mouse primary keratinocytes (MPEK)).

Finally two preferred lead molecules (MAB#1 and MAB#2) were selected and are further described in the working examples as outlined below Example 2

Affinity Determination in Monovalent Fab and Bivalent IgG Format

Monovalent Fab and bivalent IgG affinity was determined by SET. Therefore purified Fabs were titrated on human, cynomolgus or mouse IL-17C for determination of KD. Respectively purified IgGs were titrated on human, cynomolgus or mouse IL-17C for $EC_{50}$ determination.

Solution equilibrium titration (SET) was basically performed as described in the literature (Friquet et al., (1985) J. Immunol. Meth. 77: 305-19). In order to improve the sensitivity and accuracy of the SET method, it was transferred from classical ELISA to ECL based technology (Haenel et al. (2005) Anal Biochem. 339.1: 182-84).

Respective results for MAB#1 and MAB#2 are shown in Table 2 and Table 3 respectively.

Example 3

Characterization of IL-17C Specific Fabs or IgGs for Receptor Inhibition Activity Purified IL-17C specific Fabs or IgGs, respectively were tested for its capacity to inhibit the binding of IL-17C to its specific receptor IL-17RE. Therefore MA6000 384-well plates (Meso Scale Discovery, MSD) were coated with 30 µl of mouse IL17RE/Fc chimeric protein at 75 ng/ml in PBS at 4° C. overnight. The next day a serial antibody dilution (concentrations from 0.001 to 100 nM) were pre-incubated for 30 min at RT with an equal volume of biotinylated human/cynomolgus or mouse IL-17C to determine an $IC_{50}$ concentration for receptor binding inhibition. After blocking of plates for 1 h with 2.5% BSA in PBST, previously formed antibody-ligand complexes were added for 1 h to coated IL17RE/Fc and receptor binding was detected via Streptavidin-ECL using MSD Sector Imager.

Both antibodies (MAB#1 and MAB#2) equally inhibited interaction of human/cynomolgus or mouse IL-17C with IL-17RE in Fab and in IgG format. $IC_{50}$ concentrations in the double-digit pM-range were observed for both antibodies in IgG format throughout all three clinically relevant species. Results are shown in rows 3 and 4 in Table 2 and Table 3 respectively.

Example 4

Functional Testing in IL-17C-Driven NF-κB Reporter Assay

Purified IL-17C specific IgGs were further tested for their ability to inhibit the biological activity of human, mouse and cynomolgus IL-17C in a functional cell based assay that monitors the IL-17C driven activation of a NF-κB reporter gene in NIH3T3 cells overexpressing the murine IL-17RE.

NIH3T3 cells were cultured in DMEM supplemented with 10% FBS and 1% Pen/Strep at 37° C., 5% $CO_2$. For the assay, NIH3T3 cells were transfected in suspension with total amount of 100 ng DNA (20 ng mouse IL-17RE expression construct, 50 ng NF-κB luciferase reporter construct and 30 ng pBluescript) using the Polyplus jet-PEI transfection agent. In brief, the DNA was diluted in 5 µl 150 mM NaCl (per well) and 0.2 µl jet-PEI in 8 µl 150 mM NaCl (per well) was prepared. After 5 minutes incubation at room temperature, the JetPEI® solution was added to the DNA solution and further incubated for 20-30 minutes at room temperature. NIH3T3 cells were diluted to have ~40,000 cells in 87 µl medium. The cells were added to the DNA-JetPEI I® mix (87 µl cells and 13 µl DNA-JetPEI I® mix/well) and the final volume was transferred into 96 well plates.

After an overnight incubation at 37° C. in a humidified 5% $CO_2$ incubator, the medium was removed and replaced jetPEI® with 90 µl medium containing 5% FBS and 1% Pen/Strep. 10 µl of a serial antibody dilution made in DPBS that was pre-incubated for 30 minutes at room temperature with an equal volume of purified recombinant IL-17C (either human IL-17C (Novus #NBP1-42910), mouse mIL-17C (R&D Systems #2306-ml-025) or cynomolgus IL-17C (produced in house), was added to the cells. The final concentration of IL-17C was 0.5 ng/ml.

After incubating the plates at 37° C. in $CO_2$ incubator, 100 µl SteadyLite Plus (Perkin Elmer) is added followed by readout of the luminescence on the Envision (Perkin Elmer).

Both antibodies effectively reduced NF-κB reporter gene activation mediated by IL-17RE in the presence of human, mouse and cynomolgus IL-17C. Respective results can be found in row 5 of Table 2 and Table 3 respectively.

Example 5

IL-17C-Driven Gene Expression in Primary Human Keratinocytes

Keratinocytes endogenously express the IL-17RE and IL-17RA receptors, both of which are needed for functional signaling of IL-17C. Human primary keratinocytes derived from healthy individuals and mouse primary keratinocytes derived from C57BL/6 mice were therefore used to determine the capacity of MAB#1 IgG1 and MAB#2 IgG1 to inhibit the biological activity of respectively human and mouse IL-17C in a more physiological context.

NHEK (normal human epidermal keratinocytes) were obtained from Lonza and cultured in Keratinocyte Growth Medium with supplements (KGM-Gold™ Bullet kit, Lonza) following manufacturer's protocol. NHEKs that were subcultured to and cryopreserved at passage 3 were thawed and immediately seeded in KGM cell culture medium at 30,000 cells/well in a 96 well cell culture plate. After 2 days, the medium was removed and changed to KGM-Gold w/o hydrocortisone prior to addition of hIL-17C (Novus #NBP1-42910) and hTNFα (Peprotech #300-01A) to final concentrations of 10 ng/ml each.

For testing antibodies, the human IL-17C was first pre-incubated for 30 minutes at room temperature with an equal volume of a serial dilution of antibody made in DPBS. Cells were stimulated with recombinant IL-17C (pre-incubated with or without a dilution of antibody) in presence of TNFα. Co stimulation with IL-17C and TNFα is known to result in synergistic induction of various genes and was shown to be necessary as IL-17C alone has limited effect on the expression of investigated genes.

Cells were cultured for 48 hours and then total RNA was extracted using RNeasy 96 Kit (Qiagen), reverse transcribed using Taqman® Reverse Transcription Reagents (Applied Biosystems) and the expression of beta-defensin 2 DEFB4A (human) or CSF3 (mouse) genes was determined by quantitative polymerase chain reaction (qPCR). In brief, 10 μl PCR reactions were prepared using Taqman® universal PCR master mix/No AmpErase® UNG and predesigned Assay-on-demand Gene expression primer/probe sets for DEF4B or CSF3 (#Hs00823638_m1, all Applied Biosystems). qPCR was performed on the ViiA7™ Real-Time PCR instrument (Applied Biosystems). Gene expression was normalized to a housekeeping gene either β-actin (Taqman primer set #4310881E) or GAPDH (Taqman primer set #4310893E).

Both antibodies (MAB#1 and MAB#2) were shown to effectively reduce 2 DEFB4A (human) or CSF3 (mouse) gene expression respectively and confirmed their ability to neutralize the biological activity of human IL-17C and also mouse IL-17C (Table 2 and Table 3).

Overview of Functional In Vitro Characterization:

Respective results from in vitro testing are summarized in Table 2 for MAB#1 and in Table 3 for MAB#2. The amino acid and the nucleic acid sequences of the variable regions and the CDRs of those two antibodies are shown in Table 1. Both antibodies fulfilled respective criteria and were considered as potential molecules for clinical development.

TABLE 2

Summary in vitro characterization MAB#1

| MAB#1 | Human IL-17C | Mouse IL-17C | Cynomolgus IL-17C |
|---|---|---|---|
| SET monovalent affinity (Fab) | $K_D$ = 3950 ± 50 pM (n = 2) | $K_D$ = 28000 ± 4000 pM (n = 2) | $K_D$ = 22000 ± 100 pM (n = 2) |
| SET apparent affinity (IgG) | $EC_{50}$ = 19 ± 6.9 pM (n = 3) | $EC_{50}$ = 387 ± 63 pM (n = 3) | $EC_{50}$ = 257 ± 59 pM (n = 3) |
| Receptor inhibition assay - Fab format | $IC_{50}$ = 2900 pM | $IC_{50}$ = 6000 pM | $IC_{50}$ = 2700 pM |
| Receptor inhibition assay - IgG format | $IC_{50}$ = 59 pM | $IC_{50}$ = 55 pM | $IC_{50}$ = 44 pM |
| NF-κB reporter assay | $IC_{50}$ = 31.3 ± 12.1 pM (n = 3) | $IC_{50}$ = 47.6 ± 9.4 pM (n = 3) | $IC_{50}$ = 12.8 ± 1.9 pM (n = 3) |
| Keratinocyte assay | $IC_{50}$ = 319.2 ± 86.3 pM (n = 3) | $IC_{50}$ = 112.1 ± 26.7 pM (n = 3) | n.d. |

TABLE 3

Summary in vitro characterization MAB#2

| MAB#2 | Human IL-17C | Mouse IL-17C | Cynomolgus IL-17C |
|---|---|---|---|
| SET monovalent affinity (Fab) | $K_D$ = 37 ± 17 pM (n = 2) | $K_D$ = 460 ± 90 pM (n = 2) | $K_D$ = 63 ± 20 pM (n = 2) |
| SET apparent affinity (IgG) | $EC_{50}$ = 16 ± 4 pM (n = 3) | $EC_{50}$ = 323 ± 12 pM (n = 3) | NT |
| Receptor inhibition assay - Fab format | $IC_{50}$ = 76 pM | $IC_{50}$ = 150 pM | $IC_{50}$ = 50 pM |
| Receptor inhibition assay - IgG format | $IC_{50}$ = 58 pM | $IC_{50}$ = 48 pM | $IC_{50}$ = 57 pM |
| NF-κB reporter assay | $IC_{50}$ = 18.5 ± 2.2 pM (n = 3) | $IC_{50}$ = 64.8 ± 8.6 pM (n = 3) | $IC_{50}$ = 12.9 ± 4.5 pM (n = 3) |
| Keratinocyte assay | $IC_{50}$ = 279.9 ± 161.7 pM (n = 3) | $IC_{50}$ = 51.0 ± 9.0 pM (n = 3) | n.d. |

Example 6

ELISA-Based Cross-Competition Assay

Cross-competition of an anti-IL-17C antibody or another IL-17C binding agent may be detected by using an ELISA assay according to the following standard procedure.

The general principle of the ELISA-assay involves coating of an anti-IL-17C antibody (such as MAB#1 or MAB#2) onto the wells of an ELISA plate. An excess amount of a second, potentially cross-competitive, anti-IL-17C antibody is then added in solution (i.e. not bound to the ELISA plate). Subsequently a limited amount of IL-17C-Fc is then added to the wells.

The antibody which is coated onto the wells and the antibody in solution will compete for binding of the limited number of IL-17C molecules. The plate is then washed to remove IL-17C molecules that has not bound to the coated antibody and to also remove the second, solution phase antibody as well as any complexes formed between the second, solution phase antibody and IL-17C. The amount of bound IL-17C is then measured using an appropriate IL-17C detection reagent. Therefore, IL-17C may be fused with a tag, e.g. Fc, Flag, etc. which can be detected via an appropriate tag-specific agent.

An antibody in solution that is cross-competitive to the coated antibody will be able to cause a decrease in the number of IL-17C molecules that the coated antibody can bind relative to the number of IL-17C molecules that the coated antibody can bind in the absence of the second, solution phase antibody.

This assay is described in more detail further below for two antibodies termed Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y IL-17C binding sites per well are at least 10 fold higher than the moles of Ab-X IL-17C binding sites that are used, per well, during the coating of the ELISA plate. IL-17C is added such that the moles of IL-17C added per well were at least 25-fold lower than the moles of Ab-X IL-17C binding sites that are used for coating each well. Following a suitable incubation period, the ELISA plate is washed and a detection reagent specific for the IL-17C antigen is added to measure the amount of IL-17C molecules specifically bound by the coated anti-IL-17C antibody (in this case Ab-X). The background signal for the assay is defined as the signal obtained in wells with the coated antibody (in this case Ab-X), second solution phase antibody (in this case Ab-Y), buffer only (i.e. no IL-17C) and detection reagents. The positive control signal for the assay is defined as the signal obtained in wells with the coated antibody (in this case Ab-X), second solution phase antibody buffer only (i.e. no second solution phase antibody), IL-17C detection reagents. The ELISA assay needs to be run in such a manner so as to have the positive control signal be at least 6 times the background signal.

To avoid any artifacts (e.g. significantly different affinities between Ab-X and Ab-Y for IL-17C) resulting from the choice of which antibody to use as the coating antibody and which to use as the second (competitor) antibody, the cross-blocking assay needs to be run in two formats: 1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

Example 7

IL-23 Induced Psoriasis-Model in Mice

To examine in vivo efficacy and therapeutic potential, both candidate antibodies were further evaluated in an IL-23 induced psoriasis-model in mice.

The IL-23 induced psoriasis-model in mice was essentially carried out as described by Rizzo H et al. J Immunol (2011) Vol. 186(3) pp. 1495-1502.

In brief, skin lesions were induced in Balb/C mice by intradermal injection of IL-23 into the ears(1 µg) for 4 consecutive days (day1 to day4). Measurement of gross ear thickness was done daily up to day 5 on which the mice were sacrificed. At sacrifice, the pinna ears were sampled and cut longitudinally in 2 halves. One half was fixed in formalin for in depth histological analysis of epidermal/dermal thickness of ear skin. The second half was immersed in RNAlater for quantitative reverse-transcription polymerase chain reaction (qRT-PCR) analysis of mRNA expression levels of disease-relevant IL-17A, IL-22 and IL-1β pro-inflammatory cytokines and LCN2, S100A8 and S100A9 anti-microbial proteins. Groups (n=10) of IL-23 injected mice were treated with the MAB#1 or MAB#2 antibodies which were administered twice i.p. at a dose of 10 mg/kg (once 3 days before and once just before the first IL-23 intradermal injection).

Each antibody was tested in 2 independent experiments divided over 3 different studies. In each study the following control groups (each n=10) were included:

A control group of mice did not receive daily injections of IL-23 but instead received daily intradermal injection of the same volume of a BSA/PBS solution. This group was treated with a negative control isotype antibody MOR03207 (2×10 mg/kg, i.p.).

For each of the studies the gross ear thickness and epidermal thickness was followed over time and individual data points per animal were used to determine the % prevention of the IL-23 mediated thickening. qPCR expression data were expressed using the Rq (relative quantity) equation (Rq=2−ΔCt where ΔCt=Ct (gene of interest)−Ct (housekeeping gene)) after normalization to cyclophilin A expression levels used as housekeeping gene. For all measurements, mean±SEM data of groups were compared with a one-way analysis of variance (ANOVA) and Dunnett multiple comparison post hoc test using PRISM software. A "p" value of <0.05 was considered to be statistically significant (*: $p<0.05$; : $p<0.01$; *: $p<0.001$; ns: not significant)

In summary, the administration of both candidates IgGs MAB#1 and MAB#2 (2×10 mg/kg) ameliorated the IL-23 induced skin inflammation, demonstrating the in vivo efficacy and therapeutic potential of both antibodies. Both antibodies had similar effects at level of IL-23 induced epidermal thickening and a similar impact at level of IL-23 induced gene expression. (see Table 4).

TABLE 4

| Summary In vivo efficacy in IL-23 model | | |
|---|---|---|
| | MAB#1 | MAB#2 |
| % prevention of Gross ear thickness (mean and significance in 2-3 studies) | −34 Significant in 2 out of 2 studies | −6 Not significant in 2 out of 2 studies |
| % prevention of epidermal thickness (mean and significance in 2-3 studies) | −62 Significant in 2 out of 2 studies | −50 Significant in 2 out of 2 studies |
| Number of disease related genes significantly reduced (in each of the 3 studies performed) | nt/3/6 | 1/6/nt |

Example 8

MC903 Mouse Model of Atopic Dermatitis

The efficacy of the MAB#1 antibody in atopic dermatitis was examined in a non-infectious cutaneous inflammation mouse model of atopic dermatitis where topical application of the low-calcemic vitamin D3 analogue MC903 (calcipotriol) induces atopic dermatitis like skin lesion characterized by a red and scaly skin, accompanied by an epidermal hyperplasia and dermal infiltration of various cell types as well as an increase of Th2 cytokine in skin and elevated serum IgE (Li M et al. Proc Natl Acad Sci USA (2006) Vol. 103(31) pp. 11736-11741; Li M et al. J Invest Dermatol. (2009) Vol. 129(2). pp. 498-502).

8.1 Animals

BALB/c mice (female, 8-week old) were obtained from Janvier Labs (France). Mice were kept on a 12 hours light/dark cycle (0700-1900). Temperature was maintained at 22° C., and food and water were provided ad libitum.

8.2. Experimental Procedures

In order to induce an AD-like response, 2 nmol MC903 (Tocris, dissolved in ethanol) was topical applied in a volume of 20 µL on both ears of mice for 5 consecutive days. A non-disease control group received the same quantity of ethanol (EtOH).

The severity of skin inflammation (erythema and thickening) was observed daily. Ear thickness was measured with an electronic caliper (Mitutoyo). Inflammation was further assessed using an in vivo imaging technique. To that end, Prosense 680 probe (1.6 nmol, Perkin Elmer) was administered by intraperitoneal route 24 hours before imaging. Imaging was performed with the Bruker In-vivo Xtreme Imaging System. Images were captured by a deeply cooled 4MP CCD camera (f-stop 1.1, binning 2×2, 5 sec acquisition time, Ex 630 nm, Em 700 nm). For anatomical co-registration, a reflectance image was taken (f-stop 2.8, 0.175 sec acquisition time). All images were taken with a 190×190 field of view and images were analysed using Molecular Imaging Software version 7.1 (Bruker Biospin, Billerica, Mass., USA). For each group, the mean values and standard error of mean (sem) was calculated using for each mouse the mean value of left and right ear.

At sacrifice, samples form ear skin were collected and fixed in 4% formaldehyde before embedding in paraffin. 4 µm-thick slices were stained with hematoxylin and eosin (H&E stain) for histomorphometric evaluation of epidermal thickness by image analysis with Sisn'Com software (France). Five fields per ear (high power field×20) covering the whole ear from top to bottom were measured, and the 5 values were averaged per ear and per mice (left/right ear). An additional set of tissue slices were prepared for IHC staining of IL-17C using the anti-IL-17C biotinylated MAB antibody (and biotinylated MOR03207 isotype negative control antibody). Processing and staining was essentially done as described above.

Ear skin samples were also taken for analysis of cytokine expression using qPCR or ELISA. Ear tissue pieces for qPCR gene analysis were submerged in RNALater® stabilisation solution (Ambion) and stored at −20° C. Ear skin samples for quantification at protein level were immediately snap frozen in liquid N2 and stored at −80° C. For gene expression analysis, tissue was disrupted and lysed in RNA lysis solution using Precellys homogenisator (microtubes filled with 1.4 mm ceramide beads, 3 times 3 cycles of 15 sec at 6000 rpm). Total RNA was further extracted using NucleoSpin® RNA Kit according to manufactures guidelines (Macherey-Nagel) and 300 ng was reverse-transcribed using Applied Biosystems™ High-Capacity cDNA Reverse Transcription Kit. 5 µL of 10-fold diluted cDNA was used in real-time quantitative PCR reactions using SYBR Green technology with gene-specific primers from Qiagen. qPCR was performed on the ViiA™ 7 Real-Time PCR System (Applied Biosystems). Gene expression was normalized to the expression of 3 different house-keeping genes (cyclophilin, b-actin and GAPDH) and expressed as relative mRNA level of specific gene expression as obtained using the $2^{-\Delta Ct}$ method, with $\Delta Ct=Ctgene-Geomean Ct-value$ (housekeeping genes). For quantification of expression at protein level, tissues were first disrupted and lysed in 250 µL lysis buffer (T-PER™ Tissue Protein Extraction Reagent (Pierce) supplemented with Protease Inhibitor Cocktail (Roche) and Halt™ Phosphatase Inhibitor Cocktail (Pierce)) using Precellys homogenisator (microtubes filled with 2.8 mm metal beads, 10 min 14000 rpm at 4° C.). The amount of TSLP in ears was determined using a TSLP mouse DuoSet ELISA kits from R&D System. The amount was normalized to total protein content in lysate which was determined using Coomassie Protein Assay Reagent (Thermo Fisher) in reference to BSA protein standard. Data were expressed as amount of cytokine in ear which was calculated using the formula: concentration cytokine in sample/concentration of protein in sample×total ear protein content.

The significance of effect of a treatment on each of the readouts was assessed with Prism® Software using one-way ANOVA followed by a Dunnett's multiple comparison post-hoc test versus the MC903+MOR03207 control group with *: $p<0.05$; : $p<0.01$; *: $p<0.001$.

8.3. Efficacy of MAB#1 in a Mouse Model of Atopic Dermatitis (Prophylactic)

The efficacy of various doses of MAB#1 in the MC903 atopic dermatitis model was assessed in a prophylactic setting. In brief, skin lesions were induced in BALB/c mice by topical administration of 2 nmol MC903 (dissolved in ethanol) on both ears for 5 consecutive days; mice were sacrificed at Day 8. MAB#1 was administered i.p. 3 times, i.e. 3 days before, at start of and 4 days after the first MC903 application. Effects on ear swelling, ear inflammation, epidermal hyperplasia, dermal thickness and gene expression were evaluated. A group of mice which received an isotype negative control antibody (MOR03207) served as comparator. Dexamethasone (5 mg/kg in 0.5% methyl cellulose, administered daily by oral route (p.o.) as of the first day of MC903 application) was used as active comparator. Mice were randomly divided into equal groups (n=10).

The severity of skin inflammation (erythema and thickening) was followed during the course of the experiment. The gross ear thickness was measured using a Mitutoyo thickness gage during the course of the experiment. Inflammation was further assessed at Day 5 using an in vivo imaging technique as described in 8.2).

Figure 1:
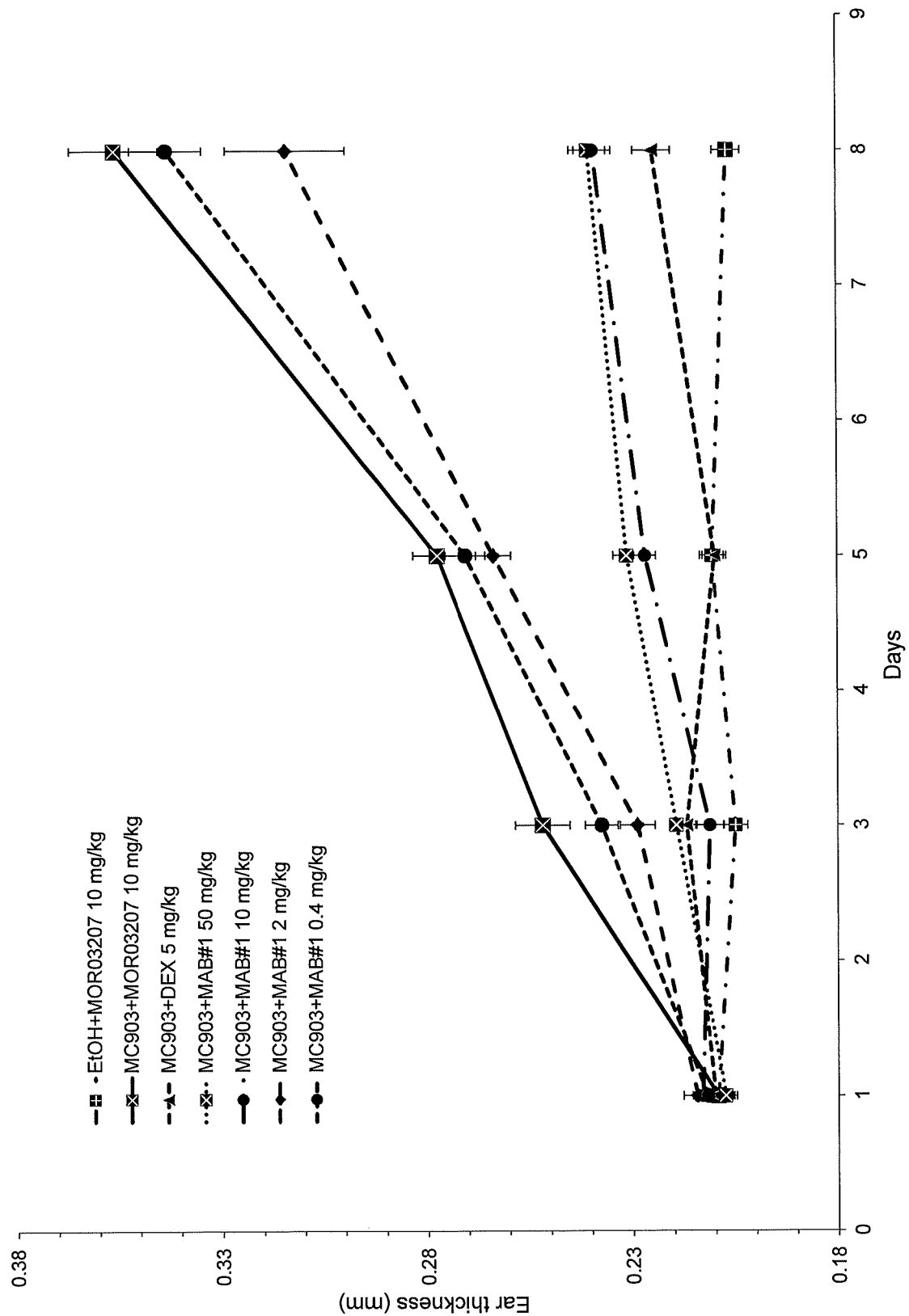
FIG. 1: MAB#1 dose-dependently prevents the ear thickening induced by topical application of MC903 on ear skin. Data are expressed as mean values±standard error of the mean (SEM) (n=8 per group). Statistical significance versus MC903+MOR03207 was calculated using ANOVA and Dunnett's multiple comparison test: * p<0.05;  p<0.01; * p<0.001. (DEX: dexamethasone; EtOH: ethanol)
Figure 2:
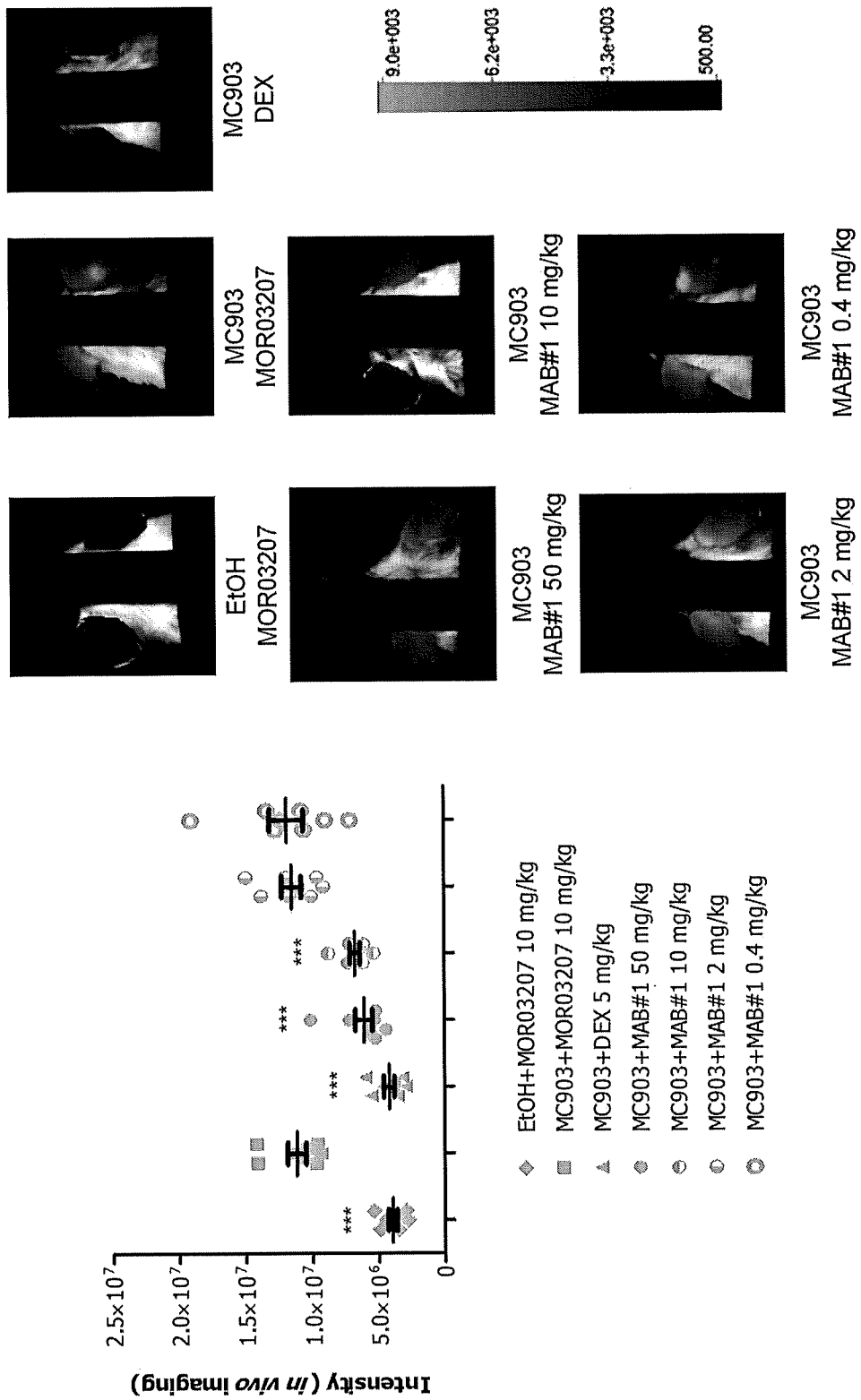
FIG. 2: MAB#1 dose-dependently reduces the ear inflammation induced by topical application of MC903 on ear skin. Ear inflammation was assessed at Day 5 using in vivo imaging. Left panel: quantification of signal intensity in ears. Individual data points (n=8 per group) represent the average intensity of both ears; data are also shown as mean values (horizontal lines)±SEM. Statistical significance versus MC903+MOR03207 was calculated using ANOVA and Dunnett's multiple comparison test: * p<0.05; ** p<0.01.

Ethanol (as vehicle control) had no effect on ears. In contrast, MC903-treated ears became red and swollen. Treatment with MAB#1 at doses of 2 mg/kg or higher significantly prevented ear thickening. The effect of MAB#1 was maximal at a dose of 10 mg/kg and was comparable to the effect of dexamethasone (FIG. 1). In line with these observations, ear inflammation (assessed by in vivo imaging at Day 5) was clearly increased in MC903-treated animals and reduced by MAB#1 with significant and near maximal effect observed at a dose of 10 mg/kg (FIG. 2).

To confirm the reduction of ear thickness by MAB#1, histological sections of ears collected at Day 8 were stained with hematoxylin and eosin for histomorphometric evaluation of epidermal and dermal thickness. Values of five fields per ear covering the whole ear from top to bottom were captured, and averaged per mouse. MAB#1 at doses of 10 mg/kg and higher significantly prevented the increase in thickness of both epidermal and dermal layer (FIG. 3).

8.3.1 Effect of MAB#1 on Gene Expression

To further characterize the effect of MAB#1 in the MC903 atopic dermatitis-like skin inflammation model, the expression of various atopic dermatitis-relevant genes was analysed at mRNA level by qPCR or at protein level by enzyme-linked immunosorbent assay (ELISA). TSLP and IL-33 protein expression in ears and TARC level in plasma were increased by MC903 application and significantly inhibited upon treatment with MAB#1 at doses of 10 mg/kg or higher (FIG. 4). A similar inhibitory effect was observed with MAB#1 on several other genes that were upregulated in MC903-treated ears, like IL-31 (a cytokine linked with itch in atopic dermatitis), the Th2-cytokine IL-4, and other genes that have been shown to be upregulated in human atopic dermatitis, like S100A8/9 and IFN-γ. Vice versa, MAB#1 was shown to prevent the downregulation of FLG2 in MC903-treated ears, which might suggest a potential role of MAB#1 in restoring barrier function.

8.4 Efficacy of MAB#1 in a Mouse Model of Atopic Dermatitis (Therapeutic)

The efficacy of various doses of MAB#1 in the MC903 atopic dermatitis model was assessed in a more disease-relevant therapeutic setting. In brief, skin lesions were induced in BALB/c mice before the start of any treatment by topical administration of 2 nmol MC903 (dissolved in ethanol) on both ears for 5 consecutive days. MAB#1 was administered i.p. 4 times, with the first administration at the last day of MC903 skin application (Day 5) and following ones at Day 8, 12 and 15. Mice were sacrificed at Day 16. Effects on ear swelling, ear inflammation, epidermal hyperplasia, dermal thickness and gene expression were evaluated. In addition, effect on influx of immune cells (eosinophils, T cells and mast cells) was also evaluated. A group of mice which received an isotype negative control antibody (MOR03207) served as comparator. Dexamethasone (1 mg/kg in 0.5% methyl cellulose, administered p.o. starting as of the last day of MC903 application at Day 5 and subsequently from Day 8 to 12 and from Day 15 to 16) was used as active comparator.

8.4.1 Effect of MAB#1 on Gross Ear Thickness and Inflammation

The gross ear thickness was measured using a Mitutoyo thickness gage during the course of the experiment. Topical application of MC903 on ears elicited a marked increase in ear thickness as of Day 3 as compared to ears treated with ethanol (as vehicle control for MC903). Disease activity was well induced at Day 5 (i.e. day of first treatment) and continued to evolve after (even though MC903 application was stopped) as evident from a continued increase in ear swelling in the group treated with the negative control antibody MOR03207 (FIG. 5). Treatment with MAB#1 at doses of 0.4 mg/kg or higher significantly reduced ear thickening as of Day 12, with the higher doses of MAB#1 having a stronger effect and significantly reducing ear thickness even at earlier time points (as of Day 8 for MAB#1 at 50 mg/kg and as of Day 10 for doses of 10 and 2 mg/kg). In line with these observations, ear inflammation as assessed by in vivo imaging (as described in 8.2) at Day 12, was still increased in animals treated with negative control antibody and significantly reduced by MAB#1 at all doses, with maximal effect observed at dose of 2 mg/kg (FIG. 6).

8.4.2 Effect of MAB#1 on Ear Epidermal/Dermal Thickness

To confirm the reduction of ear thickness by MAB#1, histological sections of ears collected at Day 16 were stained with hematoxylin and eosin for histomorphometric evaluation of epidermal and dermal thickness. MAB#1 at doses of 2 mg/kg and higher strongly reduced the increase in thickness of both epidermal and dermal layer, in line with the measurements of gross ear thickness (FIG. 7).

8.4.3 Effect of MAB#1 on Dermal Cell Infiltration

To further characterize the effect of MAB#1on disease processes in the MC903 atopic dermatitis model, we evaluated the effect on cell infiltrations. More specifically, we assessed the effect on eosinophils, T-lymphocytes and mast cells by immunohistochemistry (IHC) and subsequent quantification of the area that stained with respectively antibodies detecting eosinophil peroxidase, T cell marker CD3 and mast cell tryptases (for details see (Marsais, 2016)). In line with the increased inflammation and ear thickness, infiltration of eosinophils, T cells and to lesser extent mast cells was still prominent at Day 16 in ears of mice in which disease activity was induced by MC903. Treatment of MAB#1 reduced the dermal infiltration of all three cell types examined (FIG. 8). A significant reduction in number of infiltrated eosinophils and T cells was observed at all MAB#1 doses tested with the higher dose of 50 mg/kg having the more stronger effect reducing the influx of these cell types to levels comparable to the effect of dexamethasone. The effect on mast cell infiltration was in general weaker but still significant: influx was significantly reduced by MAB#1at the higher doses of 50 and 10 mg/kg.

8.4.4 Effect of MAB#1 on Gene Expression

Expression was analysed on ear skin samples or plasma collected at Day 16 either by qPCR for eight disease-relevant genes or by ELISA for TSLP and IL-33 produced in ears and TARC in plasma as described in 8.2.

No significant differential expression could be observed for most of the analysed genes between EtOH-treated non-disease control mice and mice in which disease was induced by application of MC903 for the first 5 days. Only levels of IL-33 protein and IL-4, S100A9 and IFN-γ mRNA expression levels were still increased. Increased expression levels for those genes (except IFN-γ) were reduced by MAB#1 treatment as shown in FIG. 9 at all dose levels.

8.5. Results

MAB#1 prevented the generation of an atopic dermatitis-like skin inflammation in the MC903 model, with a significant impact on epidermal and dermal thickening, inflammation and type 2 T helper cell (Th2)-like gene expression when dosed prophylactically at 3×10 mg/kg intraperitoneally (i.p.). Significant effects on gross ear thickness were already observed in this model at doses of 3×2 mg/kg (i.p.). Also in the therapeutic MC903 model MAB#1 improved skin inflammation. Significant therapeutic effects on gross ear thickness, epidermal thickening, inflammation and influx of eosinophils and T cells were observed at doses of 4×0.4 mg/kg (i.p.), up to doses of 4×2 to 10 mg/kg (i.p.).

Example 9

Flaky Tail Mouse Model of Atopic Dermatitis

The efficacy of the MAB#1 antibody was evaluated in the Flaky Tail model. Flaky Tail mice have a mutation in the Flg and Matt ($Matt^{ma/ma}Flg^{ft/ft}$) genes resulting in skin barrier dysfunction. These mice spontaneously develop atopy and progressive dermatitis characterised by a mixed Th2/Th17 inflammatory phenotype and reproduce cardinal features of AD in man.

9.1. Animals & Experimental Procedures

Flaky tail ($Matt^{ma/ma}Flg^{ft/ft}$) mice on a congenic C57BL/6J background were used as described in Fallon et al (2009) Nat Genet. 41(5): 602-608 and Saunders et al (2013) J Allergy Clin Immunol 132(5): 1121-1129. Female Flaky tail mice, 9-10 weeks old, were randomized into four groups (8 mice per group) and treated for 6 weeks as follows:

Group I: Isotype negative control antibody (MOR03207) (30 mg/kg, ip twice weekly×6 weeks)
Group II: MAB#1 (3 mg/kg, ip twice weekly×6 weeks)
Group III: MAB#1 (30mg/kg, ip twice weekly×6 weeks)
Group IV: Dexamethasone 2mg/kg (ip twice per week×6 weeks) as active comparator The severity of AD-like skin inflammation was scored using the macroscopic diagnostic criteria adapted from assessment of skin inflammation in the NC/Nga mouse model as described in Saunders et al (2013) J Allergy Clin Immunol 132(5): 1121-1129. In brief, a scoring system (0: none; 1: mild; 2: moderate; 3: marked) was applied to the signs of erythema, excoriation and scaling. The total scores for each mouse (with the maximum of 9) were calculated from the sum of the individual scores for each of the three parameters.

The occurrence of eczematous lesions in eyelid skin was monitored at end of the study and blepharitis was scored separately for its severity (0: normal, 1: eyelid erythema and/or edema, 2: eyelid erythema, edema and scaling, 3: eyelid erythema, edema, scaling, erosion). The maximum blepharitis score (mean of both eyes) for each mouse is 3.

9.2. Efficacy of MAB#1 in Spontaneous & Chronic Flaky Tail Mouse Model of AD

Clinical scoring of skin inflammation shows that Flaky Tail mice had already signs of spontaneous eczematous-like dermatitis at start of treatment which further progressed during the 6-week follow up period into an overt dermatitis, in non-treated animals. Treatment with MAB#1 reduces progression with significant effect comparable to the effect of dexamethasone observed at the highest tested dose of 30 mg/kg (FIG. 10). A similar effect of the MAB#1 antibody is observed at the level of blepharitis at the end of the treatment (FIG. 11).

The invention claimed is:

1. A method for treating a subject suffering from an inflammatory disorder, comprising administering to said subject an effective amount of an antibody or antibody fragment comprising
   a) a HCDR1 region comprising the amino acid sequence of SEQ ID NO: 7, a HCDR2 region comprising the amino acid sequence of SEQ ID NO: 8, a HCDR3 region comprising the amino acid sequence of SEQ ID NO: 9, a LCDR1 region comprising the amino acid sequence of SEQ ID NO: 13, a LCDR2 region comprising the amino acid sequence of SEQ ID NO: 14 and a LCDR3 region comprising the amino acid sequence of SEQ ID NO: 15, or
   b) a HCDR1 region comprising the amino acid sequence of SEQ ID NO: 20, a HCDR2 region comprising the amino acid sequence of SEQ ID NO: 21, a HCDR3 region comprising the amino acid sequence of SEQ ID NO: 22, a LCDR1 region comprising the amino acid sequence of SEQ ID NO: 26, a LCDR2 region comprising the amino acid sequence of SEQ ID NO: 27 and a LCDR3 region comprising the amino acid sequence of SEQ ID NO: 28.

2. The method of claim 1, wherein said antibody or antibody fragment is specific for human IL-17C.

3. The method of claim 2, wherein said antibody or antibody fragment is specific for human IL-17C, cynomolgus IL-17C and mouse IL-17C.

4. The method of claim 1, wherein said antibody or antibody fragment is a human, humanized or chimeric antibody or antibody fragment.

5. The method of claim 1, wherein said antibody or antibody fragment comprises the sequences set forth in SEQ ID NO: 17 and SEQ ID NO: 16.

6. The method of claim 1, wherein said antibody or antibody fragment comprises the sequences set forth in SEQ ID NO: 30 and SEQ ID NO: 29.

7. The method of claim 1, wherein said antibody or antibody fragment is an isolated antibody or antibody fragment.

8. The method of claim 1, wherein said antibody or antibody fragment is a recombinant antibody or antibody fragment.

9. A method for treating a subject suffering from an inflammatory disorder, comprising administering to said subject an effective amount of a pharmaceutical composition comprising an antibody or antibody fragment comprising
   a) a HCDR1 region comprising the amino acid sequence of SEQ ID NO: 7, a HCDR2 region comprising the amino acid sequence of SEQ ID NO: 8, a HCDR3 region comprising the amino acid sequence of SEQ ID NO: 9, a LCDR1 region comprising the amino acid sequence of SEQ ID NO: 13, a LCDR2 region comprising the amino acid sequence of SEQ ID NO: 14 and a LCDR3 region comprising the amino acid sequence of SEQ ID NO: 15, or
   b) a HCDR1 region comprising the amino acid sequence of SEQ ID NO: 20, a HCDR2 region comprising the amino acid sequence of SEQ ID NO: 21, a HCDR3 region comprising the amino acid sequence of SEQ ID NO: 22, a LCDR1 region comprising the amino acid sequence of SEQ ID NO: 26, a LCDR2 region comprising the amino acid sequence of SEQ ID NO: 27 and a LCDR3 region comprising the amino acid sequence of SEQ ID NO: 28; and
   a pharmaceutically acceptable carrier or excipient.

10. The method of claim 9, wherein said antibody or antibody fragment is specific for human IL-17C.

11. The method of claim 10, wherein said antibody or antibody fragment is specific for human IL-17C, cynomolgus IL-17C and mouse IL-17C.

12. The method of claim 9, wherein said antibody or antibody fragment is a human, humanized or chimeric antibody or antibody fragment.

13. The method of claim 9, wherein said antibody or antibody fragment comprises the sequences set forth in SEQ ID NO: 17 and SEQ ID NO: 16.

14. The method of claim 9, wherein said antibody or antibody fragment comprises the sequences set forth in SEQ ID NO: 30 and SEQ ID NO: 29.

15. The method of claim 9, wherein said antibody or antibody fragment is an isolated antibody or antibody fragment.

16. The method of claim 9, wherein said antibody or antibody fragment is a recombinant antibody or antibody fragment.

17. A method for treating a subject suffering from an inflammatory disorder, comprising administering to said subject an effective amount of an antibody or antibody fragment comprising
   (a) the sequences set forth in SEQ ID NO: 17 and SEQ ID NO: 16; or
   (b) the sequences set forth in SEQ ID NO: 30 and SEQ ID NO: 29.

* * * * *

SEQUENCE LISTING

```
<160> NUMBER OF SEQ ID NOS: 71

<210> SEQ ID NO 1
<211> LENGTH: 197
<212> TYPE: PRT
<213> ORGANISM: Homo sapiens

<400> SEQUENCE: 1

Met Thr Leu Leu Pro Gly Leu Leu Phe Leu Thr Trp Leu His Thr Cys
1               5                   10                  15

Leu Ala His His Asp Pro Ser Leu Arg Gly His Pro His Ser His Gly
                20                  25                  30

Thr Pro His Cys Tyr Ser Ala Glu Glu Leu Pro Leu Gly Gln Ala Pro
            35                  40                  45

Pro His Leu Leu Ala Arg Gly Ala Lys Trp Gly Gln Ala Leu Pro Val
        50                  55                  60

Ala Leu Val Ser Ser Leu Glu Ala Ala Ser His Arg Gly Arg His Glu
65                  70                  75                  80

Arg Pro Ser Ala Thr Thr Gln Cys Pro Val Leu Arg Pro Glu Glu Val
                85                  90                  95

Leu Glu Ala Asp Thr His Gln Arg Ser Ile Ser Pro Trp Arg Tyr Arg
            100                 105                 110

Val Asp Thr Asp Glu Asp Arg Tyr Pro Gln Lys Leu Ala Phe Ala Glu
        115                 120                 125
```

Cys Leu Cys Arg Gly Cys Ile Asp Ala Arg Thr Gly Arg Glu Thr Ala
            130                 135                 140

Ala Leu Asn Ser Val Arg Leu Leu Gln Ser Leu Val Leu Arg Arg
145                 150                 155                 160

Arg Pro Cys Ser Arg Asp Gly Ser Gly Leu Pro Thr Pro Gly Ala Phe
                165                 170                 175

Ala Phe His Thr Glu Phe Ile His Val Pro Val Gly Cys Thr Cys Val
            180                 185                 190

Leu Pro Arg Ser Val
        195

<210> SEQ ID NO 2
<211> LENGTH: 194
<212> TYPE: PRT
<213> ORGANISM: Mus musculus

<400> SEQUENCE: 2

Met Ser Leu Leu Leu Gly Trp Leu Pro Thr Gly Met Thr His Gln
1               5                   10                  15

Asp Pro Pro Ser Trp Gly Lys Pro Arg Ser His Arg Thr Leu Arg Cys
                20                  25                  30

Tyr Ser Ala Glu Glu Leu Ser His Gly Gln Ala Pro Pro His Leu Leu
            35                  40                  45

Thr Arg Ser Ala Arg Trp Glu Gln Ala Leu Pro Val Ala Leu Val Ala
        50                  55                  60

Ser Leu Glu Ala Thr Gly His Arg Arg Gln His Glu Gly Pro Leu Ala
65                  70                  75                  80

Gly Thr Gln Cys Pro Val Leu Arg Pro Glu Glu Val Leu Glu Ala Asp
                85                  90                  95

Thr His Glu Arg Ser Ile Ser Pro Trp Arg Tyr Arg Ile Asp Thr Asp
            100                 105                 110

Glu Asn Arg Tyr Pro Gln Lys Leu Ala Val Ala Glu Cys Leu Cys Arg
        115                 120                 125

Gly Cys Ile Asn Ala Lys Thr Gly Arg Glu Thr Ala Ala Leu Asn Ser
130                 135                 140

Val Gln Leu Leu Gln Ser Leu Val Leu Arg Arg Gln Pro Cys Ser
145                 150                 155                 160

Arg Asp Gly Thr Ala Asp Pro Thr Pro Gly Ser Phe Ala Phe His Thr
                165                 170                 175

Glu Phe Ile Arg Val Pro Val Gly Cys Thr Cys Val Leu Pro Arg Ser
            180                 185                 190

Thr Gln

<210> SEQ ID NO 3
<211> LENGTH: 197
<212> TYPE: PRT
<213> ORGANISM: Macaca fascicularis

<400> SEQUENCE: 3

Met Thr Leu Leu Pro Gly Leu Leu Phe Leu Thr Trp Leu His Ala Cys
1               5                   10                  15

Leu Ala His Gln Asp Pro Phe Leu Arg Gly His Pro His Thr His Gly
            20                  25                  30

Thr Pro Arg Cys Tyr Ser Ala Glu Glu Leu Pro Leu Gly Gln Ala Pro
        35                  40                  45

```
Pro His Leu Leu Ala Arg Gly Ala Lys Trp Gly Gln Ala Leu Pro Val
    50                  55                  60

Ala Leu Val Ser Ser Leu Glu Ala Gly His Arg Arg Arg His Asp
 65                  70                  75                  80

Arg Pro Ser Ala Ala Thr Gln Cys Pro Val Leu Arg Pro Glu Val
                 85                  90                  95

Leu Glu Ala Asp Thr His Gln Arg Ser Ile Ser Pro Trp Arg Tyr Arg
                100                 105                 110

Val Asp Thr Asp Glu Asp Arg Tyr Pro Gln Lys Leu Ala Phe Ala Glu
            115                 120                 125

Cys Leu Cys Arg Gly Cys Ile Asp Pro Arg Thr Gly Arg Glu Thr Ala
130                 135                 140

Ala Leu Asn Ser Val Arg Leu Leu Gln Ser Leu Leu Val Leu Arg Arg
145                 150                 155                 160

Arg Pro Cys Ser Arg Asp Gly Ser Gly Leu Pro Thr Pro Gly Ala Phe
                165                 170                 175

Ala Phe His Thr Glu Phe Ile Arg Val Pro Val Gly Cys Thr Cys Val
            180                 185                 190

Leu Pro Arg Ser Val
        195
```

<210> SEQ ID NO 4
<211> LENGTH: 866
<212> TYPE: PRT
<213> ORGANISM: Homo sapiens

<400> SEQUENCE: 4

```
Met Gly Ala Ala Arg Ser Pro Pro Ser Ala Val Pro Gly Pro Leu Leu
 1               5                  10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
         50                  55                  60

Pro Arg Asn Leu Thr Pro Ser Ser Pro Lys Asp Leu Gln Ile Gln Leu
 65                  70                  75                  80

His Phe Ala His Thr Gln Gln Gly Asp Leu Phe Pro Val Ala His Ile
                 85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His His Arg Arg Trp Arg Phe
        130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
210                 215                 220
```

```
Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
            245                 250                 255

Pro Glu Glu Phe His Gln Arg Ser Asn Val Thr Leu Thr Leu Arg Asn
        260                 265                 270

Leu Lys Gly Cys Cys Arg His Gln Val Gln Ile Gln Pro Phe Phe Ser
    275                 280                 285

Ser Cys Leu Asn Asp Cys Leu Arg His Ser Ala Thr Val Ser Cys Pro
290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
            325                 330                 335

Ile Leu Leu Ile Val Cys Met Thr Trp Arg Leu Ala Gly Pro Gly Ser
        340                 345                 350

Glu Lys Tyr Ser Asp Asp Thr Lys Tyr Thr Asp Gly Leu Pro Ala Ala
    355                 360                 365

Asp Leu Ile Pro Pro Leu Lys Pro Arg Lys Val Trp Ile Ile Tyr
370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
            405                 410                 415

Glu Gln Ala Ile Ser Glu Ala Gly Val Met Thr Trp Val Gly Arg Gln
        420                 425                 430

Lys Gln Glu Met Val Glu Ser Asn Ser Lys Ile Ile Val Leu Cys Ser
    435                 440                 445

Arg Gly Thr Arg Ala Lys Trp Gln Ala Leu Leu Gly Arg Gly Ala Pro
450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
            485                 490                 495

Gly Thr Tyr Val Val Cys Tyr Phe Ser Glu Val Ser Cys Asp Gly Asp
        500                 505                 510

Val Pro Asp Leu Phe Gly Ala Ala Pro Arg Tyr Pro Leu Met Asp Arg
    515                 520                 525

Phe Glu Glu Val Tyr Phe Arg Ile Gln Asp Leu Glu Met Phe Gln Pro
530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
            565                 570                 575

Trp Gln Val Arg Cys Pro Asp Trp Phe Glu Cys Glu Asn Leu Tyr Ser
        580                 585                 590

Ala Asp Asp Gln Asp Ala Pro Ser Leu Asp Glu Glu Val Phe Glu Glu
    595                 600                 605

Pro Leu Leu Pro Pro Gly Thr Gly Ile Val Lys Arg Ala Pro Leu Val
610                 615                 620

Arg Glu Pro Gly Ser Gln Ala Cys Leu Ala Ile Asp Pro Leu Val Gly
625                 630                 635                 640
```

-continued

```
Glu Glu Gly Gly Ala Val Ala Lys Leu Glu Pro His Leu Gln Pro
                645                 650                 655

Arg Gly Gln Pro Ala Pro Gln Pro Leu His Thr Leu Val Leu Ala Ala
            660                 665                 670

Glu Glu Gly Ala Leu Val Ala Ala Val Glu Pro Gly Pro Leu Ala Asp
        675                 680                 685

Gly Ala Ala Val Arg Leu Ala Leu Ala Gly Glu Gly Glu Ala Cys Pro
    690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
                725                 730                 735

Pro Asp Leu Leu Pro Glu Asp Val Arg Glu His Leu Glu Gly Leu Met
            740                 745                 750

Leu Ser Leu Phe Glu Gln Ser Leu Ser Cys Gln Ala Gln Gly Gly Cys
        755                 760                 765

Ser Arg Pro Ala Met Val Leu Thr Asp Pro His Thr Pro Tyr Glu Glu
    770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu Glu
                805                 810                 815

Glu Glu Gln Asp Pro Gly Lys Pro Ala Leu Pro Leu Ser Pro Glu Asp
            820                 825                 830

Leu Glu Ser Leu Arg Ser Leu Gln Arg Gln Leu Leu Phe Arg Gln Leu
        835                 840                 845

Gln Lys Asn Ser Gly Trp Asp Thr Met Gly Ser Glu Ser Glu Gly Pro
    850                 855                 860

Ser Ala
865

<210> SEQ ID NO 5
<211> LENGTH: 667
<212> TYPE: PRT
<213> ORGANISM: Homo sapiens

<400> SEQUENCE: 5

Met Gly Ser Ser Arg Leu Ala Ala Leu Leu Pro Leu Leu Leu Leu Ile
1               5                   10                  15

Val Ile Asp Leu Ser Asp Ser Ala Gly Ile Gly Phe Arg His Leu Pro
                20                  25                  30

His Trp Asn Thr Arg Cys Pro Leu Ala Ser His Thr Asp Asp Ser Phe
            35                  40                  45

Thr Gly Ser Ser Ala Tyr Ile Pro Cys Arg Thr Trp Trp Ala Leu Phe
        50                  55                  60

Ser Thr Lys Pro Trp Cys Val Arg Val Trp His Cys Ser Arg Cys Leu
65                  70                  75                  80

Cys Gln His Leu Leu Ser Gly Ser Gly Leu Gln Arg Gly Leu Phe
                85                  90                  95

His Leu Leu Val Gln Lys Ser Lys Lys Ser Ser Thr Phe Lys Phe Tyr
            100                 105                 110

Arg Arg His Lys Met Pro Ala Pro Ala Gln Arg Lys Leu Leu Pro Arg
        115                 120                 125

Arg His Leu Ser Glu Lys Ser His His Ile Ser Ile Pro Ser Pro Asp
    130                 135                 140
```

```
Ile Ser His Lys Gly Leu Arg Ser Lys Arg Thr Gln Pro Ser Asp Pro
145                 150                 155                 160

Glu Thr Trp Glu Ser Leu Pro Arg Leu Asp Ser Gln Arg His Gly Gly
            165                 170                 175

Pro Glu Phe Ser Phe Asp Leu Leu Pro Glu Ala Arg Ala Ile Arg Val
        180                 185                 190

Thr Ile Ser Ser Gly Pro Glu Val Ser Val Arg Leu Cys His Gln Trp
            195                 200                 205

Ala Leu Glu Cys Glu Glu Leu Ser Ser Pro Tyr Asp Val Gln Lys Ile
210                 215                 220

Val Ser Gly Gly His Thr Val Glu Leu Pro Tyr Glu Phe Leu Leu Pro
225                 230                 235                 240

Cys Leu Cys Ile Glu Ala Ser Tyr Leu Gln Glu Asp Thr Val Arg Arg
                245                 250                 255

Lys Lys Cys Pro Phe Gln Ser Trp Pro Glu Ala Tyr Gly Ser Asp Phe
            260                 265                 270

Trp Lys Ser Val His Phe Thr Asp Tyr Ser Gln His Thr Gln Met Val
        275                 280                 285

Met Ala Leu Thr Leu Arg Cys Pro Leu Lys Leu Glu Ala Ala Leu Cys
    290                 295                 300

Gln Arg His Asp Trp His Thr Leu Cys Lys Asp Leu Pro Asn Ala Thr
305                 310                 315                 320

Ala Arg Glu Ser Asp Gly Trp Tyr Val Leu Glu Lys Val Asp Leu His
                325                 330                 335

Pro Gln Leu Cys Phe Lys Phe Ser Phe Gly Asn Ser Ser His Val Glu
            340                 345                 350

Cys Pro His Gln Thr Gly Ser Leu Thr Ser Trp Asn Val Ser Met Asp
        355                 360                 365

Thr Gln Ala Gln Gln Leu Ile Leu His Phe Ser Ser Arg Met His Ala
    370                 375                 380

Thr Phe Ser Ala Ala Trp Ser Leu Pro Gly Leu Gly Gln Asp Thr Leu
385                 390                 395                 400

Val Pro Pro Val Tyr Thr Val Ser Gln Ala Arg Gly Ser Ser Pro Val
                405                 410                 415

Ser Leu Asp Leu Ile Ile Pro Phe Leu Arg Pro Gly Cys Cys Val Leu
            420                 425                 430

Val Trp Arg Ser Asp Val Gln Phe Ala Trp Lys His Leu Leu Cys Pro
        435                 440                 445

Asp Val Ser Tyr Arg His Leu Gly Leu Leu Ile Leu Ala Leu Leu Ala
    450                 455                 460

Leu Leu Thr Leu Leu Gly Val Val Leu Ala Leu Thr Cys Arg Arg Pro
465                 470                 475                 480

Gln Ser Gly Pro Gly Pro Ala Arg Pro Val Leu Leu Leu His Ala Ala
                485                 490                 495

Asp Ser Glu Ala Gln Arg Arg Leu Val Gly Ala Leu Ala Glu Leu Leu
            500                 505                 510

Arg Ala Ala Leu Gly Gly Gly Arg Asp Val Ile Val Asp Leu Trp Glu
        515                 520                 525

Gly Arg His Val Ala Arg Val Gly Pro Leu Pro Trp Leu Trp Ala Ala
    530                 535                 540

Arg Thr Arg Val Ala Arg Glu Gln Gly Thr Val Leu Leu Leu Trp Ser
545                 550                 555                 560
```

```
Gly Ala Asp Leu Arg Pro Val Ser Gly Pro Asp Pro Arg Ala Ala Pro
                565                 570                 575

Leu Leu Ala Leu Leu His Ala Ala Pro Arg Pro Leu Leu Leu Leu Ala
            580                 585                 590

Tyr Phe Ser Arg Leu Cys Ala Lys Gly Asp Ile Pro Pro Pro Leu Arg
        595                 600                 605

Ala Leu Pro Arg Tyr Arg Leu Arg Asp Leu Pro Arg Leu Leu Arg
    610                 615                 620

Ala Leu Asp Ala Arg Pro Phe Ala Glu Ala Thr Ser Trp Gly Arg Leu
625                 630                 635                 640

Gly Ala Arg Gln Arg Arg Gln Ser Arg Leu Glu Leu Cys Ser Arg Leu
                645                 650                 655

Glu Arg Glu Ala Ala Arg Leu Ala Asp Leu Gly
            660                 665

<210> SEQ ID NO 6
<211> LENGTH: 637
<212> TYPE: PRT
<213> ORGANISM: Mus musculus

<400> SEQUENCE: 6

Met Gly Ser Pro Arg Leu Ala Ala Leu Leu Ser Leu Pro Leu Leu
1               5                   10                  15

Leu Ile Gly Leu Ala Val Ser Ala Arg Val Ala Cys Pro Cys Leu Arg
            20                  25                  30

Ser Trp Thr Ser His Cys Leu Leu Ala Tyr Arg Val Asp Lys Arg Phe
        35                  40                  45

Ala Gly Leu Gln Trp Gly Trp Phe Pro Leu Val Arg Lys Ser Lys
    50                  55                  60

Ser Pro Pro Lys Phe Glu Asp Tyr Trp Arg His Arg Thr Pro Ala Ser
65                  70                  75                  80

Phe Gln Arg Lys Leu Leu Gly Ser Pro Ser Leu Ser Glu Glu Ser His
                85                  90                  95

Arg Ile Ser Ile Pro Ser Ser Ala Ile Ser His Arg Gly Gln Arg Thr
            100                 105                 110

Lys Arg Ala Gln Pro Ser Ala Ala Glu Gly Arg Glu His Leu Pro Glu
        115                 120                 125

Ala Gly Ser Gln Lys Cys Gly Gly Pro Glu Phe Ser Phe Asp Leu Leu
    130                 135                 140

Pro Glu Val Gln Ala Val Arg Val Thr Ile Pro Ala Gly Pro Lys Ala
145                 150                 155                 160

Ser Val Arg Leu Cys Tyr Gln Trp Ala Leu Glu Cys Glu Asp Leu Ser
                165                 170                 175

Ser Pro Phe Asp Thr Gln Lys Ile Val Ser Gly Gly His Thr Val Asp
            180                 185                 190

Leu Pro Tyr Glu Phe Leu Leu Pro Cys Met Cys Ile Glu Ala Ser Tyr
        195                 200                 205

Leu Gln Glu Asp Thr Val Arg Arg Lys Lys Cys Pro Phe Gln Ser Trp
    210                 215                 220

Pro Glu Ala Tyr Gly Ser Asp Phe Trp Gln Ser Ile Arg Phe Thr Asp
225                 230                 235                 240

Tyr Ser Gln His Asn Gln Met Val Met Ala Leu Thr Leu Arg Cys Pro
                245                 250                 255

Leu Lys Leu Glu Ala Ser Leu Cys Trp Arg Gln Asp Pro Leu Thr Pro
            260                 265                 270
```

-continued

```
Cys Glu Thr Leu Pro Asn Ala Thr Ala Gln Glu Ser Glu Gly Trp Tyr
        275                 280                 285

Ile Leu Glu Asn Val Asp Leu His Pro Gln Leu Cys Phe Lys Phe Ser
    290                 295                 300

Phe Glu Asn Ser Ser His Val Glu Cys Pro His Gln Ser Gly Ser Leu
305                 310                 315                 320

Pro Ser Trp Thr Val Ser Met Asp Thr Gln Ala Gln Gln Leu Thr Leu
                325                 330                 335

His Phe Ser Ser Arg Thr Tyr Ala Thr Phe Ser Ala Ala Trp Ser Asp
                340                 345                 350

Pro Gly Leu Gly Pro Asp Thr Pro Met Pro Pro Val Tyr Ser Ile Ser
        355                 360                 365

Gln Thr Gln Gly Ser Val Pro Val Thr Leu Asp Leu Ile Ile Pro Phe
    370                 375                 380

Leu Arg Gln Glu Asn Cys Ile Leu Val Trp Arg Ser Asp Val His Phe
385                 390                 395                 400

Ala Trp Lys His Val Leu Cys Pro Asp Val Ser His Arg His Leu Gly
                405                 410                 415

Leu Leu Ile Leu Ala Leu Leu Ala Leu Thr Ala Leu Val Gly Val Val
                420                 425                 430

Leu Val Leu Leu Gly Arg Arg Leu Leu Pro Gly Ser Gly Arg Thr Arg
        435                 440                 445

Pro Val Leu Leu Leu His Ala Ala Asp Ser Glu Ala Gln Arg Arg Leu
    450                 455                 460

Val Gly Ala Leu Ala Glu Leu Leu Arg Thr Ala Leu Gly Gly Gly Arg
465                 470                 475                 480

Asp Val Ile Val Asp Leu Trp Glu Gly Thr His Val Ala Arg Ile Gly
                485                 490                 495

Pro Leu Pro Trp Leu Trp Ala Ala Arg Glu Arg Val Ala Arg Glu Gln
                500                 505                 510

Gly Thr Val Leu Leu Leu Trp Asn Cys Ala Gly Pro Ser Thr Ala Cys
        515                 520                 525

Ser Gly Asp Pro Gln Ala Ala Ser Leu Arg Thr Leu Leu Cys Ala Ala
    530                 535                 540

Pro Arg Pro Leu Leu Leu Ala Tyr Phe Ser Arg Leu Cys Ala Lys Gly
545                 550                 555                 560

Asp Ile Pro Arg Pro Leu Arg Ala Leu Pro Arg Tyr Arg Leu Leu Arg
                565                 570                 575

Asp Leu Pro Arg Leu Leu Arg Ala Leu Asp Ala Gln Pro Ala Thr Leu
                580                 585                 590

Ala Ser Ser Trp Ser His Leu Gly Ala Lys Arg Cys Leu Lys Asn Arg
        595                 600                 605

Leu Glu Gln Cys His Leu Leu Glu Leu Glu Ala Lys Asp Asp Tyr
    610                 615                 620

Gln Gly Ser Thr Asn Ser Pro Cys Gly Phe Ser Cys Leu
625                 630                 635

<210> SEQ ID NO 7
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 7

Asp Tyr Ala Met His
1               5

<210> SEQ ID NO 8
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Tyr Ile Gly Gly Val Gly Glu Gly Thr Gln Tyr Ala Glu Ser Val Lys
1               5                   10                  15

Gly

<210> SEQ ID NO 9
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Phe Ala Ile Arg Tyr Tyr Gly Phe Asp Tyr
1               5                   10

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Phe Thr Val Ser Asp Tyr
1               5

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Gly Val Gly Glu Gly
1               5

<210> SEQ ID NO 12
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12
```

```
Gly Phe Ala Ile Arg Tyr Tyr Gly Phe Asp Tyr
1               5                  10
```

<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

```
Ser Gly Asp Lys Leu Gly Asp Lys Tyr Ala Tyr
1               5                  10
```

<210> SEQ ID NO 14
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

```
Gln Asp Ser Lys Arg Pro Ser
1               5
```

<210> SEQ ID NO 15
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

```
Gln Val Phe Thr Phe Pro Leu Val Thr Thr
1               5                  10
```

<210> SEQ ID NO 16
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

```
Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Val Phe Thr Phe Pro Leu Val Thr
                85                  90                  95
```

```
Thr Val Phe Gly Gly Gly Thr Lys Leu Thr Val Leu Gly Gln
                100                 105                 110
```

<210> SEQ ID NO 17
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Ala Met His Trp Val Arg Gln Ala Pro Gly Lys Gly Leu Glu Trp Val
        35                  40                  45

Ser Tyr Ile Gly Gly Val Gly Glu Gly Thr Gln Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Ala Ile Arg Tyr Tyr Gly Phe Asp Tyr Trp Gly Gln
            100                 105                 110

Gly Thr Leu Val Thr Val Ser Ser
        115                 120
```

<210> SEQ ID NO 18
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18

```
agctatgaac tgacccagcc gccgagcgtt agcgttagcc caggccagac cgccagcatt      60
acctgtagcg gcgacaaact gggcgacaaa tacgcctact ggtatcagca gaaaccgggc     120
cagagcccgg tgctggttat ctatcaggat agcaaacgcc cgagcggcat tccagaacgc     180
tttagcggca gcaacagcgg caacaccgcc accctgacca ttagcggcac ccaggccgaa     240
gacgaagccg attattactg ccaggttttc actttcccgc tggttactac tgtgtttggc     300
ggcggtacca agctgaccgt gctgggccag                                       330
```

<210> SEQ ID NO 19
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19

```
gaagtgcagc tgctggaaag cggtggcggt ctggtgcagc caggtggtag cctgcgcctg      60
agctgtgccg caagcggctt cacagtgtcc gactacgcaa tgcattgggt cgccaagca     120
```

```
ccaggcaaag gcctggaatg ggtgagttac ataggtggcg tgggtgaggg gacacaatat    180
gcagagagcg tgaaaggtcg ctttaccatt agtcgcgata acagcaaaaa caccctgtat    240
ctgcaaatga acagcctgcg ggcagaagat accgcagttt attattgcgc gcgtggtttc    300
gcaatccgtt attatggatt tgattattgg ggccagggca ccctggttac tgtctcgagc    360
```

<210> SEQ ID NO 20
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 20

Ser Asp His Tyr Ile Ser
1               5

<210> SEQ ID NO 21
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 21

Tyr Ile Ser Ser Ser Gly Ser Thr Thr Tyr Tyr Ala Glu Ser Val Lys
1               5                   10                  15

Gly

<210> SEQ ID NO 22
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 22

Gln Ser Tyr Tyr Phe Leu Pro Tyr Phe Asp Val
1               5                   10

<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 23

Gly Phe Thr Phe Ser Asp His
1               5

<210> SEQ ID NO 24
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 24

Ser Ser Ser Gly Ser Thr
1               5

<210> SEQ ID NO 25
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gln Ser Tyr Tyr Phe Leu Pro Tyr Phe Asp Val
1               5                   10

<210> SEQ ID NO 26
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Thr Gly Thr Ser Ser Asp Val Gly Ser Tyr Asn Leu Val Ser
1               5                   10

<210> SEQ ID NO 27
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Glu Gly Ser Lys Arg Pro Ser
1               5

<210> SEQ ID NO 28
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ala Ser Arg Gly Ser Arg Arg Val Leu Tyr Val
1               5                   10

<210> SEQ ID NO 29
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Ser Ala Leu Thr Gln Pro Ala Ser Val Ser Gly Ser Pro Gly Gln
```

```
                1               5                  10                 15
Ser Ile Thr Ile Ser Cys Thr Gly Thr Ser Ser Asp Val Gly Ser Tyr
                20                 25                 30

Asn Leu Val Ser Trp Tyr Gln Gln His Pro Gly Lys Ala Pro Lys Leu
        35                 40                 45

Met Ile Tyr Glu Gly Ser Lys Arg Pro Ser Gly Val Ser Asn Arg Phe
    50                 55                 60

Ser Gly Ser Lys Ser Gly Asn Thr Ala Ser Leu Thr Ile Ser Gly Leu
65                 70                 75                 80

Gln Ala Glu Asp Glu Ala Asp Tyr Tyr Cys Ala Ser Arg Gly Ser Arg
                85                 90                 95

Arg Val Leu Tyr Val Phe Gly Gly Gly Thr Lys Leu Thr Val Leu Gly
                100                105                110

Gln
```

<210> SEQ ID NO 30
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

```
Gln Val Gln Leu Val Glu Ser Gly Gly Gly Leu Val Lys Pro Gly Gly
1               5                  10                 15

Ser Leu Arg Leu Ser Cys Ala Ala Ser Gly Phe Thr Phe Ser Asp His
                20                 25                 30

Tyr Ile Ser Trp Ile Arg Gln Ala Pro Gly Lys Gly Leu Glu Trp Val
        35                 40                 45

Ser Tyr Ile Ser Ser Ser Gly Ser Thr Thr Tyr Tyr Ala Glu Ser Val
    50                 55                 60

Lys Gly Arg Phe Thr Ile Ser Arg Asp Asn Ala Lys Asn Ser Leu Tyr
65                 70                 75                 80

Leu Gln Met Asn Ser Leu Arg Ala Glu Asp Thr Ala Val Tyr Tyr Cys
                85                 90                 95

Ala Arg Gln Ser Tyr Tyr Phe Leu Pro Tyr Phe Asp Val Trp Gly Gln
                100                105                110

Gly Thr Leu Val Thr Val Ser Ser
        115                120
```

<210> SEQ ID NO 31
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

```
cagagcgccc tgacccagcc agccagcgtt agcggtagcc caggccagag cattaccatt     60
agctgcaccg gcaccagcag cgacgtgggc agctataacc tggttagctg gtatcagcag    120
catccgggca agcccccgaa actgatgatc tatgaaggca gcaaacgccc gagcggcgtt    180
agcaaccgct ttagtggcag caaaagcggc aacaccgcca gcctgaccat tagcggcctg    240
caagccgaag acgaagccga ttattactgc gcaagtcggg gaagccgtcg tgtgctgtat    300
```
gtttttggcg gcggtaccaa gctgaccgtg ctgggccag                                339

<210> SEQ ID NO 32
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32
caggtgcagc tggtggaaag cggcggtggc ctggtgaaac caggcggtag cctgcgcctg       60
agctgcgccg ccagcggctt tacctttagc gatcattaca ttagctggat tcgccaggcc      120
ccaggcaaag gcctggaatg ggttagctat attagcagca gtggcagcac cacctattac      180
gccgagagcg tgaaaggccg ctttaccatt agccgcgata cgccaaaaa cagcctgtat       240 ctgcaaatga acagcctgcg cgccgaagat accgccgtgt attattgcgc gcgacaatcc      300
tactatttcc tgccttattt cgacgtttgg ggccagggca ccctggttac tgtctcgagc      360

<210> SEQ ID NO 33
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
gactacgcaa tgcat                                                        15

<210> SEQ ID NO 34
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
tacataggtg gcgtgggtga ggggacacaa tatgcagaga gcgtgaaagg t                51

<210> SEQ ID NO 35
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
ggtttcgcaa tccgttatta tggatttgat tat                                    33

<210> SEQ ID NO 36
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
ggcttcacag tgtccgacta c                                        21

<210> SEQ ID NO 37
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
ggtggcgtgg gtgagggg                                            18

<210> SEQ ID NO 38
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
ggtttcgcaa tccgttatta tggatttgat tat                           33

<210> SEQ ID NO 39
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
agcggcgaca aactgggcga caaatacgcc tac                           33

<210> SEQ ID NO 40
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
caggatagca aacgcccgag c                                        21

<210> SEQ ID NO 41
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
caggtttcca ctttcccgct ggttactact                               30

<210> SEQ ID NO 42
<211> LENGTH: 214
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 42

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Tyr Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Val Phe Thr Phe Pro Leu Val Thr
                85                  90                  95

Thr Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 43
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asp Tyr
            20                  25                  30

Ala Met His Trp Val Arg Gln Ala Pro Gly Lys Gly Leu Glu Trp Val
        35                  40                  45

Ser Tyr Ile Gly Gly Val Gly Glu Gly Thr Gln Tyr Ala Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Gly Phe Ala Ile Arg Tyr Tyr Gly Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 44
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 44

```
agctatgaac tgacccagcc gccgagcgtt agcgttagcc caggccagac cgccagcatt      60
acctgtagcg gcgacaaact gggcgacaaa tacgcctact ggtatcagca gaaaccgggc     120
cagagcccgg tgctggttat ctatcaggat agcaaacgcc cgagcggcat tccagaacgc     180
tttagcggca gcaacagcgg caacaccgcc accctgacca ttagcggcac ccaggccgaa     240
gacgaagccg attattactg ccaggttttc actttcccgc tggttactac tgtgtttggc     300
ggcggtacca agctgaccgt gctgggccag cccaaagccg cccctagcgt gaccctgttc     360
cccccaagca gcgaggaact ccaggccaac aaggccaccc tcgtgtgcct gatcagcgac     420
ttctaccctg gcgccgtgac cgtggcctgg aaggccgata gcagccctgt gaaggccggc     480
gtggaaacca ccaccccag caagcagagc aacaacaaat acgccgccag cagctacctg     540
agcctgaccc ccgagcagtg gaagtcccac agatcctaca gctgccaggt cacacacgag     600
ggcagcaccg tggaaaagac cgtggccccc accgagtgca gc                       642
```

<210> SEQ ID NO 45
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 45

```
gaagtgcagc tgctggaaag cggtggcggt ctggtgcagc aggtggtag cctgcgcctg      60
agctgtgccg caagcggctt cacagtgtcc gactacgcaa tgcattgggt gcgccaagca    120
ccaggcaaag gcctggaatg ggtgagttac ataggtggcg tgggtgaggg gacacaatat    180
gcagagagcg tgaaaggtcg ctttaccatt agtcgcgata acagcaaaaa caccctgtat    240
ctgcaaatga acagcctgcg ggcagaagat accgcagttt attattgcgc gcgtggtttc    300
gcaatccgtt attatggatt tgattattgg ggccagggca ccctggttac tgtctcgagc    360
gcgtcgacca aggccccag cgtgttccct ctggccccca gcagcaagag cacctctggc    420
ggaacagccg ccctgggctg cctggtcaag gactacttcc ccgagcccgt gaccgtgtcc    480
tggaactctg gcgccctgac cagcggcgtg cacacctttc cagccgtgct ccagagcagc    540
ggcctgtaca gcctgagcag cgtcgtgacc gtgcccagca gcagcctggg cacccagacc    600
tacatctgca acgtgaacca caagcccagc aacacaaagg tggacaagcg ggtggaaccc    660
aagagctgcg acaagaccca cacctgtccc cctgccctg cccctgaact gctgggaggc    720
ccctccgtgt tcctgttccc cccaaagcct aaggacaccc tgatgatcag ccggaccccc    780
gaagtgacct gcgtggtggt ggacgtgtcc cacgaggacc ctgaagtgaa gtttaattgg    840
tacgtggacg gcgtggaagt gcacaacgcc aagaccaagc cagagagga acagtacaac    900
agcacctacc gggtggtgtc cgtgctgacc gtgctgcacc aggactggct gaacggcaaa    960
gagtacaagt gcaaggtgtc caacaaggcc ctgcctgccc ccatcgagaa aaccatcagc   1020
aaggccaaag gccagccccg cgagccccag gtgtacacac tgcccctag ccgggaagag   1080
atgaccaaga accaggtgtc cctgacctgc ctcgtgaagg gcttctaccc cagcgacatt   1140
gccgtggaat gggagagcaa cggccagccc gagaacaact acaagaccac ccccctgtg   1200
ctggacagcg acggctcatt cttcctgtac agcaagctga ccgtggacaa gagccggtgg   1260
cagcagggca acgtgttcag ctgctccgtg atgcacgagg ccctgcacaa ccactacacc   1320
```
cagaagtccc tgagcctgag ccccggcaag                                          1350

<210> SEQ ID NO 46
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
agcgatcatt acattagc                                                       18

<210> SEQ ID NO 47
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
tatattagca gcagtggcag caccacctat tacgccgaga gcgtgaaagg c                   51

<210> SEQ ID NO 48
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
caatcctact atttcctgcc ttatttcgac gtt                                       33

<210> SEQ ID NO 49
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
ggctttacct ttagcgatca t                                                   21

<210> SEQ ID NO 50
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
agcagcagtg gcagcacc                                                       18

<210> SEQ ID NO 51
<211> LENGTH: 33
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 51
caatcctact atttcctgcc ttatttcgac gtt                           33

<210> SEQ ID NO 52
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
accggcacca gcagcgacgt gggcagctat aacctggtta gc                 42

<210> SEQ ID NO 53
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
gaaggcagca aacgcccgag c                                        21

<210> SEQ ID NO 54
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
gcaagtcggg gaagccgtcg tgtgctgtat gtt                           33

<210> SEQ ID NO 55
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Arg Gly Ser Arg
                85                  90                  95
```

```
Arg Val Leu Tyr Val Phe Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 56
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp His
            20                  25                  30

Tyr Ile Ser Trp Ile Arg Gln Ala Pro Gly Lys Gly Leu Glu Trp Val
        35                  40                  45

Ser Tyr Ile Ser Ser Ser Gly Ser Thr Thr Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Ser Tyr Tyr Phe Leu Pro Tyr Phe Asp Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220
```

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 57
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57
cagagcgccc tgacccagcc agccagcgtt agcggtagcc caggccagag cattaccatt      60
agctgcaccg gcaccagcag cgacgtgggc agctataacc tggttagctg gtatcagcag     120
catccgggca agcccccgaa actgatgatc tatgaaggca gcaaacgccc gagcggcgtt     180
agcaaccgct tagtggcag caaaagcggc aacaccgcca gcctgaccat tagcggcctg     240
caagccgaag acgaagccga ttattactgc gcaagtcggg aagccgtcg tgtgctgtat     300 gtttttggcg gcggtaccaa gctgaccgtg ctgggccagc ccaaagccgc ccctagcgtg     360
accctgttcc ccccaagcag cgaggaactc caggccaaca aggccaccct cgtgtgcctg     420
atcagcgact tctaccctgg cgccgtgacc gtggcctgga aggccgatag cagccctgtg     480
aaggccggcg tggaaaccac cacccccagc aagcagagca caacaaata cgccgccagc     540 agctacctga gcctgacccc cgagcagtgg aagtcccaca gatcctacag ctgccaggtc     600
acacacgagg gcagcaccgt ggaaaagacc gtggccccca ccgagtgcag c             651

```
<210> SEQ ID NO 58
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
gactacgcta tgcac                                                    15

<210> SEQ ID NO 59
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
tatatcggcg gcgtgggcga gggcacccag tacgctgagt ctgtgaaggg c             51

<210> SEQ ID NO 60
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
ggcttcgcca tccggtacta cggcttcgac tac                                33

<210> SEQ ID NO 61
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
ggcttcaccg tgtccgacta c                                             21

<210> SEQ ID NO 62
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ggcggcgtgg gcgagggc                                                 18

<210> SEQ ID NO 63
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 63
ggcttcgcca tccggtacta cggcttcgac tac                              33

<210> SEQ ID NO 64
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
tccggcgaca agctgggcga taagtacgcc tac                              33

<210> SEQ ID NO 65
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
caggactcca agcggccctc c                                           21

<210> SEQ ID NO 66
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
caggtgttca ccttcccccct ggtcaccacc                                 30

<210> SEQ ID NO 67
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
tcctacgagc tgacccagcc cccctccgtg tccgtgtctc ctggccagac cgcctccatc   60
acctgttccg gcgacaagct gggcgataag tacgcctact ggtatcagca gaagcccggc  120
cagtcccccg tgctggtcat ctaccaggac tccaagcggc cctccggcat ccctgagcgg  180
ttctccggct ccaactccgg caacaccgcc accctgacca tctccggcac ccaggccgag  240
gacgaggccg actactactg ccaggtgttc accttccccc tggtcaccac cgtgttcggc  300
ggaggcacca agctgaccgt gctgggccag                                  330

<210> SEQ ID NO 68
<211> LENGTH: 360
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 68

```
gaggtgcagc tgctggaatc cggcggagga ctggtgcagc tggcggctc cctgagactg     60 tcttgcgccg cctccggctt caccgtgtcc gactacgcta tgcactgggt ccgacaggcc    120
cctggcaagg gcctggaatg ggtgtcctat atcggcggcg tgggcgaggg cacccagtac    180
gctgagtctg tgaagggccg gttcaccatc tcccgggaca actccaagaa caccctgtac    240
ctgcagatga actccctgcg ggccgaggac accgccgtgt actactgtgc cagaggcttc    300
gccatccggt actacggctt cgactactgg ggccagggca ccctggtcac cgtgtctagc    360
```

<210> SEQ ID NO 69
<211> LENGTH: 642
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69

```
tcctacgagc tgacccagcc cccctccgtg tccgtgtctc ctggccagac cgcctccatc     60
acctgttccg gcgacaagct gggcgataag tacgcctact ggtatcagca gaagcccggc    120
cagtcccccg tgctggtcat ctaccaggac tccaagcggc cctccggcat ccctgagcgg    180
ttctccggct ccaactccgg caacaccgcc accctgacca tctccggcac ccaggccgag    240
gacgaggccg actactactg ccaggtgttc accttcccc tggtcaccac cgtgttcggc     300
ggaggcacca agctgaccgt gctgggccag cctaaggccg ctccctccgt gaccctgttc    360
cccccatcct ccgaggaact gcaggccaac aaggccaccc tggtctgcct gatctccgac    420
ttctaccctg gcgccgtgac cgtggcctgg aaggccgaca gctctcctgt gaaggccggc    480
gtggaaacca ccaccccctc caagcagtcc aacaacaaat acgccgcctc ctcctacctg    540
tccctgaccc ccgagcagtg gaagtcccac cggtcctaca gctgccaggt cacacacgag    600
ggctccaccg tggaaaagac cgtggcccct accgagtgct cc                       642
```

<210> SEQ ID NO 70
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 70

```
gaggtgcagc tgctggaatc cggcggagga ctggtgcagc tggcggctc cctgagactg     60 tcttgcgccg cctccggctt caccgtgtcc gactacgcta tgcactgggt ccgacaggcc    120
cctggcaagg gcctggaatg ggtgtcctat atcggcggcg tgggcgaggg cacccagtac    180
gctgagtctg tgaagggccg gttcaccatc tcccgggaca actccaagaa caccctgtac    240
ctgcagatga actccctgcg ggccgaggac accgccgtgt actactgtgc cagaggcttc    300
gccatccggt actacggctt cgactactgg ggccagggca ccctggtcac cgtgtctagc    360
gcctccacca agggcccctc cgtgttccct ctggccccct ccagcaagtc cacctctggc    420
ggcaccgctg ccctgggctg cctggtcaag gactacttcc ccgagcccgt gaccgtgtcc    480
tggaactctg gcgccctgac ctccggcgtg cacaccttcc ctgccgtgct gcagtcctcc    540
```

```
ggcctgtact ccctgtcctc cgtcgtgacc gtgccctcca gctctctggg cacccagacc    600
tacatctgca acgtgaacca caagccctcc aacaccaagg tggacaagcg ggtggaaccc    660
aagtcctgcg acaagaccca cacctgtccc ccctgccctg ccctgaact gctgggcgga     720 ccttccgtgt tcctgttccc cccaaagccc aaggacaccc tgatgatctc ccggaccccc    780
gaagtgacct gcgtggtggt ggacgtgtcc cacgaggacc ctgaagtgaa gttcaattgg    840
tacgtggacg gcgtggaagt gcacaacgcc aagaccaagc cagagagga acagtacaac     900 tccacctacc gggtggtgtc cgtgctgacc gtgctgcacc aggactggct gaacggcaaa    960
gagtacaagt gcaaggtgtc caacaaggcc ctgcctgccc ccatcgaaaa gaccatctcc    1020
aaggccaagg gccagccccg cgagcccag gtgtacacac tgcccctag ccgggaagag      1080 atgaccaaga accaggtgtc cctgacctgt ctggtcaagg gcttctaccc ctccgacatt    1140
gccgtggaat gggagtccaa cggccagccc gagaacaact acaagaccac cccccctgtg   1200
ctggactccg acggctcatt cttcctgtac tccaagctga ccgtggacaa gtcccggtgg    1260
cagcagggca acgtgttctc ctgctccgtg atgcacgagg ccctgcacaa ccactacacc    1320
cagaagtccc tgtccctgag ccccggcaag                                     1350
```

<210> SEQ ID NO 71
<211> LENGTH: 1350
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 71

```
caggtgcagc tggtggaaag cggcggtggc ctggtgaaac aggcggtag cctgcgcctg     60 agctgcgccg ccagcggctt tacctttagc gatcattaca ttagctggat tcgccaggcc    120
ccaggcaaag gcctggaatg ggttagctat attagcagca gtggcagcac cacctattac    180
gccgagagcg tgaaaggccg ctttaccatt agccgcgata cgccaaaaa cagcctgtat    240 ctgcaaatga acagcctgcg ggccgaagat accgccgtgt attattgcgc gcgacaatcc    300
tactatttcc tgccttattt cgacgtttgg ggccagggca ccctggttac tgtctcgagc    360
gcgtcgacca aaggccccag cgtgttccct ctggccccca gcagcaagag cacctctggc    420
ggaacagccg ccctgggctg cctggtcaag gactacttcc ccgagcccgt gaccgtgtcc    480
tggaactctg gcgccctgac cagcggcgtg cacacctttc cagccgtgct ccagagcagc    540
ggcctgtaca gcctgagcag cgtcgtgacc gtgcccagca gcagcctggg cacccagacc    600
tacatctgca acgtgaacca caagcccagc aacacaaagg tggacaagcg ggtggaaccc    660
aagagctgcg acaagaccca cacctgtccc ccctgccctg ccctgaact gctgggaggc    720 cccctccgtgt tcctgttccc cccaaagcct aaggacaccc tgatgatcag ccggaccccc    780
gaagtgacct gcgtggtggt ggacgtgtcc cacgaggacc ctgaagtgaa gttaattgg     840 tacgtggacg gcgtggaagt gcacaacgcc aagaccaagc cagagagga acagtacaac     900 agcacctacc gggtggtgtc cgtgctgacc gtgctgcacc aggactggct gaacggcaaa    960
gagtacaagt gcaaggtgtc caacaaggcc ctgcctgccc ccatcgagaa accatcagc     1020 aaggccaaag gccagccccg cgagcccag gtgtacacac tgcccctag ccgggaagag     1080 atgaccaaga accaggtgtc cctgacctgc ctcgtgaagg gcttctaccc cagcgacatt    1140
```

-continued

```
gccgtggaat gggagagcaa cggccagccc gagaacaact acaagaccac cccccctgtg    1200
ctggacagcg acggctcatt cttcctgtac agcaagctga ccgtggacaa gagccggtgg    1260
cagcagggca acgtgttcag ctgctccgtg atgcacgagg ccctgcacaa ccactacacc    1320
cagaagtccc tgagcctgag ccccggcaag                                     1350
```